US008663653B2

(12) United States Patent
Gottwein et al.

(10) Patent No.: US 8,663,653 B2
(45) Date of Patent: Mar. 4, 2014

(54) EFFICIENT CELL CULTURE SYSTEM FOR HEPATITIS C VIRUS GENOTYPE 2B

(75) Inventors: Judith M. Gottwein, Frederiksberg C (DK); Maria Lisa Knudsen, Stockholm (DK); Troels Kasper Høyer Scheel, København NV (DK); Jens Bukh, Praestø (DK)

(73) Assignee: Hvidovre Hospital, Hvidovre (DK)

( * ) Notice: Subject to any disclaimer, the term of this patent is extended or adjusted under 35 U.S.C. 154(b) by 106 days.

(21) Appl. No.: 13/059,130

(22) PCT Filed: Jul. 24, 2009

(86) PCT No.: PCT/DK2009/050189
§ 371 (c)(1),
(2), (4) Date: Aug. 5, 2011

(87) PCT Pub. No.: WO2010/017818
PCT Pub. Date: Feb. 18, 2010

(65) Prior Publication Data
US 2011/0294194 A1 Dec. 1, 2011

(30) Foreign Application Priority Data

Aug. 15, 2008 (EP) .................................... 08162466

(51) Int. Cl.
*A61K 39/12* (2006.01)
*A61K 39/29* (2006.01)
*C12Q 1/70* (2006.01)
*C12N 15/00* (2006.01)
*C12N 5/071* (2010.01)
*C12N 1/20* (2006.01)

(52) U.S. Cl.
USPC .................. 424/228.1; 424/202.1; 424/204.1; 424/205.1; 424/225.1; 435/5; 435/440; 435/455; 435/370; 435/252.3

(58) Field of Classification Search
None
See application file for complete search history.

(56) References Cited

U.S. PATENT DOCUMENTS

| | | | |
|---|---|---|---|
| 5,428,145 A | 6/1995 | Okamoto et al. | |
| 6,638,714 B1 | 10/2003 | Linnen et al. | |
| 7,674,612 B2 | 3/2010 | Rice et al. | |
| 7,935,676 B2 | 5/2011 | Wakita et al. | |
| 2007/0073039 A1 | 3/2007 | Chisari | |
| 2010/0093841 A1 | 4/2010 | Gottwein et al. | |
| 2010/0158948 A1 | 6/2010 | Scheel et al. | |
| 2010/0278865 A1 | 11/2010 | Wakita et al. | |
| 2010/0291545 A1 | 11/2010 | Wakita et al. | |
| 2011/0021611 A1 | 1/2011 | Jensen et al. | |
| 2011/0045020 A1 | 2/2011 | Akazawa et al. | |
| 2011/0059512 A1 | 3/2011 | Gottwein et al. | |
| 2011/0059513 A1 | 3/2011 | Scheel et al. | |
| 2011/0092688 A1 | 4/2011 | Wakita et al. | |
| 2011/0294195 A1 | 12/2011 | Gottwein et al. | |
| 2012/0003714 A1 | 1/2012 | Hoelke et al. | |
| 2012/0003719 A1 | 1/2012 | Prento et al. | |

FOREIGN PATENT DOCUMENTS

| | | |
|---|---|---|
| EP | 1801209 A1 | 6/2007 |
| EP | 1930416 A1 | 6/2008 |
| WO | 9904008 A2 | 1/1999 |
| WO | 0121807 A1 | 3/2001 |
| WO | 02052015 A2 | 7/2002 |
| WO | 02059321 A2 | 8/2002 |
| WO | 2004/104198 A1 | 12/2004 |
| WO | 2005047463 A2 | 5/2005 |
| WO | 2005053516 A2 | 6/2005 |
| WO | 2006096459 A2 | 9/2006 |
| WO | 2007037429 A1 | 4/2007 |
| WO | 2007041487 A2 | 4/2007 |
| WO | 2007073039 A1 | 6/2007 |
| WO | 2008125117 A1 | 10/2008 |
| WO | 2008125119 A1 | 10/2008 |
| WO | 2008141651 A1 | 11/2008 |
| WO | 2009080052 A1 | 7/2009 |
| WO | 2009080053 A1 | 7/2009 |
| WO | 2011/118743 A1 | 9/2011 |

OTHER PUBLICATIONS

Gottwein et al., "Development and Characterization of Hepatitis C Virus Genotype 1-7 Cell Culture Systems: Role of CD91 and Scavenger Receptor Class B Type I and Effect of Antiviral Drugs", Hepatology, Oct. 9, 2008, pp. 364-377, vol. 49, No. 2.
Gottwein et al., "Novel Chimeric Cell Culture System for Hepatitis C Genotypes 1A, 1B, 3A and 4A", Annual Meeting of the European Association for the Study of the Liver, Apr. 2007, pp. S30, vol. 46, No. Suppl.
Gottwein et al., "Robust Hepatitis C Genotype 3a Cell Culture Releasing Adapted Intergenotypic 3a/2a (S52/JFH1) Viruses", Gastroenterology, Nov. 2007, pp. 1614-1626, vol. 133, No. 5, Elsevier, Philadelphia, PA.
Graham et al., "A Genotype 2b NS5B Polymerase with Novel Substitutions Supports Replication of a Chimeric HCV 1b: 2b Replicon Containing a Genotype 1b NS3-5A Background", Antiviral Research, Jan. 2006, pp. 24-30, vol. 69, No. 1, Elsevier Science BV., Amsterdam, NL.
Kato et al., "Efficient Replication of the Genotype 2a Hepatitis C Virus Subgenomic Replicon", Gastroenterology, Dec. 2003, pp. 1808-1817, vol. 125, No. 6, Elsevier, Philadelphia, PA.
Kaul et al., "Cell Culture Adaption of Hepatitis C Virus and in vivo Viability of an Adapted Varient", Journal of Virology, Dec. 2007, pp. 13168-13179, vol. 81, No. 23, The American Society for Microbiology, US.

(Continued)

*Primary Examiner* — Louise Humphrey
(74) *Attorney, Agent, or Firm* — Thompson Coburn LLP; Charles P. Romano

(57) ABSTRACT

The present inventors developed hepatitis C virus 2b/2a intergenotypic recombinants in which the JFH1 structural genes (Core, E1 and E2), p7 and the complete NS2 were replaced by the corresponding genes of the genotype 2b reference strain J8. Sequence analysis of recovered 2b/2a recombinants from 2 transfection experiments revealed that 2b/2a was genetically stable. Conclusion: The developed 2b/2a viruses provide a robust in vitro tool for research in HCV genotype 2b, including vaccine studies and functional analysis.

17 Claims, 18 Drawing Sheets

(56) References Cited

OTHER PUBLICATIONS

Figure 1A:
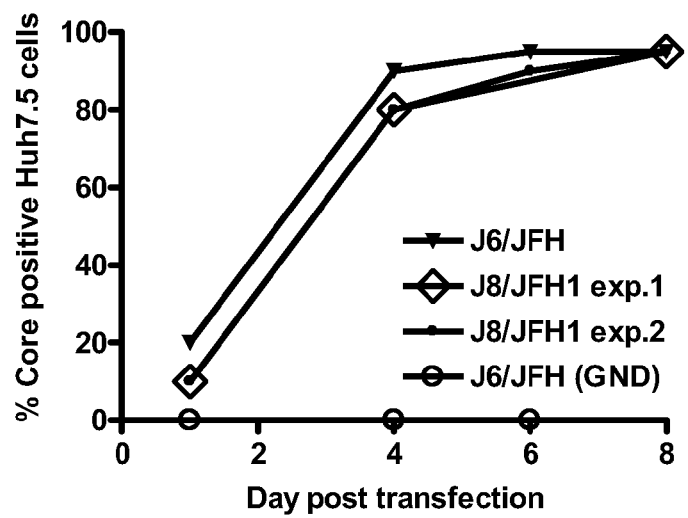

Krieger et al., "Enhancement of Hepatitis C Virus RNA Replication by Cell Culture-Adaptive Mutations", Journal of Virology, May 2001, pp. 4614-4624, vol. 75, No. 10, The American Society for Microbiology, US.

Lindenbach et al., "Complete Replication of Hepatitis C Virus in Cell Culture", Science, Jul. 22, 2005, pp. 623-626, vol. 309, No. 5734.

Lohmann et al., "Mutation in Hepatitis C Virus RNAs Conferring Cell Culture Adaptation", Journal of Virology, Feb. 2001, pp. 1437-1449, vol. 75, No. 3, The American Society for Microbiology, US.

Pietschmann et al., "Construction and Characterization of Infectious Intragenotypic and Intergenotypic Hepatitis C Virus Chimeras", Proceedings of the National Academy of Science of USA, May 9, 2006, pp. 7408-7413, vol. 103, No. 19, National Academy of Science, Washington D.C.

Scheel et al., "Development of JFH1-based Cell Culture Systems for Hepatitis C Virus Genotype 4a and Evidence for Cross-Genotype Neutralization", Proceedings of the National Academy of Science of USA, Jan. 22, 2008, pp. 997-1002, vol. 105, No. 3, National Academy of Science, Washington D.C., US.

Wakita et al., "Production of Infectious Hepatitis C Virus in Tissue Culture from a Cloned Viral Genome", Nature Medicine, Jul. 2005, pp. 791-796, vol. 11, No. 7, Nature Publishing Group, New York, NY.

Yanagi et al., "Transcripts of a Chimeric cDNA Clone of Hepatitis C Virus Genotype 1b are Infectious in vivo", Virology, Jan. 1, 1998, pp. 161-172, vol. 244, No. 1.

Yi et al., "Compensatory Mutations in E1, p7, NS2, and NS3 Enhance Yields of Cell Culture-Infectious Intergenotypic Chimeric Hepatitis C Virus", Journal of Virology, Jan. 2007, pp. 629-638, vol. 81, No. 2, American Society for Microbiology, US.

Sakai et al, "In Vivo Study of the HC-TN Strain of Hepatitis C Virus Recovered from a Patient with Fulminant Hepatitis: TNA Transcripts of a Molecular Clone (pHC-TN) are Infectious in Chimpanzees But Not in Huh7.5 Cells", Journal of Virology, Jul. 2007, pp. 7208-7219, vol. 81, No. 13, American Society for Microbiology.

Gottwein et al., "Cutting the Gordian Knot-Development and Biological Relevance of Hepatitis C Virus Cell Culture Systems", Advances in Virus Research, 2008, pp. 51-133, vol. 71.

International Preliminary Report on Patentability for PCT/DK2008/050333 dated Mar. 29, 2010.

International Search Report and Written Opinion of the International Searching Authority dated Nov. 3, 2009 for PCT Application No. PCT/DK2008/050332.

Hui et al., "Interferon and Ribavirin Therapy for Chronic Hepatitis C Virus Genotype 6: A Comparison with Genotype 1", Article, Apr. 1, 2003, pp. 1071-1074, vol. 87.

GenBank Accession No. AB047639.1, HCV JFH1 complete genomic RNA, Nov. 12, 2005.

GenBank Accession No. Y12083.1, HCV genotype 6a RNA for HCV polyprotein, Nov. 10, 2005.

Kato et al., "Sequence Analysis of Hepatitis C Virus Isolated From a Fulminant Hepatitis Patient", Journal of Medical Virology, 2001, pp. 334-339, vol. 64.

Zhong et al., "Robust hepatitis C virus infection in vitro", Proceedings of the National Academy of Sciences, 2005, pp. 9294-9299, vol. 102 No. 26.

"Written Description Training Materials", United States Patent and Trademark Office, Department of Commerce, Mar. 2008, pp. 1-84, Revision 1 (part 2).

Appel et al., "Mutational Analysis of Hepatitis C Virus Nonstructural Protein 5A: Potential Role of Differential Phosphorylation in RNA Replication and Identification of a Genetically Flexible Domain", Journal of Virology, Mar. 2005, pp. 3187-3194, vol. 79, No. 5.

Appel et al, "Essential Role of Domain III of Nonstructural Protein 5A for Hepatitis C Virus Infectious Particle Assembly", PLOS Pathogens, Mar. 2008, pp. 1-14, vol. 4, Issue 3.

Bukh et al., "Mutations That Permit Efficient Replication of Hepatitis C Virus RNA in Huh-7 Cells Prevent Productive Replication in Chimpanzees", Proc. Natl. Acad. Sci., Oct. 29, 2002, pp. 14416-14421, vol. 99, No. 22.

Chamberlain et al., "Complete Nucleotide Sequence of a Type 4 Hepatitis C Virus Variant, the Predominant Genotype in the Middle East", Journal of General Virology, 1997, pp. 1341-1347, vol. 78.

Forns et al., "Hepatitis C Virus Lacking the Hypervariable Region 1 of the Second Envelope Protein is Infectious and Causes Acute Resolving or Persistent Infection in Chimpanzees", Proceedings of the National Academy of Sciences of the United States of America, Nov. 21, 2000, pp. 13318-13323, vol. 97, No. 24.

Gottwein et al., "Monocistronic Hepatitis C Reporter Virus Recombinants of All Major Genotypes Expressing Enhanced Green Fluorescent Protein Tagged NS5A Protein", Journal of Hepatology, Apr. 2009, p. S33, vol. 50, No. sup1.

Hou et al., "A Recombinant Replication-Competent Hepatitis C Virus Expressing Azami-Green, a Bright Green-Emitting Fluorescent Protein, Suitable for Visualization of Infected Cells", Biochemical and Biophysical Research Communications, Sep. 9, 2008, pp. 7-11, vol. 377, No. 1.

Jensen et al., "Highly Efficient JFH1-Based Cell-Culture System for Hepatitis C Virus Genotype 5a: Failure of Homologous Neutralizing-Antibody Treatment to Control Infection", Journal of Infectious Diseases, Dec. 15, 2008, pp. 1756-1765, vol. 198.

Jensen, "Efficient Cell Culture System for Hepatitis C Virus Genotype 5a", Department of Infectious Diseases and Clinical Research Unit, Copenhagen University Hospital, Master Thesis, Mar. 2007, pp. 1-60.

Kim et al., "Monitoring the Antiviral Effect of Alpha Interferon on Individual Cells" Journal of Virology, Aug. 2007, pp. 8814-8820, vol. 81, No. 16.

Moradpour et al., "Insertion of Green Fluorescent Protein into Nonstructural Protein 5A Allows Direct Visualization of Functional Hepatitis C Virus Replication Complexes", Journal of Virology, Jul. 2004, pp. 7400-7409, vol. 78, No. 14.

Prentoe et al., "HCV Entry Related Studies", Booklet, 4th Smogen Summer Symposium on Virology, Aug. 2008, p. 23.

Schaller et al., "Analysis of Hepatitis C Virus Superinfection Exclusion by Using Novel Fluorochrome Gene-Tagged Viral Genomes", Journal of Virology, May 2007, pp. 4591-4603, vol. 81, No. 9.

Suzuki et al., "Novel Chimeric Hepatitis C Virus Genome Comprising Nucleic Acid Encoding Epitope Tag Peptide at Hypervariable Region 1 of E2 Protein, Useful as Vaccine for Preventing or Treating Hepatitis-C Viral Infection", Database WPI Week 200914, Thomson Scientific, AN 2009-E03534, Jan. 22, 2009.

International Preliminary Report on Patentability (Chapter II) for PCT/DK2008/050113 issued May 25, 2009.

"Written Description Training Materials", United States Patent and Trademark Office, Department of Commerce, Mar. 2008, pp. 1-84, Revision 1 (Part 1).

International Search Report and Written Opinion for PCT/DK2009/050193 dated Oct. 30, 2009.

Simmonds et al., "Consensus Proposals for a Unified System of Nomenclature of Hepatitis C Virus Genotypes", Hepatology, Oct. 2005, pp. 962-973, vol. 42, No. 4.

Murphy et al., "A New Genotype of Hepatitis C Virus Originating from Central Africa", Hepatology, Oct. 2007, pp. 623A, vol. 46, No. 4, Suppl. S.

Murphy, "Hepatitis C Virus Isolate QC69 Polyprotein Gene, Complete CDs", Database EMBL E.B.I. Hinxton U.K., Nov. 2007, XP002520134 Database Accession No. EF108306.

SEQUENCE LISTING

<160> NUMBER OF SEQ ID NOS: 14

<210> SEQ ID NO 1
<211> LENGTH: 9678
<212> TYPE: DNA
<213> ORGANISM: Hepatitis C virus

<400> SEQUENCE: 1

| | | | | | |
|---|---|---|---|---|---|
| acctgcccct | aatagggggcg | acactccgcc | atgaatcact | cccctgtgag | gaactactgt | 60 |
| cttcacgcag | aaagcgccta | gccatggcgt | tagtatgagt | gtcgtacagc | ctccaggccc | 120 |
| cccctcccg | ggagagccat | agtggtctgc | ggaaccggtg | agtacaccgg | aattgccggg | 180 |
| aagactgggt | cctttcttgg | ataaacccac | tctatgcccg | gccatttggg | cgtgcccccg | 240 |
| caagactgct | agccgagtag | cgttgggttg | cgaaaggcct | tgtggtactg | cctgataggg | 300 |
| tgcttgcgag | tgccccggga | ggtctcgtag | accgtgcacc | atgagcacaa | atcctaaacc | 360 |
| tcaaagaaaa | accaaaagaa | acacaaaccg | ccgcccacag | gacgttaagt | tcccgggtgg | 420 |
| cggtcagatc | gttggcggag | tttacttgct | gccgcgcagg | ggccccaggt | tgggtgtgcg | 480 |
| cgcgacaagg | aagacttctg | agcgatccca | gccgcgtgga | cgacgccagc | ccatcccgaa | 540 |
| agatcggcgc | tccaccggca | agtcctgggg | aaagccagga | tatccttggc | ccctgtacgg | 600 |
| aaacgagggt | tgcggctggg | cgggttggct | cctgtccccc | cgcgggtctc | gtcctacttg | 660 |
| gggcccacc | gaccccggc | atagatcacg | caatttgggc | agagtcatcg | ataccattac | 720 |
| gtgtggtttt | gccgacctca | tggggtacat | ccctgtcgtt | ggcgcccgg | ttggaggcgt | 780 |
| cgccagagct | ctggcacacg | tgttagggt | cctggaggac | gggataaatt | acgcaacagg | 840 |
| gaatttaccc | ggttgctctt | tttctatctt | tttgcttgct | cttctgtcat | gcgtcacagt | 900 |
| gccagtgtct | gcagtggaag | tcaggaacat | tagttctagc | tactacgcca | ctaatgattg | 960 |
| ctcaaacaac | agcatcacct | ggcagctcac | tgacgcagtt | ctccatcttc | ctggatgcgt | 1020 |
| cccatgtgag | aatgataatg | gcaccttgca | ttgctggata | caagtaacac | ccaacgtggc | 1080 |
| tgtgaaacac | cgcggtgcgc | tcactcgtag | cctgcgaaca | cacgtcgaca | tgatcgtaat | 1140 |
| ggcagctacg | gcctgctcgg | ccttgtatgt | gggagatgtg | tgcggggccg | tgatgattct | 1200 |
| atcgcaggct | ttcatggtat | caccacaacg | ccacaacttc | acccaagagt | gcaactgttc | 1260 |
| catctaccaa | ggtcacatca | ccggccatcg | catggcatgg | gacatgatgc | tgaactggtc | 1320 |
| tccaactctt | gccatgatcc | tcgcctacgc | cgctcgtgtt | cccgagatgg | tcctcgaaat | 1380 |
| tattttcggc | ggccattggg | gtgtggtgtt | tggcttggcc | tacttctcca | tgcaaggagc | 1440 |
| gtgggccaaa | gtcattgcca | tcctccttct | tgttgcggga | gtggatgcaa | ccacctattc | 1500 |
| cagcggccag | gaagcgggtc | gtaccgtctt | ggggttcact | aacctcttta | cttctggtgc | 1560 |
| caagcagaac | tctctatttaa | tcaacaccaa | tggcagctgg | cacataaacc | ggactgcccct | 1620 |
| caattgcaat | gacagcttac | agacgggttt | catggcttcc | ctgttttaca | cccacaggtt | 1680 |
| caacagctct | ggctgccccg | agcgcttgtc | ttcctgccgc | gggctggacg | attttcgcat | 1740 |
| cggctgggga | accttggaat | acgaaaccca | cgtcaccaac | gatgaggaca | tgaggccgta | 1800 |
| ctgctggcat | taccctccga | ggccttgcgg | catcgtcccg | gctagaacgg | tttgcggacc | 1860 |
| ggtctattgt | ttcacccta | gccctgttgt | cgtgggcacc | actgacaagc | agggcgtacc | 1920 |
| cacctacacc | tgggggaaa | acgagaccga | tgtcttcctg | ctgaatagca | caagaccccc | 1980 |
| gcgaggagct | tggttcggct | gcacttggat | gaacgggact | gggttcacta | agacatgcgg | 2040 |

```
tgcaccacct tgccgcatta ggaaagacta caacagcact atcgatttat tgtgcccac    2100 agactgtttt aggaagcacc ccgatgctac ctatcttaag tgtggagcag ggccttggtt    2160
aactcccagg tgcctggtag actacccttta tagactgtgg cattatccgt gcactgtaaa   2220
cttcaccatc tttaaggcgc ggatgtatgt aggaggggtg gagcatcgat tctccgcagc   2280
atgcaacttc acgcgcggag atcgctgcag actggaagat agggataggg gtcagcagag   2340
tccactgctg cattccacta ctgagtgggc ggtgctccca tgctccttct ctgacctacc   2400
agcactatcc actggcctat tgcacctcca ccaaaacatc gtggacgtgc agtacccttta  2460 cggactttct ccggctctga caagatacat cgtgaagtgg gagtgggtga tcctcctttt   2520
cttgttgttg gcagacgcca ggatctgtgc atgcctttgg atgctcatca tactgggcca   2580
agccgaagcg gcgcttgaga agctcatcat cttgcactcc gctagtgctg ctagtgccaa   2640
tggtccgctg tggttttttca tcttctttac agcggcctgg tacttaaagg gcagggtggt   2700
ccccgtggcc acgtactctg ttctcggctt atggtccttc ctcctcctag tcctggcctt    2760
accacagcag gcttatgcct tggacgctgc tgaacaaggg gaactggggc tggccatatt   2820
agtaattata tccatctttta ctcttacccc agcatacaag atcctcctga gccgttcagt   2880
gtggtggctg tcctacatgc tggtcttggc cgaggcccag attcagcaat gggttccccc    2940
cctggaggtc cgaggggggc gtgacggaat catctgggtg gctgtcattc tacacccacg   3000
ccttgtgttt gaggtcacga aatggttgtt agcaatcctg gggcctgcct acctccttaa   3060
agcgtctctg ctacggatac cgtactttgt gagggcccac gctttgctac gagtgtgtac   3120
cctggtgaaa cacctcgcgg gggctaggta catccagatg ctgttgatca ccataggcag   3180
atggaccggc acttacatct acgaccacct ctccccttta tcaacttggg cggcccaggg   3240
tttgcgggac ctggcaatcg ccgtggagcc tgtggtgttc agcccaatgg agaagaaggt    3300
cattgtgtgg ggggctgaga cagtggcgtg tggagacatc ctgcatggcc tcccggtctc   3360
cgcgaggcta ggtagggagg ttctgctcgg ccctgccgac ggctacacct caagggggtg   3420
gaagctccta gctcccatca ctgcttatgc ccagcaaaca cgaggcctcc tgggcgccat   3480
agtggtgagt atgacggggc gtgacaggac agaacaggcc ggggaagtcc aaatcctgtc   3540
cacagtctct cagtccttcc tcggaacaac catctcgggg gttttgtgga ctgtttacca   3600
cggagctggc aacaagactc tagccggctt acggggtccg gtcacgcaga tgtactcgag   3660
tgctgagggg gacttggtag gctggcccag ccccctggg accaagtctt tggagccgtg    3720
caagtgtgga gccgtcgacc tatatctggt cacgcggaac gctgatgtca tcccggctcg   3780
gagacgcggg gacaagcggg gagcattgct ctccccgaga cccatttcga ccttgaaggg   3840
gtcctcgggg gggccggtgc tctgccctag gggccacgtc gttgggctct tccgagcagc   3900
tgtgtgctct cggggcgtgg ccaaatccat cgatttcatc cccgttgaga cactcgacgt   3960
tgttacaagg tctcccactt tcagtgacaa cagcacgcca ccggctgtgc cccagaccta   4020
tcaggtcggg tacttgcatg ctccaactgg cagtggaaag agcaccaagg tccctgtcgc   4080
gtatgccgcc caggggtaca agtactagt gcttaaccccc tcggtagctg ccaccctggg   4140
gtttggggcg tacctatcca aggcacatgg catcaatccc aacattagga ctggagtcag   4200
gaccgtgatg accggggagg ccatcacgta ctccacatat ggcaaatttc tcgccgatgg   4260
gggctgcgct agcggcgcct atgacatcat catatgcgat gaatgccacg ctgtggatgc   4320
tacctccatt ctcggcatcg gaacggtcct tgatcaagca gagacagccg gggtcagact   4380
aactgtgctg gctacggcca cacccccggg gtcagtgaca accccccatc ccgatataga   4440
```

-continued

| | | | | |
|---|---|---|---|---|
| agaggtaggc | ctcgggcggg | agggtgagat | cccettctat | gggagggcga | ttccectatc | 4500 |
| ctgcatcaag | ggagggagac | acctgatttt | ctgccactca | agaaaaagt | gtgacgagct | 4560 |
| cgcggcggcc | cttcggggca | tgggcttgaa | tgccgtggca | tactatagag | ggttggacgt | 4620 |
| ctccataata | ccagctcagg | gagatgtggt | ggtcgtcgcc | accgacgccc | tcatgacggg | 4680 |
| gtacactgga | gactttgact | ccgtgatcga | ctgcaatgta | gcggtcaccc | aagctgtcga | 4740 |
| cttcagcctg | gaccccacct | tcactataac | cacacagact | gtcccacaag | acgctgtctc | 4800 |
| acgcagtcag | cgccgcgggc | gcacaggtag | aggaagacag | ggcacttata | ggtatgtttc | 4860 |
| cactggtgaa | cgagcctcag | gaatgtttga | cagtgtagtg | cttttgtgagt | gctacgacgc | 4920 |
| aggggctgcg | tggtacgatc | tcacaccagc | ggagaccacc | gtcaggctta | gagcgtattt | 4980 |
| caacacgccc | ggcctacccg | tgtgtcaaga | ccatcttgaa | ttttgggagg | cagttttcac | 5040 |
| cggcctcaca | cacatagacg | cccacttcct | ctcccaaaca | aagcaagcgg | gggagaactt | 5100 |
| cgcgtaccta | gtagcctacc | aagctacggt | gtgcgccaga | gccaaggccc | ctcccccgtc | 5160 |
| ctgggacgcc | atgtggaagt | gcctggcccg | actcaagcct | acgcttgcgg | gccccacacc | 5220 |
| tctcctgtac | cgtttgggcc | ctattaccaa | tgaggtcacc | ctcacacacc | ctgggacgaa | 5280 |
| gtacatcgcc | acatgcatgc | aagctgacct | tgaggtcatg | accagcacgt | gggtcctagc | 5340 |
| tggaggagtc | ctggcagccg | tcgccgcata | ttgcctggcg | actggatgcg | tttccatcat | 5400 |
| cggccgcttg | cacgtcaacc | agcgagtcgt | cgttgcgccg | gataaggagg | tcctgtatga | 5460 |
| ggcttttgat | gagatggagg | aatgcgcctc | tagggcggct | ctcatcgaag | aggggcagcg | 5520 |
| gataccgag | atgttgaagt | ccaagatcca | aggcttgctg | cagcaggcct | ctaagcaggc | 5580 |
| ccaggacata | caacccgcta | tgcaggcttc | atggcccaaa | gtggaacaat | tttgggccag | 5640 |
| acacatgtgg | aacttcatta | gcggcatcca | atacctcgca | ggattgtcaa | cactgccagg | 5700 |
| gaaccccgcg | gtggcttcca | tgatggcatt | cagtgccgcc | ctcaccagtc | cgttgtcgac | 5760 |
| cagtaccacc | atccttctca | acatcatggg | aggctggtta | gcgtcccaga | tcgcaccacc | 5820 |
| cgcggggggcc | accggctttg | tcgtcagtgg | cctggtgggg | gctgccgtgg | gcagcatagg | 5880 |
| cctgggtaag | gtgctggtgg | acatcctggc | aggatatggt | gcgggcattt | cgggggccct | 5940 |
| cgtcgcattc | aagatcatgt | ctggcgagaa | gccctctatg | gaagatgtca | tcaatctact | 6000 |
| gcctgggatc | ctgtctccgg | gagccctggt | ggtggggggtc | atctgcgcgg | ccattctgcg | 6060 |
| ccgccacgtg | ggaccgggggg | agggcgcggt | ccaatggatg | aacaggctta | ttgccttttgc | 6120 |
| ttccagagga | aaccacgtcg | cccctactca | ctacgtgacg | gagtcggatg | cgtcgcagcg | 6180 |
| tgtgacccaa | ctacttggct | ctcttactat | aaccagccta | ctcagaagac | tccacaattg | 6240 |
| gataactgag | gactgcccca | tcccatgctc | cggatcctgg | ctccgcgacg | tgtgggactg | 6300 |
| ggtttgcacc | atcttgacag | acttcaaaaa | ttggctgacc | tctaaattgt | tccccaagct | 6360 |
| gcccggcctc | cccttcatct | cttgtcaaaa | ggggtacaag | ggtgtgtggg | ccggcactgg | 6420 |
| catcatgacc | acgcgctgcc | cttgcggcgc | caacatctct | ggcaatgtcc | gcctgggctc | 6480 |
| tatgaggatc | acagggccta | aaacctgcat | gaacacctgg | caggggacct | tcctatcaa | 6540 |
| ttgctacacg | gagggccagt | gcgcgccgaa | acccccacg | aactacaaga | ccgccatctg | 6600 |
| gagggtggcg | gcctcggagt | acgcggaggt | gacgcagcat | gggtcgtact | cctatgtaac | 6660 |
| aggactgacc | actgacaatc | tgaaaattcc | ttgccaacta | ccttctccag | agttttctc | 6720 |
| ctgggtggac | ggtgtgcaga | tccataggtt | tgcacccaca | ccaaagccgt | ttttccggga | 6780 |
| tgaggtctcg | ttctgcgttg | ggcttaattc | ctatgctgtc | gggtcccagc | ttccctgtga | 6840 |

-continued

```
acctgagccc gacgcagacg tattgaggtc catgctaaca gatccgcccc acatcacggc   6900
ggagactgcg gcgcggcgct tggcacgggg atcacctcca tctgaggcga gctcctcagt   6960
gagccagcta tcagcaccgt cgctgcgggc cacctgcacc acccacagca acacctatga   7020
cgtggacatg gtcgatgcca acctgctcat ggagggcggt gtggctcaga cagagcctga   7080
gtccagggtg cccgttctgg actttctcga gccaatggcc gaggaagaga gcgaccttga   7140
gccctcaata ccatcggagt gcatgctccc caggagcggg tttccacggg ccttaccggc   7200
ttgggcacgg cctgactaca acccgccgct cgtggaatcg tggaggaggc cagattacca   7260
accgccacc gttgctggtt gtgctctccc cccccccaag aaggcccga cgcctccccc   7320
aaggagacgc cggacagtgg gtctgagcga gagcaccata tcagaagccc tccagcaact   7380
ggccatcaag acctttggcc agcccccctc gagcggtgat gcaggctcgt ccacgggggc   7440
gggcgccgcc gaatccggcg gtccgacgtc ccctggtgag ccggcccct cagagacagg   7500
ttccgcctcc tctatgcccc ccctcgaggg ggagcctgga gatccggacc tggagtctga   7560
tcaggtagag cttcaacctc cccccaggg gggggggta gctcccggtt cgggctcggg   7620
gtcttggtct acttgctccg aggaggacga taccaccgtg tgctgctcca tgtcatactc   7680
ctggaccggg gctctaataa ctccctgtag ccccgaagag gaaaagttgc caatcaaccc   7740
tttgagtaac tcgctgttgc gataccataa caaggtgtac tgtacaacat caaagagcgc   7800
ctcacagagg gctaaaaagg taacttttga caggacgcaa gtgctcgacg cccattatga   7860
ctcagtctta aaggacatca agctagcggc ttccaaggtc agcgcaaggc tcctcacctt   7920
ggaggaggcg tgccagttga ctccaccca ttctgcaaga tccaagtatg gattcggggc   7980
caaggaggtc cgcagcttgt ccgggagggc cgttaaccac atcaagtccg tgtggaagga   8040
cctcctggaa gacccacaaa caccaattcc cacaaccatc atggccaaaa atgaggtgtt   8100
ctgcgtggac cccgccaagg ggggtaagaa accagctcgc ctcatcgttt accctgacct   8160
cggcgtccgg gtctgcgaga aaatggccct ctatgacatt acacaaaagc ttcctcaggc   8220
ggtaatggga gcttcctatg gcttccagta ctccctgcc caacgggtgg agtatctctt   8280
gaaagcatgg gcggaaaaga aggaccccat gggttttcg tatgataccc gatgcttcga   8340
ctcaaccgtc actgagagag acatcaggac cgaggagtcc atataccagg cctgctccct   8400
gcccgaggag gcccgcactg ccatacactc gctgactgag agactttacg taggagggcc   8460
catgttcaac agcaagggtc aaacctgcgg ttacagacgt tgccgcgcca gcggggtgct   8520
aaccactagc atgggtaaca ccatcacatg ctatgtgaaa gccctagcgg cctgcaaggc   8580
tgcggggata gttgcgccca caatgctggt atgcggcgat gacctagtag tcatctcaga   8640
aagccagggg actgaggagg acgagcggaa cctgagagcc ttcacggagg ccatgaccag   8700
gtactctgcc cctcctggtg atccccccag accggaatat gacctggagc taataacatc   8760
ctgttcctca aatgtgtctg tggcgttggg cccgcgggc cgccgcagat actacctgac   8820
cagagaccca accactccac tcgcccgggc tgcctgggaa acagttagac actcccctat   8880
caattcatgg ctgggaaaca tcatccagta tgctccaacc atatgggttc gcatggtcct   8940
aatgacacac ttcttctcca ttctcatggt ccaagacacc ctggaccaga acctcaactt   9000
tgagatgtat ggatcagtat actccgtgaa tcctttggac cttccagcca taattgagag   9060
gttacacggg cttgacgcct tttctatgca cacatactct caccacgaac tgacgcgggt   9120
ggcttcagcc ctcagaaaac ttgggggcgcc acccctcagg gtgtgaaga gtcgggctcg   9180
cgcagtcagg gcgtccctca tctcccgtgg agggaaagcg gccgtttgcg ccgatatct   9240
```

-continued

```
cttcaattgg gcggtgaaga ccaagctcaa actcactcca ttgccggagg cgcgcctact    9300
ggacttatcc agttggttca ccgtcggcgc cggcggggc gacattttc acagcgtgtc     9360 gcgcgcccga ccccgctcat tactcttcgg cctactccta cttttcgtag gggtaggcct    9420
cttcctactc cccgctcggt agagcggcac acactaggta cactccatag ctaactgttc    9480
cttttttttt tttttttttt tttttttttt tttttttttt ttttcttttt ttttttttc     9540 cctcttcctt ccettctcat cttattctac tttcttcctt ggtggctcca tcttagccct    9600
agtcacggct agctgtgaaa ggtccgtgag ccgcatgact gcagagagtg ccgtaactgg    9660
tctctctgca gatcatgt                                                   9678
```

<210> SEQ ID NO 2
<211> LENGTH: 3033
<212> TYPE: PRT
<213> ORGANISM: Hepatitis C virus

<400> SEQUENCE: 2

```
Met Ser Thr Asn Pro Lys Pro Gln Arg Lys Thr Lys Arg Asn Thr Asn
 1               5                  10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Thr Trp Gly Pro Thr Asp Pro
            100                 105                 110

Arg His Arg Ser Arg Asn Leu Gly Arg Val Ile Asp Thr Ile Thr Cys
        115                 120                 125

Gly Phe Ala Asp Leu Met Gly Tyr Ile Pro Val Val Gly Ala Pro Val
    130                 135                 140

Gly Gly Val Ala Arg Ala Leu Ala His Gly Val Arg Val Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Val Thr Val Pro Val Ser Ala Val
            180                 185                 190

Glu Val Arg Asn Ile Ser Ser Ser Tyr Tyr Ala Thr Asn Asp Cys Ser
        195                 200                 205

Asn Asn Ser Ile Thr Trp Gln Leu Thr Asp Ala Val Leu His Leu Pro
    210                 215                 220

Gly Cys Val Pro Cys Glu Asn Asp Asn Gly Thr Leu His Cys Trp Ile
225                 230                 235                 240

Gln Val Thr Pro Asn Val Ala Val Lys His Arg Gly Ala Leu Thr Arg
                245                 250                 255

Ser Leu Arg Thr His Val Asp Met Ile Val Met Ala Thr Ala Cys
            260                 265                 270

Ser Ala Leu Tyr Val Gly Asp Val Cys Gly Ala Val Met Ile Leu Ser
        275                 280                 285

Gln Ala Phe Met Val Ser Pro Gln Arg His Asn Phe Thr Gln Glu Cys
    290                 295                 300
```

```
Asn Cys Ser Ile Tyr Gln Gly His Ile Thr Gly His Arg Met Ala Trp
305                 310                 315                 320

Asp Met Met Leu Asn Trp Ser Pro Thr Leu Ala Met Ile Leu Ala Tyr
            325                 330                 335

Ala Ala Arg Val Pro Glu Met Val Leu Glu Ile Ile Phe Gly Gly His
        340                 345                 350

Trp Gly Val Val Phe Gly Leu Ala Tyr Phe Ser Met Gln Gly Ala Trp
    355                 360                 365

Ala Lys Val Ile Ala Ile Leu Leu Val Ala Gly Val Asp Ala Thr
370                 375                 380

Thr Tyr Ser Ser Gly Gln Glu Ala Gly Arg Thr Val Leu Gly Phe Thr
385                 390                 395                 400

Asn Leu Phe Thr Ser Gly Ala Lys Gln Asn Leu Tyr Leu Ile Asn Thr
            405                 410                 415

Asn Gly Ser Trp His Ile Asn Arg Thr Ala Leu Asn Cys Asn Asp Ser
            420                 425                 430

Leu Gln Thr Gly Phe Met Ala Ser Leu Phe Tyr Thr His Arg Phe Asn
            435                 440                 445

Ser Ser Gly Cys Pro Glu Arg Leu Ser Ser Cys Arg Gly Leu Asp Asp
450                 455                 460

Phe Arg Ile Gly Trp Gly Thr Leu Glu Tyr Glu Thr His Val Thr Asn
465                 470                 475                 480

Asp Glu Asp Met Arg Pro Tyr Cys Trp His Tyr Pro Arg Pro Cys
            485                 490                 495

Gly Ile Val Pro Ala Arg Thr Val Cys Gly Pro Val Tyr Cys Phe Thr
            500                 505                 510

Pro Ser Pro Val Val Gly Thr Thr Asp Lys Gln Gly Val Pro Thr
    515                 520                 525

Tyr Thr Trp Gly Glu Asn Glu Thr Asp Val Phe Leu Leu Asn Ser Thr
    530                 535                 540

Arg Pro Pro Arg Gly Ala Trp Phe Gly Cys Thr Trp Met Asn Gly Thr
545                 550                 555                 560

Gly Phe Thr Lys Thr Cys Gly Ala Pro Pro Cys Arg Ile Arg Lys Asp
                565                 570                 575

Tyr Asn Ser Thr Ile Asp Leu Leu Cys Pro Thr Asp Cys Phe Arg Lys
            580                 585                 590

His Pro Asp Ala Thr Tyr Leu Lys Cys Gly Ala Gly Pro Trp Leu Thr
            595                 600                 605

Pro Arg Cys Leu Val Asp Tyr Pro Tyr Arg Leu Trp His Tyr Pro Cys
            610                 615                 620

Thr Val Asn Phe Thr Ile Phe Lys Ala Arg Met Tyr Val Gly Gly Val
625                 630                 635                 640

Glu His Arg Phe Ser Ala Ala Cys Asn Phe Thr Arg Gly Asp Arg Cys
                645                 650                 655

Arg Leu Glu Asp Arg Asp Arg Gly Gln Ser Pro Leu Leu His Ser
            660                 665                 670

Thr Thr Glu Trp Ala Val Leu Pro Cys Ser Phe Ser Asp Leu Pro Ala
            675                 680                 685

Leu Ser Thr Gly Leu Leu His Leu His Gln Asn Ile Val Asp Val Gln
690                 695                 700

Tyr Leu Tyr Gly Leu Ser Pro Ala Leu Thr Arg Tyr Ile Val Lys Trp
705                 710                 715                 720

Glu Trp Val Ile Leu Leu Phe Leu Leu Leu Ala Asp Ala Arg Ile Cys
                725                 730                 735
```

```
        Ala Cys Leu Trp Met Leu Ile Ile Leu Gly Gln Ala Glu Ala Ala Leu
                        740                 745                 750

Glu Lys Leu Ile Ile Leu His Ser Ala Ser Ala Ala Ser Ala Asn Gly
                        755                 760                 765

Pro Leu Trp Phe Phe Ile Phe Phe Thr Ala Ala Trp Tyr Leu Lys Gly
                        770                 775                 780

Arg Val Val Pro Val Ala Thr Tyr Ser Val Leu Gly Leu Trp Ser Phe
        785                 790                 795                 800

Leu Leu Leu Val Leu Ala Leu Pro Gln Gln Ala Tyr Ala Leu Asp Ala
                        805                 810                 815

Ala Glu Gln Gly Glu Leu Gly Leu Ala Ile Leu Val Ile Ile Ser Ile
                        820                 825                 830

Phe Thr Leu Thr Pro Ala Tyr Lys Ile Leu Leu Ser Arg Ser Val Trp
                        835                 840                 845

Trp Leu Ser Tyr Met Leu Val Leu Ala Glu Ala Gln Ile Gln Gln Trp
                        850                 855                 860

Val Pro Pro Leu Glu Val Arg Gly Gly Arg Asp Gly Ile Ile Trp Val
        865                 870                 875                 880

Ala Val Ile Leu His Pro Arg Leu Val Phe Glu Val Thr Lys Trp Leu
                        885                 890                 895

Leu Ala Ile Leu Gly Pro Ala Tyr Leu Leu Lys Ala Ser Leu Leu Arg
                        900                 905                 910

Ile Pro Tyr Phe Val Arg Ala His Ala Leu Leu Arg Val Cys Thr Leu
                        915                 920                 925

Val Lys His Leu Ala Gly Ala Arg Tyr Ile Gln Met Leu Leu Ile Thr
        930                 935                 940

Ile Gly Arg Trp Thr Gly Thr Tyr Ile Tyr Asp His Leu Ser Pro Leu
        945                 950                 955                 960

Ser Thr Trp Ala Ala Gln Gly Leu Arg Asp Leu Ala Ile Ala Val Glu
                        965                 970                 975

Pro Val Val Phe Ser Pro Met Glu Lys Lys Val Ile Val Trp Gly Ala
                        980                 985                 990

Glu Thr Val Ala Cys Gly Asp Ile  Leu His Gly Leu Pro  Val Ser Ala
                        995                 1000                1005

Arg Leu  Gly Arg Glu Val Leu  Leu Gly Pro Ala Asp  Gly Tyr Thr
             1010                 1015                1020

Ser Lys  Gly Trp Lys Leu Leu  Ala Pro Ile Thr Ala  Tyr Ala Gln
             1025                 1030                1035

Gln Thr  Arg Gly Leu Leu Gly  Ala Ile Val Val Ser  Met Thr Gly
             1040                 1045                1050

Arg Asp  Arg Thr Glu Gln Ala  Gly Glu Val Gln Ile  Leu Ser Thr
             1055                 1060                1065

Val Ser  Gln Ser Phe Leu Gly  Thr Thr Ile Ser Gly  Val Leu Trp
             1070                 1075                1080

Thr Val  Tyr His Gly Ala Gly  Asn Lys Thr Leu Ala  Gly Leu Arg
             1085                 1090                1095

Gly Pro  Val Thr Gln Met Tyr  Ser Ser Ala Glu Gly  Asp Leu Val
             1100                 1105                1110

Gly Trp  Pro Ser Pro Pro Gly  Thr Lys Ser Leu Glu  Pro Cys Lys
             1115                 1120                1125

Cys Gly  Ala Val Asp Leu Tyr  Leu Val Thr Arg Asn  Ala Asp Val
             1130                 1135                1140

Ile Pro  Ala Arg Arg Arg Gly  Asp Lys Arg Gly Ala  Leu Leu Ser
             1145                 1150                1155
```

```
Pro Arg Pro Ile Ser Thr Leu Lys Gly Ser Ser Gly Gly Pro Val
1160                 1165                 1170

Leu Cys Pro Arg Gly His Val Val Gly Leu Phe Arg Ala Ala Val
1175                 1180                 1185

Cys Ser Arg Gly Val Ala Lys Ser Ile Asp Phe Ile Pro Val Glu
1190                 1195                 1200

Thr Leu Asp Val Val Thr Arg Ser Pro Thr Phe Ser Asp Asn Ser
1205                 1210                 1215

Thr Pro Pro Ala Val Pro Gln Thr Tyr Gln Val Gly Tyr Leu His
1220                 1225                 1230

Ala Pro Thr Gly Ser Gly Lys Ser Thr Lys Val Pro Val Ala Tyr
1235                 1240                 1245

Ala Ala Gln Gly Tyr Lys Val Leu Val Leu Asn Pro Ser Val Ala
1250                 1255                 1260

Ala Thr Leu Gly Phe Gly Ala Tyr Leu Ser Lys Ala His Gly Ile
1265                 1270                 1275

Asn Pro Asn Ile Arg Thr Gly Val Arg Thr Val Met Thr Gly Glu
1280                 1285                 1290

Ala Ile Thr Tyr Ser Thr Tyr Gly Lys Phe Leu Ala Asp Gly Gly
1295                 1300                 1305

Cys Ala Ser Gly Ala Tyr Asp Ile Ile Ile Cys Asp Glu Cys His
1310                 1315                 1320

Ala Val Asp Ala Thr Ser Ile Leu Gly Ile Gly Thr Val Leu Asp
1325                 1330                 1335

Gln Ala Glu Thr Ala Gly Val Arg Leu Thr Val Leu Ala Thr Ala
1340                 1345                 1350

Thr Pro Pro Gly Ser Val Thr Thr Pro His Pro Asp Ile Glu Glu
1355                 1360                 1365

Val Gly Leu Gly Arg Glu Gly Glu Ile Pro Phe Tyr Gly Arg Ala
1370                 1375                 1380

Ile Pro Leu Ser Cys Ile Lys Gly Gly Arg His Leu Ile Phe Cys
1385                 1390                 1395

His Ser Lys Lys Lys Cys Asp Glu Leu Ala Ala Ala Leu Arg Gly
1400                 1405                 1410

Met Gly Leu Asn Ala Val Ala Tyr Tyr Arg Gly Leu Asp Val Ser
1415                 1420                 1425

Ile Ile Pro Ala Gln Gly Asp Val Val Val Ala Thr Asp Ala
1430                 1435                 1440

Leu Met Thr Gly Tyr Thr Gly Asp Phe Asp Ser Val Ile Asp Cys
1445                 1450                 1455

Asn Val Ala Val Thr Gln Ala Val Asp Phe Ser Leu Asp Pro Thr
1460                 1465                 1470

Phe Thr Ile Thr Thr Gln Thr Val Pro Gln Asp Ala Val Ser Arg
1475                 1480                 1485

Ser Gln Arg Arg Gly Arg Thr Gly Arg Gly Arg Gln Gly Thr Tyr
1490                 1495                 1500

Arg Tyr Val Ser Thr Gly Glu Arg Ala Ser Gly Met Phe Asp Ser
1505                 1510                 1515

Val Val Leu Cys Glu Cys Tyr Asp Ala Gly Ala Ala Trp Tyr Asp
1520                 1525                 1530

Leu Thr Pro Ala Glu Thr Thr Val Arg Leu Arg Ala Tyr Phe Asn
1535                 1540                 1545

Thr Pro Gly Leu Pro Val Cys Gln Asp His Leu Glu Phe Trp Glu
1550                 1555                 1560
```

```
Ala Val Phe Thr Gly Leu Thr His Ile Asp Ala His Phe Leu Ser
1565                1570                1575

Gln Thr Lys Gln Ala Gly Glu Asn Phe Ala Tyr Leu Val Ala Tyr
1580                1585                1590

Gln Ala Thr Val Cys Ala Arg Ala Lys Ala Pro Pro Pro Ser Trp
1595                1600                1605

Asp Ala Met Trp Lys Cys Leu Ala Arg Leu Lys Pro Thr Leu Ala
1610                1615                1620

Gly Pro Thr Pro Leu Leu Tyr Arg Leu Gly Pro Ile Thr Asn Glu
1625                1630                1635

Val Thr Leu Thr His Pro Gly Thr Lys Tyr Ile Ala Thr Cys Met
1640                1645                1650

Gln Ala Asp Leu Glu Val Met Thr Ser Thr Trp Val Leu Ala Gly
1655                1660                1665

Gly Val Leu Ala Ala Val Ala Ala Tyr Cys Leu Ala Thr Gly Cys
1670                1675                1680

Val Ser Ile Ile Gly Arg Leu His Val Asn Gln Arg Val Val Val
1685                1690                1695

Ala Pro Asp Lys Glu Val Leu Tyr Glu Ala Phe Asp Glu Met Glu
1700                1705                1710

Glu Cys Ala Ser Arg Ala Ala Leu Ile Glu Glu Gly Gln Arg Ile
1715                1720                1725

Ala Glu Met Leu Lys Ser Lys Ile Gln Gly Leu Leu Gln Gln Ala
1730                1735                1740

Ser Lys Gln Ala Gln Asp Ile Gln Pro Ala Met Gln Ala Ser Trp
1745                1750                1755

Pro Lys Val Glu Gln Phe Trp Ala Arg His Met Trp Asn Phe Ile
1760                1765                1770

Ser Gly Ile Gln Tyr Leu Ala Gly Leu Ser Thr Leu Pro Gly Asn
1775                1780                1785

Pro Ala Val Ala Ser Met Met Ala Phe Ser Ala Ala Leu Thr Ser
1790                1795                1800

Pro Leu Ser Thr Ser Thr Thr Ile Leu Leu Asn Ile Met Gly Gly
1805                1810                1815

Trp Leu Ala Ser Gln Ile Ala Pro Pro Ala Gly Ala Thr Gly Phe
1820                1825                1830

Val Val Ser Gly Leu Val Gly Ala Ala Val Gly Ser Ile Gly Leu
1835                1840                1845

Gly Lys Val Leu Val Asp Ile Leu Ala Gly Tyr Gly Ala Gly Ile
1850                1855                1860

Ser Gly Ala Leu Val Ala Phe Lys Ile Met Ser Gly Glu Lys Pro
1865                1870                1875

Ser Met Glu Asp Val Ile Asn Leu Leu Pro Gly Ile Leu Ser Pro
1880                1885                1890

Gly Ala Leu Val Val Gly Val Ile Cys Ala Ala Ile Leu Arg Arg
1895                1900                1905

His Val Gly Pro Gly Glu Gly Ala Val Gln Trp Met Asn Arg Leu
1910                1915                1920

Ile Ala Phe Ala Ser Arg Gly Asn His Val Ala Pro Thr His Tyr
1925                1930                1935

Val Thr Glu Ser Asp Ala Ser Gln Arg Val Thr Gln Leu Leu Gly
1940                1945                1950

Ser Leu Thr Ile Thr Ser Leu Leu Arg Arg Leu His Asn Trp Ile
1955                1960                1965
```

-continued

Thr Glu Asp Cys Pro Ile Pro Cys Ser Gly Ser Trp Leu Arg Asp
1970                1975                1980

Val Trp Asp Trp Val Cys Thr Ile Leu Thr Asp Phe Lys Asn Trp
1985                1990                1995

Leu Thr Ser Lys Leu Phe Pro Lys Leu Pro Gly Leu Pro Phe Ile
2000                2005                2010

Ser Cys Gln Lys Gly Tyr Lys Gly Val Trp Ala Gly Thr Gly Ile
2015                2020                2025

Met Thr Thr Arg Cys Pro Cys Gly Ala Asn Ile Ser Gly Asn Val
2030                2035                2040

Arg Leu Gly Ser Met Arg Ile Thr Gly Pro Lys Thr Cys Met Asn
2045                2050                2055

Thr Trp Gln Gly Thr Phe Pro Ile Asn Cys Tyr Thr Glu Gly Gln
2060                2065                2070

Cys Ala Pro Lys Pro Pro Thr Asn Tyr Lys Thr Ala Ile Trp Arg
2075                2080                2085

Val Ala Ala Ser Glu Tyr Ala Glu Val Thr Gln His Gly Ser Tyr
2090                2095                2100

Ser Tyr Val Thr Gly Leu Thr Thr Asp Asn Leu Lys Ile Pro Cys
2105                2110                2115

Gln Leu Pro Ser Pro Glu Phe Phe Ser Trp Val Asp Gly Val Gln
2120                2125                2130

Ile His Arg Phe Ala Pro Thr Pro Lys Pro Phe Phe Arg Asp Glu
2135                2140                2145

Val Ser Phe Cys Val Gly Leu Asn Ser Tyr Ala Val Gly Ser Gln
2150                2155                2160

Leu Pro Cys Glu Pro Glu Pro Asp Ala Asp Val Leu Arg Ser Met
2165                2170                2175

Leu Thr Asp Pro Pro His Ile Thr Ala Glu Thr Ala Ala Arg Arg
2180                2185                2190

Leu Ala Arg Gly Ser Pro Pro Ser Glu Ala Ser Ser Ser Val Ser
2195                2200                2205

Gln Leu Ser Ala Pro Ser Leu Arg Ala Thr Cys Thr Thr His Ser
2210                2215                2220

Asn Thr Tyr Asp Val Asp Met Val Asp Ala Asn Leu Leu Met Glu
2225                2230                2235

Gly Gly Val Ala Gln Thr Glu Pro Glu Ser Arg Val Pro Val Leu
2240                2245                2250

Asp Phe Leu Glu Pro Met Ala Glu Glu Glu Ser Asp Leu Glu Pro
2255                2260                2265

Ser Ile Pro Ser Glu Cys Met Leu Pro Arg Ser Gly Phe Pro Arg
2270                2275                2280

Ala Leu Pro Ala Trp Ala Arg Pro Asp Tyr Asn Pro Pro Leu Val
2285                2290                2295

Glu Ser Trp Arg Arg Pro Asp Tyr Gln Pro Pro Thr Val Ala Gly
2300                2305                2310

Cys Ala Leu Pro Pro Pro Lys Lys Ala Pro Thr Pro Pro Pro Arg
2315                2320                2325

Arg Arg Arg Thr Val Gly Leu Ser Glu Ser Thr Ile Ser Glu Ala
2330                2335                2340

Leu Gln Gln Leu Ala Ile Lys Thr Phe Gly Gln Pro Pro Ser Ser
2345                2350                2355

Gly Asp Ala Gly Ser Ser Thr Gly Ala Gly Ala Ala Glu Ser Gly
2360                2365                2370

-continued

```
Gly Pro Thr Ser Pro Gly Glu Pro Ala Pro Ser Glu Thr Gly Ser
    2375            2380            2385

Ala Ser Ser Met Pro Pro Leu Glu Gly Glu Pro Gly Asp Pro Asp
    2390            2395            2400

Leu Glu Ser Asp Gln Val Glu Leu Gln Pro Pro Gln Gly Gly
    2405            2410            2415

Gly Val Ala Pro Gly Ser Gly Ser Gly Ser Trp Ser Thr Cys Ser
    2420            2425            2430

Glu Glu Asp Asp Thr Thr Val Cys Cys Ser Met Ser Tyr Ser Trp
    2435            2440            2445

Thr Gly Ala Leu Ile Thr Pro Cys Ser Pro Glu Glu Glu Lys Leu
    2450            2455            2460

Pro Ile Asn Pro Leu Ser Asn Ser Leu Leu Arg Tyr His Asn Lys
    2465            2470            2475

Val Tyr Cys Thr Thr Ser Lys Ser Ala Ser Gln Arg Ala Lys Lys
    2480            2485            2490

Val Thr Phe Asp Arg Thr Gln Val Leu Asp Ala His Tyr Asp Ser
    2495            2500            2505

Val Leu Lys Asp Ile Lys Leu Ala Ala Ser Lys Val Ser Ala Arg
    2510            2515            2520

Leu Leu Thr Leu Glu Glu Ala Cys Gln Leu Thr Pro Pro His Ser
    2525            2530            2535

Ala Arg Ser Lys Tyr Gly Phe Gly Ala Lys Glu Val Arg Ser Leu
    2540            2545            2550

Ser Gly Arg Ala Val Asn His Ile Lys Ser Val Trp Lys Asp Leu
    2555            2560            2565

Leu Glu Asp Pro Gln Thr Pro Ile Pro Thr Thr Ile Met Ala Lys
    2570            2575            2580

Asn Glu Val Phe Cys Val Asp Pro Ala Lys Gly Gly Lys Lys Pro
    2585            2590            2595

Ala Arg Leu Ile Val Tyr Pro Asp Leu Gly Val Arg Val Cys Glu
    2600            2605            2610

Lys Met Ala Leu Tyr Asp Ile Thr Gln Lys Leu Pro Gln Ala Val
    2615            2620            2625

Met Gly Ala Ser Tyr Gly Phe Gln Tyr Ser Pro Ala Gln Arg Val
    2630            2635            2640

Glu Tyr Leu Leu Lys Ala Trp Ala Glu Lys Lys Asp Pro Met Gly
    2645            2650            2655

Phe Ser Tyr Asp Thr Arg Cys Phe Asp Ser Thr Val Thr Glu Arg
    2660            2665            2670

Asp Ile Arg Thr Glu Glu Ser Ile Tyr Gln Ala Cys Ser Leu Pro
    2675            2680            2685

Glu Glu Ala Arg Thr Ala Ile His Ser Leu Thr Glu Arg Leu Tyr
    2690            2695            2700

Val Gly Gly Pro Met Phe Asn Ser Lys Gly Gln Thr Cys Gly Tyr
    2705            2710            2715

Arg Arg Cys Arg Ala Ser Gly Val Leu Thr Thr Ser Met Gly Asn
    2720            2725            2730

Thr Ile Thr Cys Tyr Val Lys Ala Leu Ala Ala Cys Lys Ala Ala
    2735            2740            2745

Gly Ile Val Ala Pro Thr Met Leu Val Cys Gly Asp Asp Leu Val
    2750            2755            2760

Val Ile Ser Glu Ser Gln Gly Thr Glu Glu Asp Glu Arg Asn Leu
    2765            2770            2775
```

```
Arg Ala Phe Thr Glu Ala Met Thr Arg Tyr Ser Ala Pro Pro Gly
    2780            2785                2790

Asp Pro Pro Arg Pro Glu Tyr Asp Leu Glu Leu Ile Thr Ser Cys
    2795            2800                2805

Ser Ser Asn Val Ser Val Ala Leu Gly Pro Arg Gly Arg Arg Arg
    2810            2815                2820

Tyr Tyr Leu Thr Arg Asp Pro Thr Thr Pro Leu Ala Arg Ala Ala
    2825            2830                2835

Trp Glu Thr Val Arg His Ser Pro Ile Asn Ser Trp Leu Gly Asn
    2840            2845                2850

Ile Ile Gln Tyr Ala Pro Thr Ile Trp Val Arg Met Val Leu Met
    2855            2860                2865

Thr His Phe Phe Ser Ile Leu Met Val Gln Asp Thr Leu Asp Gln
    2870            2875                2880

Asn Leu Asn Phe Glu Met Tyr Gly Ser Val Tyr Ser Val Asn Pro
    2885            2890                2895

Leu Asp Leu Pro Ala Ile Ile Glu Arg Leu His Gly Leu Asp Ala
    2900            2905                2910

Phe Ser Met His Thr Tyr Ser His His Glu Leu Thr Arg Val Ala
    2915            2920                2925

Ser Ala Leu Arg Lys Leu Gly Ala Pro Pro Leu Arg Val Trp Lys
    2930            2935                2940

Ser Arg Ala Arg Ala Val Arg Ala Ser Leu Ile Ser Arg Gly Gly
    2945            2950                2955

Lys Ala Ala Val Cys Gly Arg Tyr Leu Phe Asn Trp Ala Val Lys
    2960            2965                2970

Thr Lys Leu Lys Leu Thr Pro Leu Pro Glu Ala Arg Leu Leu Asp
    2975            2980                2985

Leu Ser Ser Trp Phe Thr Val Gly Ala Gly Gly Asp Ile Phe
    2990            2995                3000

His Ser Val Ser Arg Ala Arg Pro Arg Ser Leu Leu Phe Gly Leu
    3005            3010                3015

Leu Leu Leu Phe Val Gly Val Gly Leu Phe Leu Leu Pro Ala Arg
    3020            3025                3030

<210> SEQ ID NO 3
<211> LENGTH: 40
<212> TYPE: DNA
<213> ORGANISM: Artificial Sequence
<220> FEATURE:
<223> OTHER INFORMATION: oligoDNA primer

<400> SEQUENCE: 3
gtagcgttgg gttgcgaaag gccttgtggt actgcctgat                        40

<210> SEQ ID NO 4
<211> LENGTH: 25
<212> TYPE: DNA
<213> ORGANISM: Artificial Sequence
<220> FEATURE:
<223> OTHER INFORMATION: oligoDNA primer

<400> SEQUENCE: 4
caatgacttt ggcccacgct ccttg                                        25

<210> SEQ ID NO 5
<211> LENGTH: 26
<212> TYPE: DNA
<213> ORGANISM: Artificial Sequence
```

```
<220> FEATURE:
<223> OTHER INFORMATION: oligoDNA primer

<400> SEQUENCE: 5
ccatcgcatg gcatgggaca tgatgc                                          26

<210> SEQ ID NO 6
<211> LENGTH: 23
<212> TYPE: DNA
<213> ORGANISM: Artificial Sequence
<220> FEATURE:
<223> OTHER INFORMATION: oligoDNA primer

<400> SEQUENCE: 6
gcagcgatct ccgcgcgtga agt                                             23

<210> SEQ ID NO 7
<211> LENGTH: 27
<212> TYPE: DNA
<213> ORGANISM: Artificial Sequence
<220> FEATURE:
<223> OTHER INFORMATION: oligoDNA primer

<400> SEQUENCE: 7
gcttggttcg gctgcacttg gatgaac                                         27

<210> SEQ ID NO 8
<211> LENGTH: 27
<212> TYPE: DNA
<213> ORGANISM: Artificial Sequence
<220> FEATURE:
<223> OTHER INFORMATION: oligoDNA primer

<400> SEQUENCE: 8
ggcgtgggtg tagaatgaca gccaccc                                         27

<210> SEQ ID NO 9
<211> LENGTH: 26
<212> TYPE: DNA
<213> ORGANISM: Artificial Sequence
<220> FEATURE:
<223> OTHER INFORMATION: oligoDNA primer

<400> SEQUENCE: 9
accacagcag gcttatgcct tggacg                                          26

<210> SEQ ID NO 10
<211> LENGTH: 29
<212> TYPE: DNA
<213> ORGANISM: Artificial Sequence
<220> FEATURE:
<223> OTHER INFORMATION: oligoDNA primer

<400> SEQUENCE: 10
gggatgacat cagcgttccg cgtgaccag                                       29

<210> SEQ ID NO 11
<211> LENGTH: 30
<212> TYPE: DNA
<213> ORGANISM: Artificial Sequence
<220> FEATURE:
<223> OTHER INFORMATION: oligoDNA primer

<400> SEQUENCE: 11
gatcaccata ggcagatgga ccggcactta                                      30
```

```
<210> SEQ ID NO 12
<211> LENGTH: 26
<212> TYPE: DNA
<213> ORGANISM: Artificial Sequence
<220> FEATURE:
<223> OTHER INFORMATION: oligoDNA primer

<400> SEQUENCE: 12
cgcccgaggc ctacctcttc tatatc                                          26

<210> SEQ ID NO 13
<211> LENGTH: 9678
<212> TYPE: DNA
<213> ORGANISM: Hepatitis C virus

<400> SEQUENCE: 13
acctgcccct aatagggggcg acactccgcc atgaatcact cccctgtgag gaactactgt      60
cttcacgcag aaagcgccta gccatggcgt tagtatgagt gtcgtacagc ctccaggccc     120
ccccctcccg ggagagccat agtggtctgc ggaaccggtg agtacaccgg aattgccggg     180
aagactgggt cctttcttgg ataaacccac tctatgcccg gccatttggg cgtgcccccg     240
caagactgct agccgagtag cgttggggttg cgaaaggcct tgtggtactg cctgatagggg     300 tgcttgcgag tgccccggga ggtctcgtag accgtgcacc atgagcacaa atcctaaacc     360
tcaaagaaaa accaaaagaa acacaaaccg ccgcccacag gacgttaagt tcccgggtgg     420
cggtcagatc gttggcggag tttacttgct gccgcgcagg ggccccaggt tgggtgtgcg     480
cgcgacaagg aagacttctg agcgatccca gccgcgtgga cgacgccagc ccatcccgaa     540
agatcggcgc tccaccggca gtcctgggga aaagccagga tatccttggc ccctgtacgg     600
aaacgagggt tgcggctggg cgggttggcc cctgtccccc cgcgggtctc gtcctacttg     660
gggccccacc gaccccggc atagatcacg caatttgggc agagtcatcg ataccattac     720
gtgtggtttt gccgacctca tgggtacat cctgtcgtt ggcgccccgg ttggaggcgt     780
cgccagagct ctggcacacg gtgttagggt cctggaggac gggataaatt acgcaacagg     840
gaatttaccc ggttgctctt tttctatctt tttgcttgct cttctgtcat gcgtcacagt     900
gccagtgtct gcagtggaag tcaggaacat tagttctagc tactacgcca ctaatgattg     960
ctcaaacaac agcatcacct ggcagctcac tgacgcagtt ctccatcttc ctggatgcgt    1020
cccatgtgag aatgataatg gcaccttgca ttgctggata caagtaacac ccaacgtggc    1080
tgtgaaacac cgcggtgcgc tcactcgtag cctgcgaaca cacgtcgaca tgatcgtaat    1140
ggcagctacg gcctgctcgg ccttgtatgt gggagatgtg tgcggggccg tgatgattct    1200
atcgcaggct ttcatggtat caccacaacg ccacaacttc acccaagagt gcaactgttc    1260
catctaccaa ggtcacatca ccggccatcg catggcatgg gacatgatgc tgaactggtc    1320
tccaactctt gccatgatcc tcgcctacgc gctcgtgtt cccgagatgg tcctcgaaat    1380
tattttcggc ggccattggg gtgtggtgtt tggcttggcc tacttctcca tgcaaggagc    1440
gtgggccaaa gtcattgcca tcctccttct tgttgcggga gtggatgcaa ccacctattc    1500
cagcggccag gaagcgggtc gtaccgtctt ggggttcact aacctctta cttctggtgc    1560 caagcagaac ctctatttaa tcaacaccaa tggcagctgg cacataaacc ggactgccct    1620
caattgcaat gacagcttac agacgggttt catggcttcc ctgttttaca cccacaggtt    1680
caacagctct ggctgccccg agcgcttgtc ttcctgccgc gggctggacg atttttcgcat    1740 cggctgggga accttggaat acgaaaccca cgtcaccaac gatgaggaca tgaggccgta    1800
ctgctggcat taccctccga ggccttgcgg catcgtcccg gctagaacgg tttgcggacc    1860
```

```
ggtctattgt ttcacccta gccctgttgt cgtgggcacc actgacaagc agggcgtacc    1920
cacctacacc tggggggaaa acgagaccga tgtcttcctg ctgaatagca caagacccc     1980 gcgaggagct tggttcggct gcacttggat gaacgggact gggttcacta agacatgcgg   2040
tgcaccacct tgccgcatta ggaaagacta caacagcact atcgatttat tgtgccccac   2100
agactgtttt aggaagcacc ccgatgctac ctatcttaag tgtggagcag gccttggtt    2160 aactcccagg tgcctggtag actacccta tagactgtgg cattatccgt gcactgtaaa    2220
cttcaccatc tttaaggcgc ggatgtatgt aggaggggtg gagcatcgat tctccgcagc   2280
atgcaacttc acgcgcggag atcgctgcag actggaagat agggataggg gtcagcagag   2340
tccactgctg cattccacta ctgagtgggc ggtgctccca tgctccttct ctgacctacc   2400
agcactatcc actggcctat tgcacctcca ccaaaacatc gtggacgtgc agtacctta    2460 cggactttct ccggctctga caagatacat cgtgaagtgg gagtgggtga tcctcctttt   2520
cttgttgttg gcagacgcca ggatctgtgc atgcctttgg atgctcatca tactgggcca   2580
agccgaagcg gcgcttgaga agctcatcat cttgcactcc gctagtgctg ctagtgccaa   2640
tggtccgctg tggtttttca tcttctttac agcggcctgg tacttaaagg gcagggtggt   2700
ccccgtggcc acgtactctg ttctcggctt atggtccttc ctcctcctag tcctggcctt   2760
accacagcag gcttatgcct tggacgctgc tgaacaaggg gaactggggc tggccatatt   2820
agtaattata tccatcttta ctcttacccc agcatacaag atcctcctga ccgttcagt    2880 gtggtggctg tcctacatgc tggtcttggc cgaggcccag attcagcaat gggttccccc   2940
cctggaggtc cgagggggc gtgacggaat catctgggtg gctgtcattc tacacccacg    3000
ccttgtgttt gaggtcacga aatggttgtt agcaatcctg gggcctgcct acctccttaa   3060
agcgtctctg ctacggatac cgtactttgt gagggcccac gctttgctac gagtgtgtac   3120
cctggtgaaa cacctcgcgg gggctaggta catccagatg ctgttgatca ccataggcag   3180
atggaccggc acttacatct acgaccacct ctccccttta tcaacttggg cggcccaggg   3240
tttgcgggac ctggcaatcg ccgtggagcc tgtggtgttc agcccaatgg agaagaaggt   3300
cattgtgtgg ggggctgaga cagtggcgtg tggagacatc ctgcatggcc tcccggtctc   3360
cgcgaggcta ggtagggagg ttctgctcgg ccctgccgac ggctacacct ccaaggggtg   3420
gaagctccta gctcccatca ctgcttatgc ccagcaaaca cgaggcctcc tgggcgccat   3480
agtggtgagt atgacggggc gtgacaggac agaacaggcc ggggaagtcc aaatcctgtc   3540
cacagtctct cagtccttcc tcggaacaac catctcgggg gttttgtgga ctgtttacca   3600
cggagctggc aacaagactc tagccggctt acggggtccg gtcacgcaga tgtactcgag   3660
tgctgagggg gacttggtag gctggcccag ccccctggg accaagtctt ggagccgtg    3720 caagtgtgga gccgtcgacc tatatctggt cacgcggaac gctgatgtca tcccggctcg   3780
gagacgcggg gacaagcggg gagcattgct ctccccgaga cccatttcga ccttgaaggg   3840
gtcctcgggg gggccggtgc tctgccctag gggccacgtc gttgggctct tccgagcagc   3900
tgtgtgctct cggggcgtgg ccaaatccat cgatttcatc cccgttgaga cactcgacgt   3960
tgttacaagg tctcccactt tcagtgacaa cagcacgcca ccggctgtgc cccagaccta   4020
tcaggtcggg tacttgcatg ctccaactgg cagtggaaag agcaccaagg tccctgtcgc   4080
gtatgccgcc caggggtaca agtactagt gcttaacccc tcggtagctg ccaccctggg   4140
gtttggggcg tacctatcca aggcacatgg catcaatccc aacattagga ctggagtcag   4200
gaccgtgatg accggggagg ccatcacgta ctccacatat ggcaaatttc tcgccgatgg   4260
```

```
gggctgcgct agcggcgcct atgacatcat catatgcgat gaatgccacg ctgtggatgc   4320
tacctccatt ctcggcatcg aacggtcct tgatcaagca gagacagccg gggtcagact    4380
aactgtgctg gctacggcca cacccccgg gtcagtgaca acccccatc ccgatataga    4440 agaggtaggc ctcgggcagg agggtgagat cccttctat ggagggcga ttccctatc     4500 ctgcatcaag ggagggagac acctgatttt ctgccactca agaaaaagt gtgacgagct   4560 cgcggcggcc cttcggggca tgggcttgaa tgccgtggca tactatagag ggttggacgt   4620
ctccataata ccagctcagg gagatgtggt ggtcgtcgcc accgacgccc tcatgacggg   4680
gtacactgga gactttgact ccgtgatcga ctgcaatgta gcggtcaccc aagctgtcga   4740
cttcagcctg gaccccacct tcactataac cacacagact gtcccacaag acgctgtctc   4800
acgcagtcag cgccgcgggc gcacaggtag aggaagacag ggcacttata ggtatgtttc   4860
cactggtgaa cgagcctcag gaatgtttga cagtgtagtg ctttgtgagt gctacgacgc   4920
aggggctgcg tggtacgatc tcacaccagc ggagaccacc gtcaggctta gagcgtattt   4980
caacacgccc ggcctacccg tgtgtcaaga ccatcttgaa ttttgggagg cagttttcac   5040
cggcctcaca cacatagacg cccacttcct ctcccaaaca aagcaagcgg gggagaactt   5100
cgcgtaccta gtagcctacc aagctacggt gtgcgccaga gccaaggccc ctcccccgtc   5160 ctggacgcc atgtgaagt gcctggcccg actcaagcct acgcttgcgg gccccacacc    5220
tctcctgtac cgtttgggcc ctattaccaa tgaggtcacc ctcacacacc ctgggacgaa   5280
gtacatcgcc acatgcatgc aagctgacct tgaggtcatg accagcacgt gggtcctagc   5340
tggaggagtc ctggcagccg tcgccgcata ttgcctggcg actggatgcg tttccatcat   5400
cggccgcttg cacgtcaacc agcgagtcgt cgttgcgccg gataaggagg tcctgtatga   5460
ggcttttgat gagatggagg aatgcgcctc tagggcggct ctcatcgaag aggggcagcg   5520
gatagccgag atgttgaagt ccaagatcca aggcttgctg cagcaggcct ctaagcaggc   5580
ccaggacata caacccgcta tgcaggcttc atggcccaaa gtggaacaat tttgggccag   5640
acacatgtgg aacttcatta gcggcatcca atacctcgca ggattgtcaa cactgccagg   5700
gaaccccgcg gtggcttcca tgatggcatt cagtgccgcc ctcaccagtc cgttgtcgac   5760
cagtaccacc atccttctca acatcatggg aggctggtta gcgtcccaga tcgcaccacc   5820
cgcgggggcc accggctttg tcgtcagtgg cctggtgggg gctgccgtgg gcagcatagg   5880
cctgggtaag gtgctggtgg acatcctggc aggatatggt gcgggcattt cggggccct   5940 cgtcgcattc aagatcatgt ctggcgagaa gccctctatg gaagatgtca tcaatctact   6000
gcctgggatc ctgtctccgg gagccctggt ggtgggggtc atctgcgcgg ccattctgcg   6060
ccgccacgtg gaccgggggg agggcgcggt ccaatggatg aacaggctta ttgcctttgc   6120
ttccagagga aaccacgtcg cccctactca ctacgtgacg gagtcggatg cgtcgcagcg   6180
tgtgacccaa ctacttggct ctcttactat aaccagccta ctcagaagac tccacaattg   6240
gataactgag gactgcccca tcccatgctc cggatcctgg ctccgcgacg tgtgggactg   6300
ggtttgcacc atcttgacag acttcaaaaa ttggctgacc tctaaattgt tccccaagct   6360
gcccggcctc cccttcatct cttgtcaaaa ggggtacaag ggtgtgtggg ccggcactgg   6420
catcatgacc acgcgctgcc cttgcggcgc caacatctct ggcaatgtcc gcctgggctc   6480
tatgaggatc acagggccta aaacctgcat gaacacctgg cagggaccct ttcctatcaa   6540
ttgctacacg gagggccagt gcgcgccgaa acccccacg aactacaaga ccgccatctg    6600
gagggtggcg gcctcggagt acgcggaggt gacgcagcat gggtcgtact cctatgtaac   6660
```

-continued

```
aggactgacc actgacaatc tgaaaattcc ttgccaacta ccttctccag agttttctc    6720
ctgggtggac ggtgtgcaga tccataggtt tgcacccaca ccaaagccgt ttttccggga    6780
tgaggtctcg ttctgcgttg ggcttaattc ctatgctgtc gggtcccagc ttccctgtga    6840
acctgagccc gacgcagacg tattgaggtc catgctaaca gatccgcccc acatcacggc    6900
ggagactgcg gcgcggcgct tggcacgggg atcacctcca tctgaggcga gctcctcagt    6960
gagccagcta tcagcaccgt cgctgcgggc cacctgcacc acccacagca acacctatga    7020
cgtggacatg gtcgatgcca acctgctcat ggagggcggt gtggctcaga cagagcctga    7080
gtccaggtg cccgttctgg actttctcga gccaatggcc gaggaagaga gcgaccttga     7140
gccctcaata ccatcggagt gcatgctccc caggagcggg tttccacggg ccttaccggc    7200
ttgggcacgg cctgactaca acccgccgct cgtggaatcg tggaggaggc cagattacca    7260
accgccacc gttgctggtt gtgctctccc ccccccaag aaggcccga cgcctccccc       7320
aaggagacgc cggacagtgg gtctgagcga gagcaccata tcagaagccc tccagcaact    7380
ggccatcaag acctttggcc agcccccctc gagcggtgat gcaggctcgt ccacggggc     7440
gggcgccgcc gaatccggcg gtccgacgtc ccctggtgag ccggcccct cagagacagg    7500
ttccgcctcc tctatgcccc ccctcgaggg ggagcctgga gatccggacc tggagtctga    7560
tcaggtagag cttcaacctc ccccccaggg ggggggggta gctcccggtt cgggctcggg    7620
gtcttggtct acttgctccg aggaggacga taccaccgtg tgctgctcca tgtcatactc    7680
ctggaccggg gctctaataa ctccctgtag ccccgaagag gaaagttgc caatcaaccc     7740
tttgagtaac tcgctgttgc gataccataa caaggtgtac tgtacaacat caaagagcgc    7800
ctcacagagg gctaaaaagg taacttttga caggacgcaa gtgctcgacg cccattatga    7860
ctcagtctta aaggacatca agctagcggc ttccaaggtc agcgcaaggc tcctcacctt    7920
ggaggaggcg tgccagttga ctccacccca ttctgcaaga tccaagtatg gattcggggc    7980
caaggaggtc cgcagcttgt ccgggaggc cgttaaccac atcaagtccg tgtggaagga    8040
cctcctggaa gacccacaaa caccaattcc cacaaccatc atggccaaaa atgaggtgtt    8100
ctgcgtggac cccgccaagg ggggtaagaa accagctcgc ctcatcgttt accctgacct    8160
cggcgtccgg gtctgcgaga aaatggccct ctatgacatt acacaaaagc ttcctcaggc    8220
ggtaatggga gcttcctatg gcttccagta ctcccctgcc caacgggtgg agtatctctt    8280
gaaagcatgg gcggaaaaga aggaccccat gggtttttcg tatgataccc gatgcttcga    8340
ctcaaccgtc actgagagag acatcaggac cgaggagtcc atataccagg cctgctccct    8400
gcccgaggag gcccgcactg ccatacactc gctgactgag agactttacg taggagggcc    8460
catgttcaac agcaagggtc aaacctgcgg ttacagacgt tgccgcgcca gcggggtgct    8520
aaccactagc atgggtaaca ccatcacatg ctatgtgaaa gccctagcgg cctgcaaggc    8580
tgcggggata gttgcgccca caatgctggt atgcggcgat gacctagtag tcatctcaga    8640
aagccagggg actgaggagg acgagcggaa cctgagagcc ttcacggagg ccatgaccag    8700
gtactctgcc cctcctggtg atcccccag accggaatat gacctggagc taataacatc     8760
ctgttcctca aatgtgtctg tggcgttggg cccgcgggc cgccgcagat actacctgac    8820
cagagaccca accactccac tcgcccgggc tgcctgggaa acagttagac actcccctat    8880
caattcatgg ctgggaaaca tcatccagta tgctccaacc atatgggttc gcatggtcct    8940
aatgacacac ttcttctcca ttctcatggt ccaagacacc ctggaccaga acctcaactt    9000
tgagatgtat ggatcagtat actccgtgaa tccttggac cttccagcca taattgagag     9060
```

-continued

```
gttacacggg cttgacgcct tttctatgca cacatactct caccacgaac tgacgcgggt    9120
ggcttcagcc ctcagaaaac ttggggcgcc acccctcagg gtgtggaaga gtcgggctcg    9180
cgcagtcagg gcgtccctca tctcccgtgg agggaaagcg gccgtttgcg gccgatatct    9240
cttcaattgg gcggtgaaga ccaagctcaa actcactcca ttgccggagg cgcgcctact    9300
ggacttatcc agttggttca ccgtcggcgc cggcggggc gacatttttc acagcgtgtc    9360
gcgcgcccga ccccgctcat tactcttcgg cctactccta cttttcgtag gggtaggcct    9420
cttcctactc cccgctcggt agagcggcac acactaggta cactccatag ctaactgttc    9480
cttttttttt tttttttttt tttttttttt tttttttttt tttcttttt ttttttttc    9540 cctctttctt cccttctcat cttattctac tttcttctt ggtggctcca tcttagccct    9600
agtcacggct agctgtgaaa ggtccgtgag ccgcatgact gcagagagtg ccgtaactgg    9660
tctctctgca gatcatgt                                                  9678
```

<210> SEQ ID NO 14
<211> LENGTH: 3033
<212> TYPE: PRT
<213> ORGANISM: Hepatitis C virus

<400> SEQUENCE: 14

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Thr Trp Gly Pro Thr Asp Pro
            100                 105                 110

Arg His Arg Ser Arg Asn Leu Gly Arg Val Ile Asp Thr Ile Thr Cys
        115                 120                 125

Gly Phe Ala Asp Leu Met Gly Tyr Ile Pro Val Val Gly Ala Pro Val
    130                 135                 140

Gly Gly Val Ala Arg Ala Leu Ala His Gly Arg Val Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Val Thr Val Pro Val Ser Ala Val
            180                 185                 190

Glu Val Arg Asn Ile Ser Ser Ser Tyr Tyr Ala Thr Asn Asp Cys Ser
        195                 200                 205

Asn Asn Ser Ile Thr Trp Gln Leu Thr Asp Ala Val Leu His Leu Pro
    210                 215                 220

Gly Cys Val Pro Cys Glu Asn Asp Asn Gly Thr Leu His Cys Trp Ile
225                 230                 235                 240

Gln Val Thr Pro Asn Val Ala Val Lys His Arg Gly Ala Leu Thr Arg
                245                 250                 255

Ser Leu Arg Thr His Val Asp Met Ile Val Met Ala Ala Thr Ala Cys
            260                 265                 270
```

```
Ser Ala Leu Tyr Val Gly Asp Val Cys Gly Ala Val Met Ile Leu Ser
        275                 280                 285

Gln Ala Phe Met Val Ser Pro Gln Arg His Asn Phe Thr Gln Glu Cys
    290                 295                 300

Asn Cys Ser Ile Tyr Gln Gly His Ile Thr Gly His Arg Met Ala Trp
305                 310                 315                 320

Asp Met Met Leu Asn Trp Ser Pro Thr Leu Ala Met Ile Leu Ala Tyr
                325                 330                 335

Ala Ala Arg Val Pro Glu Met Val Leu Glu Ile Ile Phe Gly Gly His
                340                 345                 350

Trp Gly Val Val Phe Gly Leu Ala Tyr Phe Ser Met Gln Gly Ala Trp
        355                 360                 365

Ala Lys Val Ile Ala Ile Leu Leu Val Ala Gly Val Asp Ala Thr
    370                 375                 380

Thr Tyr Ser Ser Gly Gln Glu Ala Gly Arg Thr Val Leu Gly Phe Thr
385                 390                 395                 400

Asn Leu Phe Thr Ser Gly Ala Lys Gln Asn Leu Tyr Leu Ile Asn Thr
                405                 410                 415

Asn Gly Ser Trp His Ile Asn Arg Thr Ala Leu Asn Cys Asn Asp Ser
                420                 425                 430

Leu Gln Thr Gly Phe Met Ala Ser Leu Phe Tyr Thr His Arg Phe Asn
                435                 440                 445

Ser Ser Gly Cys Pro Glu Arg Leu Ser Ser Cys Arg Gly Leu Asp Asp
450                 455                 460

Phe Arg Ile Gly Trp Gly Thr Leu Glu Tyr Glu Thr His Val Thr Asn
465                 470                 475                 480

Asp Glu Asp Met Arg Pro Tyr Cys Trp His Tyr Pro Arg Pro Cys
                485                 490                 495

Gly Ile Val Pro Ala Arg Thr Val Cys Gly Pro Val Tyr Cys Phe Thr
                500                 505                 510

Pro Ser Pro Val Val Gly Thr Thr Asp Lys Gln Gly Val Pro Thr
        515                 520                 525

Tyr Thr Trp Gly Glu Asn Glu Thr Asp Val Phe Leu Leu Asn Ser Thr
    530                 535                 540

Arg Pro Pro Arg Gly Ala Trp Phe Gly Cys Thr Trp Met Asn Gly Thr
545                 550                 555                 560

Gly Phe Thr Lys Thr Cys Gly Ala Pro Pro Cys Arg Ile Arg Lys Asp
                565                 570                 575

Tyr Asn Ser Thr Ile Asp Leu Leu Cys Pro Thr Asp Cys Phe Arg Lys
                580                 585                 590

His Pro Asp Ala Thr Tyr Leu Lys Cys Gly Ala Gly Pro Trp Leu Thr
                595                 600                 605

Pro Arg Cys Leu Val Asp Tyr Pro Tyr Arg Leu Trp His Tyr Pro Cys
    610                 615                 620

Thr Val Asn Phe Thr Ile Phe Lys Ala Arg Met Tyr Val Gly Gly Val
625                 630                 635                 640

Glu His Arg Phe Ser Ala Ala Cys Asn Phe Thr Arg Gly Asp Arg Cys
                645                 650                 655

Arg Leu Glu Asp Arg Asp Arg Gly Gln Gln Ser Pro Leu Leu His Ser
                660                 665                 670

Thr Thr Glu Trp Ala Val Leu Pro Cys Ser Phe Ser Asp Leu Pro Ala
        675                 680                 685

Leu Ser Thr Gly Leu Leu His Leu His Gln Asn Ile Val Asp Val Gln
        690                 695                 700
```

-continued

```
Tyr Leu Tyr Gly Leu Ser Pro Ala Leu Thr Arg Tyr Ile Val Lys Trp
705                 710                 715                 720

Glu Trp Val Ile Leu Leu Phe Leu Leu Leu Ala Asp Ala Arg Ile Cys
                725                 730                 735

Ala Cys Leu Trp Met Leu Ile Ile Leu Gly Gln Ala Glu Ala Ala Leu
            740                 745                 750

Glu Lys Leu Ile Ile Leu His Ser Ala Ser Ala Ala Ser Ala Asn Gly
        755                 760                 765

Pro Leu Trp Phe Phe Ile Phe Phe Thr Ala Ala Trp Tyr Leu Lys Gly
    770                 775                 780

Arg Val Val Pro Val Ala Thr Tyr Ser Val Leu Gly Leu Trp Ser Phe
785                 790                 795                 800

Leu Leu Leu Val Leu Ala Leu Pro Gln Gln Ala Tyr Ala Leu Asp Ala
                805                 810                 815

Ala Glu Gln Gly Glu Leu Gly Leu Ala Ile Leu Val Ile Ile Ser Ile
            820                 825                 830

Phe Thr Leu Thr Pro Ala Tyr Lys Ile Leu Leu Ser Arg Ser Val Trp
        835                 840                 845

Trp Leu Ser Tyr Met Leu Val Leu Ala Glu Ala Gln Ile Gln Gln Trp
    850                 855                 860

Val Pro Pro Leu Glu Val Arg Gly Gly Arg Asp Gly Ile Ile Trp Val
865                 870                 875                 880

Ala Val Ile Leu His Pro Arg Leu Val Phe Glu Val Thr Lys Trp Leu
                885                 890                 895

Leu Ala Ile Leu Gly Pro Ala Tyr Leu Leu Lys Ala Ser Leu Leu Arg
            900                 905                 910

Ile Pro Tyr Phe Val Arg Ala His Ala Leu Leu Arg Val Cys Thr Leu
        915                 920                 925

Val Lys His Leu Ala Gly Ala Arg Tyr Ile Gln Met Leu Leu Ile Thr
    930                 935                 940

Ile Gly Arg Trp Thr Gly Thr Tyr Ile Tyr Asp His Leu Ser Pro Leu
945                 950                 955                 960

Ser Thr Trp Ala Ala Gln Gly Leu Arg Asp Leu Ala Ile Ala Val Glu
                965                 970                 975

Pro Val Val Phe Ser Pro Met Glu Lys Lys Val Ile Val Trp Gly Ala
            980                 985                 990

Glu Thr Val Ala Cys Gly Asp Ile Leu His Gly Leu Pro Val Ser Ala
        995                 1000                1005

Arg Leu Gly Arg Glu Val Leu Leu Gly Pro Ala Asp Gly Tyr Thr
    1010                1015                1020

Ser Lys Gly Trp Lys Leu Leu Ala Pro Ile Thr Ala Tyr Ala Gln
    1025                1030                1035

Gln Thr Arg Gly Leu Leu Gly Ala Ile Val Val Ser Met Thr Gly
    1040                1045                1050

Arg Asp Arg Thr Glu Gln Ala Gly Glu Val Gln Ile Leu Ser Thr
    1055                1060                1065

Val Ser Gln Ser Phe Leu Gly Thr Thr Ile Ser Gly Val Leu Trp
    1070                1075                1080

Thr Val Tyr His Gly Ala Gly Asn Lys Thr Leu Ala Gly Leu Arg
    1085                1090                1095

Gly Pro Val Thr Gln Met Tyr Ser Ser Ala Glu Gly Asp Leu Val
    1100                1105                1110

Gly Trp Pro Ser Pro Pro Gly Thr Lys Ser Leu Glu Pro Cys Lys
    1115                1120                1125
```

-continued

```
Cys Gly Ala Val Asp Leu Tyr Leu Val Thr Arg Asn Ala Asp Val
1130                1135                1140

Ile Pro Ala Arg Arg Gly Asp Lys Arg Gly Ala Leu Leu Ser
1145                1150                1155

Pro Arg Pro Ile Ser Thr Leu Lys Gly Ser Ser Gly Gly Pro Val
1160                1165                1170

Leu Cys Pro Arg Gly His Val Val Gly Leu Phe Arg Ala Ala Val
1175                1180                1185

Cys Ser Arg Gly Val Ala Lys Ser Ile Asp Phe Ile Pro Val Glu
1190                1195                1200

Thr Leu Asp Val Val Thr Arg Ser Pro Thr Phe Ser Asp Asn Ser
1205                1210                1215

Thr Pro Pro Ala Val Pro Gln Thr Tyr Gln Val Gly Tyr Leu His
1220                1225                1230

Ala Pro Thr Gly Ser Gly Lys Ser Thr Lys Val Pro Val Ala Tyr
1235                1240                1245

Ala Ala Gln Gly Tyr Lys Val Leu Val Leu Asn Pro Ser Val Ala
1250                1255                1260

Ala Thr Leu Gly Phe Gly Ala Tyr Leu Ser Lys Ala His Gly Ile
1265                1270                1275

Asn Pro Asn Ile Arg Thr Gly Val Arg Thr Val Met Thr Gly Glu
1280                1285                1290

Ala Ile Thr Tyr Ser Thr Tyr Gly Lys Phe Leu Ala Asp Gly Gly
1295                1300                1305

Cys Ala Ser Gly Ala Tyr Asp Ile Ile Ile Cys Asp Glu Cys His
1310                1315                1320

Ala Val Asp Ala Thr Ser Ile Leu Gly Ile Gly Thr Val Leu Asp
1325                1330                1335

Gln Ala Glu Thr Ala Gly Val Arg Leu Thr Val Leu Ala Thr Ala
1340                1345                1350

Thr Pro Pro Gly Ser Val Thr Thr Pro His Pro Asp Ile Glu Glu
1355                1360                1365

Val Gly Leu Gly Gln Glu Gly Glu Ile Pro Phe Tyr Gly Arg Ala
1370                1375                1380

Ile Pro Leu Ser Cys Ile Lys Gly Gly Arg His Leu Ile Phe Cys
1385                1390                1395

His Ser Lys Lys Lys Cys Asp Glu Leu Ala Ala Ala Leu Arg Gly
1400                1405                1410

Met Gly Leu Asn Ala Val Ala Tyr Tyr Arg Gly Leu Asp Val Ser
1415                1420                1425

Ile Ile Pro Ala Gln Gly Asp Val Val Val Val Ala Thr Asp Ala
1430                1435                1440

Leu Met Thr Gly Tyr Thr Gly Asp Phe Asp Ser Val Ile Asp Cys
1445                1450                1455

Asn Val Ala Val Thr Gln Ala Val Asp Phe Ser Leu Asp Pro Thr
1460                1465                1470

Phe Thr Ile Thr Thr Gln Thr Val Pro Gln Asp Ala Val Ser Arg
1475                1480                1485

Ser Gln Arg Arg Gly Arg Thr Gly Arg Gly Arg Gln Gly Thr Tyr
1490                1495                1500

Arg Tyr Val Ser Thr Gly Glu Arg Ala Ser Gly Met Phe Asp Ser
1505                1510                1515

Val Val Leu Cys Glu Cys Tyr Asp Ala Gly Ala Ala Trp Tyr Asp
1520                1525                1530
```

-continued

Leu Thr Pro Ala Glu Thr Thr Val Arg Leu Arg Ala Tyr Phe Asn
1535                1540                1545

Thr Pro Gly Leu Pro Val Cys Gln Asp His Leu Glu Phe Trp Glu
1550                1555                1560

Ala Val Phe Thr Gly Leu Thr His Ile Asp Ala His Phe Leu Ser
1565                1570                1575

Gln Thr Lys Gln Ala Gly Glu Asn Phe Ala Tyr Leu Val Ala Tyr
1580                1585                1590

Gln Ala Thr Val Cys Ala Arg Ala Lys Ala Pro Pro Pro Ser Trp
1595                1600                1605

Asp Ala Met Trp Lys Cys Leu Ala Arg Leu Lys Pro Thr Leu Ala
1610                1615                1620

Gly Pro Thr Pro Leu Leu Tyr Arg Leu Gly Pro Ile Thr Asn Glu
1625                1630                1635

Val Thr Leu Thr His Pro Gly Thr Lys Tyr Ile Ala Thr Cys Met
1640                1645                1650

Gln Ala Asp Leu Glu Val Met Thr Ser Thr Trp Val Leu Ala Gly
1655                1660                1665

Gly Val Leu Ala Ala Val Ala Ala Tyr Cys Leu Ala Thr Gly Cys
1670                1675                1680

Val Ser Ile Ile Gly Arg Leu His Val Asn Gln Arg Val Val Val
1685                1690                1695

Ala Pro Asp Lys Glu Val Leu Tyr Glu Ala Phe Asp Glu Met Glu
1700                1705                1710

Glu Cys Ala Ser Arg Ala Ala Leu Ile Glu Glu Gly Gln Arg Ile
1715                1720                1725

Ala Glu Met Leu Lys Ser Lys Ile Gln Gly Leu Leu Gln Gln Ala
1730                1735                1740

Ser Lys Gln Ala Gln Asp Ile Gln Pro Ala Met Gln Ala Ser Trp
1745                1750                1755

Pro Lys Val Glu Gln Phe Trp Ala Arg His Met Trp Asn Phe Ile
1760                1765                1770

Ser Gly Ile Gln Tyr Leu Ala Gly Leu Ser Thr Leu Pro Gly Asn
1775                1780                1785

Pro Ala Val Ala Ser Met Met Ala Phe Ser Ala Ala Leu Thr Ser
1790                1795                1800

Pro Leu Ser Thr Ser Thr Thr Ile Leu Leu Asn Ile Met Gly Gly
1805                1810                1815

Trp Leu Ala Ser Gln Ile Ala Pro Pro Ala Gly Ala Thr Gly Phe
1820                1825                1830

Val Val Ser Gly Leu Val Gly Ala Ala Val Gly Ser Ile Gly Leu
1835                1840                1845

Gly Lys Val Leu Val Asp Ile Leu Ala Gly Tyr Gly Ala Gly Ile
1850                1855                1860

Ser Gly Ala Leu Val Ala Phe Lys Ile Met Ser Gly Glu Lys Pro
1865                1870                1875

Ser Met Glu Asp Val Ile Asn Leu Leu Pro Gly Ile Leu Ser Pro
1880                1885                1890

Gly Ala Leu Val Val Gly Val Ile Cys Ala Ala Ile Leu Arg Arg
1895                1900                1905

His Val Gly Pro Gly Glu Gly Ala Val Gln Trp Met Asn Arg Leu
1910                1915                1920

Ile Ala Phe Ala Ser Arg Gly Asn His Val Ala Pro Thr His Tyr
1925                1930                1935

-continued

```
Val Thr Glu Ser Asp Ala Ser Gln Arg Val Thr Gln Leu Leu Gly
    1940                1945                1950

Ser Leu Thr Ile Thr Ser Leu Leu Arg Arg Leu His Asn Trp Ile
    1955                1960                1965

Thr Glu Asp Cys Pro Ile Pro Cys Ser Gly Ser Trp Leu Arg Asp
    1970                1975                1980

Val Trp Asp Trp Val Cys Thr Ile Leu Thr Asp Phe Lys Asn Trp
    1985                1990                1995

Leu Thr Ser Lys Leu Phe Pro Lys Leu Pro Gly Leu Pro Phe Ile
    2000                2005                2010

Ser Cys Gln Lys Gly Tyr Lys Gly Val Trp Ala Gly Thr Gly Ile
    2015                2020                2025

Met Thr Thr Arg Cys Pro Cys Gly Ala Asn Ile Ser Gly Asn Val
    2030                2035                2040

Arg Leu Gly Ser Met Arg Ile Thr Gly Pro Lys Thr Cys Met Asn
    2045                2050                2055

Thr Trp Gln Gly Thr Phe Pro Ile Asn Cys Tyr Thr Glu Gly Gln
    2060                2065                2070

Cys Ala Pro Lys Pro Pro Thr Asn Tyr Lys Thr Ala Ile Trp Arg
    2075                2080                2085

Val Ala Ala Ser Glu Tyr Ala Glu Val Thr Gln His Gly Ser Tyr
    2090                2095                2100

Ser Tyr Val Thr Gly Leu Thr Thr Asp Asn Leu Lys Ile Pro Cys
    2105                2110                2115

Gln Leu Pro Ser Pro Glu Phe Phe Ser Trp Val Asp Gly Val Gln
    2120                2125                2130

Ile His Arg Phe Ala Pro Thr Pro Lys Pro Phe Phe Arg Asp Glu
    2135                2140                2145

Val Ser Phe Cys Val Gly Leu Asn Ser Tyr Ala Val Gly Ser Gln
    2150                2155                2160

Leu Pro Cys Glu Pro Glu Pro Asp Ala Asp Val Leu Arg Ser Met
    2165                2170                2175

Leu Thr Asp Pro Pro His Ile Thr Ala Glu Thr Ala Ala Arg Arg
    2180                2185                2190

Leu Ala Arg Gly Ser Pro Pro Ser Glu Ala Ser Ser Ser Val Ser
    2195                2200                2205

Gln Leu Ser Ala Pro Ser Leu Arg Ala Thr Cys Thr Thr His Ser
    2210                2215                2220

Asn Thr Tyr Asp Val Asp Met Val Asp Ala Asn Leu Leu Met Glu
    2225                2230                2235

Gly Gly Val Ala Gln Thr Glu Pro Glu Ser Arg Val Pro Val Leu
    2240                2245                2250

Asp Phe Leu Glu Pro Met Ala Glu Glu Glu Ser Asp Leu Glu Pro
    2255                2260                2265

Ser Ile Pro Ser Glu Cys Met Leu Pro Arg Ser Gly Phe Pro Arg
    2270                2275                2280

Ala Leu Pro Ala Trp Ala Arg Pro Asp Tyr Asn Pro Pro Leu Val
    2285                2290                2295

Glu Ser Trp Arg Arg Pro Asp Tyr Gln Pro Pro Thr Val Ala Gly
    2300                2305                2310

Cys Ala Leu Pro Pro Pro Lys Lys Ala Pro Thr Pro Pro Pro Arg
    2315                2320                2325

Arg Arg Arg Thr Val Gly Leu Ser Glu Ser Thr Ile Ser Glu Ala
    2330                2335                2340
```

-continued

```
Leu Gln Gln Leu Ala Ile Lys Thr Phe Gly Gln Pro Pro Ser Ser
2345                2350                2355

Gly Asp Ala Gly Ser Ser Thr Gly Ala Gly Ala Ala Glu Ser Gly
2360                2365                2370

Gly Pro Thr Ser Pro Gly Glu Pro Ala Pro Ser Glu Thr Gly Ser
2375                2380                2385

Ala Ser Ser Met Pro Pro Leu Glu Gly Glu Pro Gly Asp Pro Asp
2390                2395                2400

Leu Glu Ser Asp Gln Val Glu Leu Gln Pro Pro Gln Gly Gly
2405                2410                2415

Gly Val Ala Pro Gly Ser Gly Ser Gly Ser Trp Ser Thr Cys Ser
2420                2425                2430

Glu Glu Asp Asp Thr Thr Val Cys Cys Ser Met Ser Tyr Ser Trp
2435                2440                2445

Thr Gly Ala Leu Ile Thr Pro Cys Ser Pro Glu Glu Glu Lys Leu
2450                2455                2460

Pro Ile Asn Pro Leu Ser Asn Ser Leu Leu Arg Tyr His Asn Lys
2465                2470                2475

Val Tyr Cys Thr Thr Ser Lys Ser Ala Ser Gln Arg Ala Lys Lys
2480                2485                2490

Val Thr Phe Asp Arg Thr Gln Val Leu Asp Ala His Tyr Asp Ser
2495                2500                2505

Val Leu Lys Asp Ile Lys Leu Ala Ala Ser Lys Val Ser Ala Arg
2510                2515                2520

Leu Leu Thr Leu Glu Glu Ala Cys Gln Leu Thr Pro Pro His Ser
2525                2530                2535

Ala Arg Ser Lys Tyr Gly Phe Gly Ala Lys Glu Val Arg Ser Leu
2540                2545                2550

Ser Gly Arg Ala Val Asn His Ile Lys Ser Val Trp Lys Asp Leu
2555                2560                2565

Leu Glu Asp Pro Gln Thr Pro Ile Pro Thr Thr Ile Met Ala Lys
2570                2575                2580

Asn Glu Val Phe Cys Val Asp Pro Ala Lys Gly Gly Lys Lys Pro
2585                2590                2595

Ala Arg Leu Ile Val Tyr Pro Asp Leu Gly Val Arg Val Cys Glu
2600                2605                2610

Lys Met Ala Leu Tyr Asp Ile Thr Gln Lys Leu Pro Gln Ala Val
2615                2620                2625

Met Gly Ala Ser Tyr Gly Phe Gln Tyr Ser Pro Ala Gln Arg Val
2630                2635                2640

Glu Tyr Leu Leu Lys Ala Trp Ala Glu Lys Lys Asp Pro Met Gly
2645                2650                2655

Phe Ser Tyr Asp Thr Arg Cys Phe Asp Ser Thr Val Thr Glu Arg
2660                2665                2670

Asp Ile Arg Thr Glu Glu Ser Ile Tyr Gln Ala Cys Ser Leu Pro
2675                2680                2685

Glu Glu Ala Arg Thr Ala Ile His Ser Leu Thr Glu Arg Leu Tyr
2690                2695                2700

Val Gly Gly Pro Met Phe Asn Ser Lys Gly Gln Thr Cys Gly Tyr
2705                2710                2715

Arg Arg Cys Arg Ala Ser Gly Val Leu Thr Thr Ser Met Gly Asn
2720                2725                2730

Thr Ile Thr Cys Tyr Val Lys Ala Leu Ala Ala Cys Lys Ala Ala
2735                2740                2745
```

| | | | | | | | | | | | |
|---|---|---|---|---|---|---|---|---|---|---|---|
| Gly | Ile | Val | Ala | Pro | Thr | Met | Leu | Val | Cys | Gly | Asp | Asp Leu Val |
| | | 2750 | | | | 2755 | | | | 2760 | | |
| Val | Ile | Ser | Glu | Ser | Gln | Gly | Thr | Glu | Glu | Asp | Glu | Arg Asn Leu |
| | | 2765 | | | | 2770 | | | | 2775 | | |
| Arg | Ala | Phe | Thr | Glu | Ala | Met | Thr | Arg | Tyr | Ser | Ala | Pro Pro Gly |
| | | 2780 | | | | 2785 | | | | 2790 | | |
| Asp | Pro | Pro | Arg | Pro | Glu | Tyr | Asp | Leu | Glu | Leu | Ile | Thr Ser Cys |
| | | 2795 | | | | 2800 | | | | 2805 | | |
| Ser | Ser | Asn | Val | Ser | Val | Ala | Leu | Gly | Pro | Arg | Gly | Arg Arg Arg |
| | | 2810 | | | | 2815 | | | | 2820 | | |
| Tyr | Tyr | Leu | Thr | Arg | Asp | Pro | Thr | Thr | Pro | Leu | Ala | Arg Ala Ala |
| | | 2825 | | | | 2830 | | | | 2835 | | |
| Trp | Glu | Thr | Val | Arg | His | Ser | Pro | Ile | Asn | Ser | Trp | Leu Gly Asn |
| | | 2840 | | | | 2845 | | | | 2850 | | |
| Ile | Ile | Gln | Tyr | Ala | Pro | Thr | Ile | Trp | Val | Arg | Met | Val Leu Met |
| | | 2855 | | | | 2860 | | | | 2865 | | |
| Thr | His | Phe | Phe | Ser | Ile | Leu | Met | Val | Gln | Asp | Thr | Leu Asp Gln |
| | | 2870 | | | | 2875 | | | | 2880 | | |
| Asn | Leu | Asn | Phe | Glu | Met | Tyr | Gly | Ser | Val | Tyr | Ser | Val Asn Pro |
| | | 2885 | | | | 2890 | | | | 2895 | | |
| Leu | Asp | Leu | Pro | Ala | Ile | Ile | Glu | Arg | Leu | His | Gly | Leu Asp Ala |
| | | 2900 | | | | 2905 | | | | 2910 | | |
| Phe | Ser | Met | His | Thr | Tyr | Ser | His | His | Glu | Leu | Thr | Arg Val Ala |
| | | 2915 | | | | 2920 | | | | 2925 | | |
| Ser | Ala | Leu | Arg | Lys | Leu | Gly | Ala | Pro | Pro | Leu | Arg | Val Trp Lys |
| | | 2930 | | | | 2935 | | | | 2940 | | |
| Ser | Arg | Ala | Arg | Ala | Val | Arg | Ala | Ser | Leu | Ile | Ser | Arg Gly Gly |
| | | 2945 | | | | 2950 | | | | 2955 | | |
| Lys | Ala | Ala | Val | Cys | Gly | Arg | Tyr | Leu | Phe | Asn | Trp | Ala Val Lys |
| | | 2960 | | | | 2965 | | | | 2970 | | |
| Thr | Lys | Leu | Lys | Leu | Thr | Pro | Leu | Pro | Glu | Ala | Arg | Leu Leu Asp |
| | | 2975 | | | | 2980 | | | | 2985 | | |
| Leu | Ser | Ser | Trp | Phe | Thr | Val | Gly | Ala | Gly | Gly | Gly | Asp Ile Phe |
| | | 2990 | | | | 2995 | | | | 3000 | | |
| His | Ser | Val | Ser | Arg | Ala | Arg | Pro | Arg | Ser | Leu | Leu | Phe Gly Leu |
| | | 3005 | | | | 3010 | | | | 3015 | | |
| Leu | Leu | Leu | Phe | Val | Gly | Val | Gly | Leu | Phe | Leu | Leu | Pro Ala Arg |
| | | 3020 | | | | 3025 | | | | 3030 | | |

EFFICIENT CELL CULTURE SYSTEM FOR HEPATITIS C VIRUS GENOTYPE 2B

CROSS-REFERENCE TO RELATED APPLICATIONS

The present application is a National Stage application of International Patent Application No PCT/DK2009/050189, filed Jul. 24, 2009, which is incorporated herein by reference in its entirety and which claims the benefit of European Application No. EP 08162466.0, filed Aug. 15, 2008.

INCORPORATION OF SEQUENCE LISTING

A computer readable form of the Sequence Listing named "66146_94676_SEQ_LST.txt" and which is 81153 bytes in size, is electronically filed herewith and herein incorporated by reference in its entirety. This Sequence Listing consists of SEQ ID NOs: 1-14.

FIELD OF THE INVENTION

The present invention provides infectious recombinant hepatitis C genotype 2 viruses (HCV), and vectors, cells and animals comprising the same. The present invention provides methods of producing the infectious recombinant HCV genotype 2, and their use in identifying anti-HCV therapeutics including use in vaccines and diagnostics, as well as sequences of HCV associated with HCV pathogenesis.

BACKGROUND

Hepatitis C is one of the most widespread infectious diseases in the world. About 180 million people are infected with hepatitis C virus (HCV) worldwide with a yearly incidence of 3-4 million. While the acute phase of infection is mostly asymptomatic, the majority of acutely infected individuals develops chronic hepatitis and is at increased risk of developing liver cirrhosis and hepatocellular carcinoma. Thus, HCV infection is a major contributor to end-stage liver disease and in developed countries to liver transplantation.

HCV is a small, enveloped virus classified as a member of the Flaviviridae family. Its genome consists of a 9.6 kb single stranded RNA of positive polarity composed of 5' and 3' untranslated regions (UTR) and one long open reading frame (ORF) encoding a polyprotein, which is co- and post-translationally cleaved and thus yields the structural (Core, E1, E2), p7 and nonstructural (NS2, NS3, NS4A, NS4B, NS5A, NS5B) proteins.

HCV isolates from around the world exhibit significant genetic heterogeneity. At least 6 major HCV genotypes (genotypes 1-6) have been identified, which differ by 31-33% at the nucleotide level and deduced amino acid level. In addition, there are numerous subtypes (a, b, c, etc.), which differ by 20-25% on the nucleotide and deduced amino acid level.

While HCV genotypes 1-3 predominate in the Western World, genotypes 4-6 are more common in areas with high prevalence or even endemic levels of HCV infection. Subtypes 1b and 2b have a significant prevalence in the Western world.

While the only approved treatment for chronic HCV infection, combination therapy with interferon-α and ribavirin, leads to a sustained virologic response in most of genotype 2 or 3 patients, viral clearance is only obtained for about half of patients with genotype 1 or 4. There is no vaccine against HCV.

Since its discovery in 1989, research on HCV has been hampered by the lack of appropriate cell culture systems allowing for research on the complete viral life cycle as well as new therapeutics and vaccines.

In 2001, a genotype 2a isolate (JFH1) was described (Kato et al., 2001), which yielded high RNA titers in the replicon system without adaptive mutations (Kato et al., 2003).

A major breakthrough occurred in 2005, when formation of infectious viral particles was reported after transfection of RNA transcripts from the JFH1 full-length consensus cDNA clone into Huh7 cells (Wakita et al., 2005) (Zhong et al., 2005).

At the same time, Lindenbach et al. demonstrated that the intragenotypic 2a/2a recombinant genome (J6/JFH1), in which the structural genes (C, E1, E2), p7 and NS2 of JFH1 were replaced by the respective genes of clone J6CF, produced infectious viral particles in Huh7.5 cells (a cell line derived from bulk Huh7 cells) with an accelerated kinetic (Lindenbach et al., 2005). Cell culture derived J6/JFH viruses were apparently fully viable in vivo.

Despite the importance of the described cell culture systems they represent only a single subtype (genotype 2a) of HCV. It is important to develop cell culture systems for representative strains of other HCV genotypes, since neutralizing antibodies are not expected to cross-neutralize all genotypes and new specific antiviral compounds might have differential efficiencies against different genotypes. For the genotype specific study of the function of the structural proteins, p7 and NS2 as well as related therapeutics such as neutralizing antibodies, fusion inhibitors, ion-channel blockers and protease inhibitors, it would be sufficient to construct intergenotypic recombinant viruses in analogy to J6/JFH.

Pietschmann et al. 2006 disclose construction and characterization of infectious intra- and intergenotypic hepatitis C virus recombinants. The authors created a series of recombinant genomes allowing production of infectious genotype 1a, 1b, 2a and 3a particles by constructing intra- and intergenotypic recombinant genomes between the JFH1 isolate and the HCV isolates: H77 (genotype 1a), Con1 (genotype 1b), J6 (genotype 2a) and 452 (genotype 3a) respectively. Thus, disclosing genotype subtypes completely different from the genotype disclosed in the present application.

The infectious titers of the 1a, 1b and 3a genotypes disclosed in Pietschmann et al. 2006 are not at a level sufficiently high for practical utilization in functional analysis, drug and vaccine development or other applications. For such applications, including screening of potential drugs and development of potential vaccine candidates, the skilled person will know that infectivity titers below $10^3$ TCID50/mL contain insufficient amounts of infectious virus.

Accordingly, the study does not attempt cell culture adaptation of the genotype recombinants, e.g. by serial passage of cell culture derived viruses to naïve cells and it is not investigated whether adaptive mutations develop after transfection in cell culture. In fact, Pietschmann et al does not even provide any sequence data of the virus produced in the cell culture.

SUMMARY OF INVENTION

In this study, the present inventors used the J8 reference isolates (genotype 2b) to construct a viable, JFH1-based genome. The present inventors passaged J8/JFH1 virus in cell culture and obtained both high infectivity titers, high HCV RNA titers and identified one putative adaptive mutation.

The present inventors have developed robust cell culture systems for HCV genotype 2b. This is an important advance for the study of HCV, since it permits detailed molecular studies of HCV and enhances the potential for developing broadly reactive reagents against HCV, including but not limited to small molecule drugs, antibodies and vaccines. Accordingly, the present invention may be used for individualised treatment of patients infected with genotype 2b.

In one aspect the present invention relates to a replicating RNA comprising the structural genes (Core, E1, E2), p7 and the non-structural gene NS2 of genotype 2b and the non-structural genes NS3, NS4A, NS4B, NS5A and NS5B from the JFH1 strain.

In another aspect the present invention pertains to an isolated nucleic acid molecule which encodes human hepatitis C virus of genotype 2b/JFH1, wherein said molecule is capable of expressing said virus when transfected into cells.

In yet another aspect the present invention pertains to a composition comprising a nucleic acid molecule according to the present invention, a cassette vector for cloning viral genomes, methods for producing a cell which replicates HCV 2b/JFH1 RNA and cells obtainable there from.

In another aspect the present invention pertains to methods for producing a hepatitis C virus particle, methods for in vitro producing a hepatitis C virus-infected cell.

In a further aspect the present invention pertains to methods for screening an anti-hepatitis C virus substance, hepatitis C vaccines comprising a hepatitis C virus particle, methods for producing a hepatitis C virus vaccine and antibodies against hepatitis C virus.

DETAILED DESCRIPTION

The present invention advantageously provides hepatitis C virus (HCV) nucleotide sequences capable of replication, expression of functional HCV proteins, and infection in vivo and in vitro for development of antiviral therapeutics and diagnostics.

Nucleic Acid Molecules (cDNA Clones and RNA Transcripts)

In a broad aspect, the present invention is directed to a genetically engineered hepatitis C virus (HCV) encoded by nucleic acid sequences such as a complementary DNA (cDNA) sequence and replicating RNA (J8/JFH1) comprising the structural genes (Core, E1, E2), p7 and the non-structural gene NS2 of genotype 2b (e.g. strain J8) and the non-structural genes NS3, NS4A, NS4B, NS5A and NS5B from the JFH1 strain (genotype 2a, genbank accession number AB047639).

Thus in one embodiment, the present invention relates to a replicating RNA comprising the structural genes (Core, E1, E2), p7 and the non-structural gene NS2 of genotype 2b and the non-structural genes NS3, NS4A, NS4B, NS5A and NS5B from the JFH1 strain.

In another embodiment the genotype 2b is of the strain J8.

The invention provides an isolated nucleic acid molecule encoding an infectious recombinant HCV genome, which nucleic acids comprise an intergenotypic HCV genome. In one embodiment, the intergenotypic HCV genome comprises sequences encoding structural genes (Core, E1, E2), p7 and nonstructural genes (NS2) from a first HCV strain, and sequences encoding the 5' untranslated region (UTR), non-structural genes NS3, NS4A, NS4B, NS5A, NS5B, and the 3' UTR from a second HCV strain.

In one embodiment, the first HCV strain and the second HCV strain are from different genotypes.

In one embodiment, the first HCV strain is strain J8, and in another embodiment, the second HCV strain is strain JFH1.

In one embodiment, the HCV nucleic acid molecule of the present invention comprises the nucleic acid sequence (cDNA) of J8/JFH1, SEQ ID NO: 1. In another embodiment the nucleic acid molecule has at least a functional portion of a sequence as shown in SEQ ID NO: 1 which represents a specific embodiment of the present invention exemplified herein.

In yet an embodiment the nucleic acid molecule comprises the nucleic acid sequence with a sequence identity of at least 90% to that of SEQ ID NO: 1.

In another embodiment, the nucleic acid comprises a sequence sharing at least 90% identity with that set forth in SEQ ID NO: 1, such as 90% identity, 91% identity, 92% identity, 93% identity, 94% identity, 95% identity, 96% identity, 97% identity, 98% identity, or 99% identity.

As commonly defined "identity" is here defined as sequence identity between genes or proteins at the nucleotide or amino acid level, respectively. Thus, in the present context "sequence identity" is a measure of identity between proteins at the amino acid level and a measure of identity between nucleic acids at nucleotide level. The protein sequence identity may be determined by comparing the amino acid sequence in a given position in each sequence when the sequences are aligned. Similarly, the nucleic acid sequence identity may be determined by comparing the nucleotide sequence in a given position in each sequence when the sequences are aligned.

To determine the percent identity of two amino acid sequences or of two nucleic acids, the sequences are aligned for optimal comparison purposes (e.g., gaps may be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

One may manually align the sequences and count the number of identical amino acids. Alternatively, alignment of two sequences for the determination of percent identity may be accomplished using a mathematical algorithm. Such an algorithm is incorporated into the NBLAST and XBLAST programs of (Altschul et al. 1990). BLAST nucleotide searches may be performed with the NBLAST program, score=100, wordlength=12, to obtain nucleotide sequences homologous to a nucleic acid molecules of the invention. BLAST protein searches may be performed with the XBLAST program, score=50, wordlength=3 to obtain amino acid sequences homologous to a protein molecule of the invention. To obtain gapped alignments for comparison purposes, Gapped BLAST may be utilised. Alternatively, PSI-Blast may be used to perform an iterated search which detects distant relationships between molecules. When utilising the NBLAST, XBLAST, and Gapped BLAST programs, the default parameters of the respective programs may be used. See www.ncbi.nlm.nih.gov. Alternatively, sequence identity may be calculated after the sequences have been aligned e.g. by the BLAST program in the EMBL database (www.ncbi.nlm.gov/cgi-bin/BLAST). Generally, the default settings with respect to e.g. "scoring matrix" and "gap penalty" may be used for alignment. In the context of the present invention, the BLASTN and PSI BLAST default settings may be advantageous.

The percent identity between two sequences may be determined using techniques similar to those described above, with or without allowing gaps. In calculating percent identity, only exact matches are counted.

It should be noted that while SEQ ID NO: 1 is a DNA sequence, the present invention contemplates the corresponding RNA sequence, and DNA and RNA complementary sequences as well.

In a further embodiment, a region from an HCV isolate is substituted for a corresponding region, e.g., of an HCV nucleic acid having a sequence of SEQ ID NO: 1.

In another embodiment, the HCV nucleic acid is a DNA that codes on expression or after in vitro transcription for a replication-competent HCV RNA genome, or is itself a replication-competent HCV RNA genome.

In one embodiment, the HCV nucleic acid of the invention has a full-length sequence as depicted in or corresponding to SEQ ID NO: 1. Various modifications for example of the 5' and 3' UTR are also contemplated by the invention. In another embodiment, the nucleic acid further comprises a reporter gene, which, in one embodiment, is a gene encoding neomycin phosphotransferase, Renilla luciferase, secreted alkaline phosphatase (SEAP), Gaussia luciferase or the green fluorescent protein.

Naturally, as noted above, the HCV nucleic acid sequence of the invention is selected from the group consisting of double stranded DNA, positive-sense cDNA, or negative-sense cDNA, or positive-sense RNA or negative-sense RNA or double stranded RNA. Thus, where particular sequences of nucleic acids of the invention are set forth, both DNA and corresponding RNA are intended, including positive and negative strands thereof.

In a further embodiment, the nucleic acid sequence of SEQ ID NO: 1 or the said nucleic acid sequence with or without any mutation described in this document is obtained by any other means than what is described above.

In another embodiment, the complementary DNA (cDNA) provided by the present invention encodes human hepatitis C virus of genotype 2b/JFH1, wherein said molecule is capable of expressing said virus when transfected into cells and further capable of infectivity in vivo and wherein said molecule encodes the amino acid sequence of J8/JFH1, SEQ ID NO: 2.

According to various aspects of the invention, HCV nucleic acid, including the polyprotein coding region, can be mutated or engineered to produce variants or derivatives with, e.g., silent mutations, conservative mutations, etc. In a further preferred aspect, silent nucleotide changes in the polyprotein coding regions (i.e., variations of the first, second or third base of a codon leading to a new codon that encodes the same amino acid) are incorporated as markers of specific HCV clones.

Thus, one aspect of the present invention relates to any of the amino acid sequences disclosed herein, such as but not limited to SEQ ID NO: 2.

In yet an embodiment the isolated nucleic acid molecule encodes the amino acid sequence with a sequence identity of at least 90% to that of SEQ ID NO: 2.

In another embodiment, the amino acid sequences comprises a sequence sharing at least 90% identity with that set forth in SEQ ID NO: 2, such as 90% identity, 91% identity, 92% identity, 93% identity, 94% identity, 95% identity, 96% identity, 97% identity, 98% identity, or 99% identity.

It is to be understood that a sequence identity of at least 90%, such as 90% identity, 91% identity, 92% identity, 93% identity, 94% identity, 95% identity, 96% identity, 97% identity, 98% identity, or 99% identity applies to all sequences disclosed in the present application.

Nucleic acid molecules according to the present invention may be inserted in a plasmid vector for translation of the corresponding HCV RNA. Thus, the HCV DNA may comprise a promoter 5' of the 5'-UTR on positive-sense DNA, whereby transcription of template DNA from the promoter produces replication-competent RNA. The promoter can be selected from the group consisting of a eukaryotic promoter, yeast promoter, plant promoter, bacterial promoter, or viral promoter.

In one embodiment the present invention provides a cassette vector for cloning viral genomes, comprising, inserted therein, the nucleic acid sequence according to the invention and having an active promoter upstream thereof.

Adaptive Mutations

Adapted mutants of a HCV-cDNA construct or HCV-RNA full-length genome with improved abilities to generate infectious viral particles in cell culture compared to the original HCV-cDNA construct or the original HCV-RNA full-length genome are characterized in that they are obtainable by a method in which the type and number of mutations in a cell culture adapted HCV-RNA genome are determined through sequence analysis and sequence comparison and these mutations are introduced into a HCV-cDNA construct, particularly a HCV-cDNA construct according to the present invention, or into an (isolated) HCV-RNA full-length genome, either by site-directed mutagenesis, or by exchange of DNA fragments containing the relevant mutations.

In contrast to JFH1-based intergenotypic recombinants of genotypes 1a, 1b, 3a, 4a, 5a and 6a (Gottwein et al. 2007, Scheel et al. 2008, Jensen et al. in press, Gottwein et al. unpublished results), viability and efficient growth of J8/JFH1 apparently does not depend on adaptive mutations. The present inventors here report one putative adaptive mutation, which might be advantageous but apparently not necessary for efficient formation and release of viral particles in cell culture, and thus the present invention relates to this adaptive mutations in the present use as well as use in other strains by changing equivalent positions of such genomes to the adapted nucleotide or amino acid described. Efficient growth of J8/JFH1 without adaptive mutations is indeed surprising, however, could be explained by the fact that J8/JFH1 is a recombinant of two different HCV subtypes (2b and 2a) and not two different genotypes. HCV RNA and HCV infectivity titers observed in Huh7.5 cell cultures infected with J8/JFH1 viruses (Table 3 and Table 4) were comparable to those observed in cultures infected with the reference virus J6/JFH1 as well as other JFH1-based intergenotypic recombinants (e.g. genotypes 1a and 6a) developed by the present investigators. However, viability and efficient growth of intergenotypic recombinants of genotypes 1a, 1b, 3a, 4a, 5a and 6a was dependent on adaptive mutations.

The preferred HCV-cDNA construct, HCV-RNA full-length genome with the ability to release viral particles in cell culture, which is consequently highly suitable for practical use, is characterized in that it contains none or the following nucleic acid exchange and/or none or the following amino acid exchange.

Figure 1B:
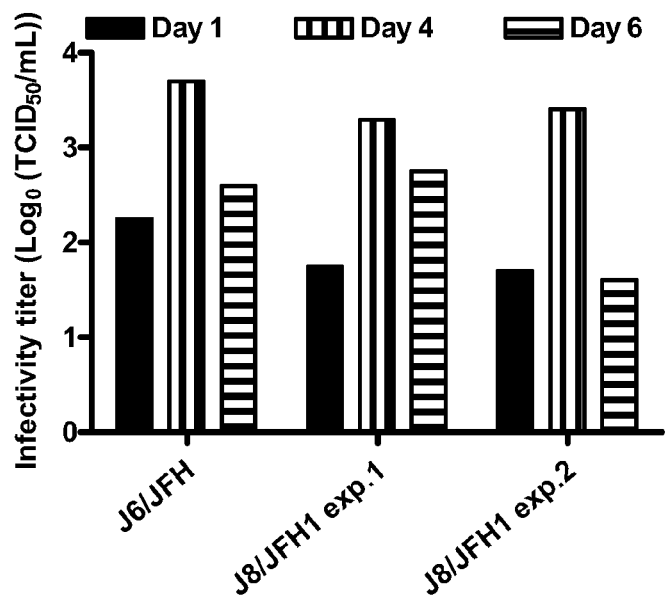

In two independent RNA transfections of Huh7.5 cells, J8/JFH1 spread comparably to J6/JFH with approximately 20% and 80% HCV antigen positive cells on days 1 and 4, respectively (FIG. 1A). The supernatant infectivity titers increased from ~$10^{1.5}$ TCID$_{50}$/mL on day 1 to ~$10^{3.5}$ TCID$_{50}$/mL on day 4 (FIG. 1B). During viral passage (FIG. 1C), HCV RNA and infectivity titers were ~$10^7$ IU/mL (FIG. 1D) and ~$10^{4.5}$ TCID$_{50}$/mL (data not shown; see also Table 3 and 4), respectively. Analysis of recovered viruses (days 10 and 13 post-infection, respectively) showed that J8/JFH1 was genetically stable in two first passages performed from the first transfection (data not shown and exp. 1 in FIGS. 1C and D). In the passage of virus from the second transfection (exp. 2 in FIGS. 1C and D), G4458A (R1373Q) was present as a 50/50 quasispecies with the original sequence (virus from day 13 post-infection).

One embodiment of the present invention relates to adaptive mutations, wherein the adaptive mutation is a mutation that can be observed by clonal or direct sequencing of recovered replicating genomes of SEQ ID NO: 1.

Thus in a further embodiment, the present invention relates to nucleic acid molecules according to the present invention, wherein said molecule comprises none or one adaptive mutations in NS3.

In another embodiment the present invention relates to an isolated nucleic acid molecule which encodes human hepatitis C virus of genotype 2b/JFH1, wherein said molecule is capable of expressing said virus when transfected into cells and wherein said molecule encodes the nucleic acid sequence with a sequence identity of at least 90% to that of SEQ ID NO: 1 and wherein the genotype 2b is strain J8.

In yet an embodiment the present invention relates to an isolated nucleic acid molecule which encodes human hepatitis C virus of genotype 2b/JFH1, wherein said molecule is capable of expressing said virus when transfected into cells and wherein said molecule encodes the nucleic acid sequence with a sequence identity of at least 90% to that of SEQ ID NO: 2 and wherein the genotype 2b is strain J8.

In the context of the present invention the term "adaptive mutation" is meant to cover mutations identified in passaged J8/JFH1 viruses that provide the original J8/JFH1 and any other HCV sequence the ability to grow efficiently in culture. Furthermore all introductions of mutations into the J8/JFH1 sequences described, whether or not yielding better growth abilities, and the introduction of these mutations into any HCV sequence should be considered.

Thus the described mutation enable the HCV-RNA genome (e.g. derived from a HCV-cDNA clone) to form viral particles in and release these from suitable cell lines. In addition the described mutation might change the function of NS3 in favourable ways, which might be exploited in other experimental systems employing these proteins. This also includes other HCV genomes with adaptive mutations, all of them, combinations of them or individual mutations that grow in culture. In this case the titers might be lower than those listed.

One embodiment of the present invention relates to adaptive mutations, wherein said adaptive mutation is a replacement of G in position 4458 of SEQ ID NO: 1 with A as represented in SEQ ID NO: 13.

In another embodiment all the amino acid change observed herein is provided by the present application. The skilled addressee can easily obtain the same amino acid change by mutating another base of the codon and hence all means of obtaining the given amino acid sequence is intended.

An embodiment of the present invention relates to adaptive mutations, wherein said adaptive mutation is a replacement of R in position 1373 of SEQ ID NO: 2 with Q as represented in SEQ ID NO: 14.

Titer

To determine the efficiency of the developed system, HCV RNA titers are determined in IU/ml (international units/ml) with Taq-Man Real-Time-PCR and infectious titers are determined with a 50% tissue culture infectious dose method. This titer shows the dilution of the examined viral stock, at which 50% of the replicate cell cultures used in the essay become infected and is given in TCID50/ml. Alternatively the infectious titers are determined as FFU/ml (focus forming unites/ml) (Table 3 and 4); in this method, infectivity titers are determined by infection of cell culture replicates with serial dilutions of virus containing supernatants and, following immuno-stainings for HCV antigens, counting of HCV-antigen positive cell foci.

HCV RNA titers and infectivity titers can be determined extracellularly, in cell culture supernatant (given as IU and $TCID_{50}$ or FFU per ml, respectively) or intracellularly, in lysates of pelleted cells (given as IU and $TCID_{50}$ or FFU related to a given cell number, which was lysed) (Table 4).

One embodiment of the present invention relates to a nucleic acid molecule of the present invention, wherein said molecule is capable of generating a HCV RNA titer of $10^4$ IU/ml or above following transfection and/or subsequent viral passage, such as a titer of at least $10^5$ IU/mL, such as a titer of at least $10^6$ IU/mL, such as a titer of at least $10^7$ IU/mL, such as a titer of at least $10^8$ IU/mL, such as a titer of at least $10^9$ IU/mL, such as a titer of at least $10^{10}$ IU/mL, such as a titer of at least $10^{11}$ IU/mL, or such as a titer of at least $10^{12}$ IU/mL.

In another embodiment, the present invention relates to a nucleic acid molecule according to the invention, wherein said molecule is capable of generating a HCV infectivity titer of at least $10^2$ $TCID_{50}$/ml or above following transfection and/or subsequent viral passage, such as a titer of at least $10^3$ TCID50/ml, such as a titer of at least $10^4$ $TCID_{50}$/ml, such as a titer of at least $10^5$ $TCID_{50}$/ml, such as a titer of at least $10^6$ $TCID_{50}$/ml, such as a titer of at least $10^7$ $TCID_{50}$/ml, such as a titer of at least $10^8$ $TCID_{50}$/ml, such as a titer of at least $10^9$ $TCID_{50}$/ml or such as a titer of at least $10^{10}$ $TCID_{50}$/ml.

It is of course evident to the skilled addressee that the titers described here are obtained using the assay described in this text. Any similar or equivalent titer determined by any method is thus evidently within the scope of the present invention.

Compositions

One embodiment of the present invention relates to a composition comprising a nucleic acid molecule according to the invention suspended in a suitable amount of a pharmaceutical acceptable diluent or excipient.

In another embodiment, this invention provides for compositions comprising an isolated nucleic acid, vector or cell of this invention, or an isolated nucleic acid obtained via the methods of this invention.

In one embodiment, the term "composition" refers to any such composition suitable for administration to a subject, and such compositions may comprise a pharmaceutically acceptable carrier or diluent, for any of the indications or modes of administration as described. The active materials in the compositions of this invention can be administered by any appropriate route, for example, orally, parenterally, intravenously, intradermally, subcutaneously, or topically, in liquid or solid form.

It is to be understood that any applicable drug delivery system may be used with the compositions and/or agents/vectors/cells/nucleic acids of this invention, for administration to a subject, and is to be considered as part of this invention.

The compositions of the invention can be administered as conventional HCV therapeutics. The compositions of the invention may include more than one active ingredient which interrupts or otherwise alters groove formation, or occupancy by RNA or other cellular host factors, in one embodiment, or replicase components, in another embodiment, or zinc incorporation, in another embodiment.

The precise formulations and modes of administration of the compositions of the invention will depend on the nature of the anti-HCV agent, the condition of the subject, and the judgment of the practitioner. Design of such administration and formulation is routine optimization generally carried out without difficulty by the practitioner.

It is to be understood that any of the methods of this invention, whereby a nucleic acid, vector or cell of this invention is used, may also employ a composition comprising the same as herein described, and is to be considered as part of this invention.

"Pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopoeia or other generally recognized pharmacopoeia for use in animals, and more particularly in humans.

The term "excipient" refers to a diluent, adjuvant, carrier, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The term "adjuvant" refers to a compound or mixture that enhances the immune response to an antigen. An adjuvant can serve as a tissue depot that slowly releases the antigen and also as a lymphoid system activator that non-specifically enhances the immune response. Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (bacille Calmette-Guerin) and Corynebacterium parvmm. Preferably, the adjuvant is pharmaceutically acceptable.

Cells

The nucleotides of the present invention may be used to provide a method for identifying additional cell lines that are permissive for infection with HCV, comprising contacting (e.g. transfecting) a cell line in tissue culture with an infectious amount of HCV RNA of the present invention, e.g., as produced from the plasmid clones, and detecting replication and formation and release of viral particles of HCV in cells of the cell line.

Naturally, the invention extends as well to a method for identifying an animal that is permissive for infection with HCV, comprising introducing an infectious amount of the HCV RNA, e.g., as produced by the plasmids, to the animal, and detecting replication and formation and release of viral particles of HCV in the animal. By providing infectious HCV, e.g. comprising a dominant selectable marker, the invention further provides a method for selecting for HCV with further adaptive mutations that permit higher levels of HCV replication in a permissive cell line or animal comprising contacting (e.g. transfecting) a cell line in culture, or introducing into an animal, an infectious amount of the HCV RNA, and detecting progressively increasing levels of HCV RNA and infectious HCV viral particles in the cell line or the animal.

In a specific embodiment, the adaptive mutation permits modification of HCV tropism. An immediate implication of this aspect of the invention is creation of new valid cell culture and animal models for HCV infection.

The permissive cell lines or animals that are identified using the nucleic acids of the invention are very useful, inter alia, for studying the natural history of HCV infection, isolating functional components of HCV, and for sensitive, fast diagnostic applications, in addition to producing authentic HCV virus or components thereof.

Because the HCV DNA, e.g., plasmid vectors, of the invention encode HCV components, expression of such vectors in a host cell line transfected, transformed, or transduced with the HCV DNA can be effected.

For example, a baculovirus or plant expression system can be used to express HCV virus particles or components thereof. Thus, a host cell line may be selected from the group consisting of a bacterial cell, a yeast cell, a plant cell, an insect cell, and a mammalian cell.

In one embodiment, the cell is a hepatocyte, or in another embodiment, the cell is the Huh-7 hepatoma cell line or a derived cell line such as Huh7.5, Huh7.5.1 cell line.

In one embodiment, the cell, or in another embodiment, cell systems of this invention comprise primary cultures or other, also non hepatic cell lines. "Primary cultures" refers, in one embodiment, to a culture of cells that is directly derived from cells or tissues from an individual, as well as cells derived by passage from these cells, or immortalized cells.

In one embodiment, "cell line" refers to a population of cells capable of continuous or prolonged growth and division in vitro. The term "cell lines" also includes immortalized cells. Often, cell lines are clonal populations derived from a single progenitor cell. Such cell lines are also termed "cell clones". It is further known in the art that spontaneous or induced changes can occur in karyotype during storage or transfer of such clonal populations. Therefore, cells derived from the cell clones referred to may not be precisely identical to the ancestral cells or cultures. According to the present invention, such cell clones may be capable of supporting replication of a vector, virus, viral particle, etc., of this invention, without a significant decrease in their growth properties, and are to be considered as part of this invention.

It is to be understood that any cell of any organism that is susceptible to infection by or propagation of an HCV construct, virus or viral particle of this invention is to be considered as part of this invention, and may be used in any method of this invention, such as for screening or other assays, as described herein.

Thus in one embodiment the present invention relates to a method for producing a cell which replicates HCV 2b/JFH1 RNA and produces a virus particle comprising introducing the said RNA according to the invention into a cell.

In one embodiment the present invention relates to a method for producing a cell, which replicates an RNA comprising the structural genes (Core, E1, E2), p7 and the non-structural gene NS2 of genotype 2b, strain J8, and the non-structural genes NS3, NS4A, NS4B, NS5A and NS5B from the JFH1 strain and produces a virus particle comprising introducing the said RNA into a cell wherein said RNA encodes an amino acid sequence comprising one adaptive mutation, said adaptive mutation is a replacement of R at position 1373 of SEQ ID NO: 2 with Q.

In one embodiment the 2b strain is J8.

Also, a method for in vitro producing a hepatitis C virus-infected cell comprising culturing the cell which produces virus particles of the present invention and infecting other cells with the produced virus particle in the culture.

Naturally, the invention extends to any cell obtainable by such methods, for example any in vitro cell line infected with HCV, wherein the HCV has a genomic RNA sequence as described herein. Such as a hepatitis C virus infected cell obtainable by any of the methods described.

In one embodiment, the cell line is a hepatocyte cell line such as Huh7 or derived cell lines e.g. Huh7.5 or Huh7.5.1.

In another embodiment the cell is Huh7.5.

In another embodiment the cell is any cell expressing the genes necessary for HCV infection and replication, such as but not limited to CD81, SR-BI, Claudin-1, -4, -6 or -9 and the low-density lipid receptor.

Figure 4A:
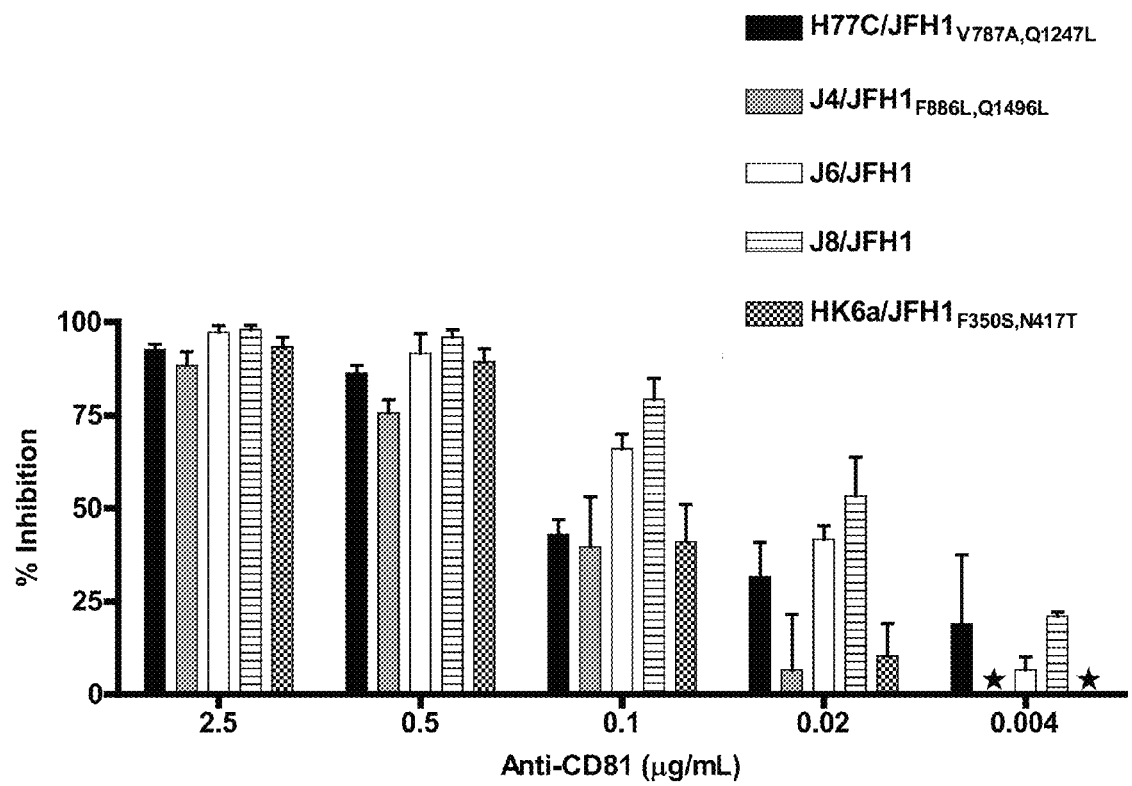

Importance of CD81 for HCV entry has in previous studies been shown for pseudoviral particles (HCVpp) of genotypes 1-6, and for cell culture derived HCV (HCVcc) of genotypes 1a (H77), 1b (Con-1), 3a (S52), 4a (ED43) and 5a (SA13). Blocking of SR-BI receptors was found to inhibit infection with HCVpp of genotypes 1-6. In the HCVcc system, genotypes 2a and 5a in previous studies depended on SR-BI. In comparative studies, the present investigators showed that entry of genotypes 1, 2 and 6 was efficiently inhibited when relative high doses of blocking antibodies against the respective HCV co-receptor were used (FIG. 4). Thus, CD81 and SR-BI play an important role for entry of prototype isolates of the six major genotypes and important subtypes 1b and 2b. Future studies will be required to determine if the different levels of inhibition seen at lower antibody doses are due to stochastical effects or indicate different modes of entry.

The invention further provides various methods for producing HCV virus particles, including by isolating HCV virus particles from the HCV-infected non-human animal of invention; culturing a cell line of the invention under conditions that permit HCV replication and virus particle formation; or culturing a host expression cell line transfected with HCV DNA under conditions that permit expression of HCV particle proteins; and isolating HCV particles or particle proteins from the cell culture. The present invention extends to an HCV virus particle comprising a replication-competent HCV genome RNA, or a replication-defective HCV genome RNA, corresponding to an HCV nucleic acid of the invention as well.

Virus Particle

The production of authentic virus proteins (antigens) may be used for the development and/or evaluation of diagnostics. The cell culture system according to the invention also allows the expression of HCV antigens in cell cultures. In principle these antigens can be used as the basis for diagnostic detection methods.

The production of HCV viruses and virus-like particles, in particular for the development or production of therapeutics and vaccines as well as for diagnostic purposes is an embodiment of the present invention. Especially cell culture adapted complete HCV genomes, which could be produced by using the cell culture system according to the invention, are able to replicate and form viral particles in cell culture with high efficiency. These genomes have the complete functions of HCV and in consequence they are able to produce infectious viruses.

Thus in one embodiment the present invention relates to a method for producing a hepatitis C virus particle of the present invention or parts thereof, comprising culturing a cell or an animal to allow either to produce the virus.

In another embodiment the inventions provides a hepatitis C virus particle obtainable by the method described.

Because the invention provides, inter alia, infectious HCV RNA, the invention provides a method for infecting an animal with HCV which comprises administering an infectious dose of HCV RNA, such as the HCV RNA transcribed from the plasmids described above, to the animal. Naturally, the invention provides a non-human animal infected with HCV of the invention, which non-human animal can be prepared by the foregoing methods.

A further advantage of the present invention is that, by providing a complete functional HCV genome, authentic HCV viral particles or components thereof, which may be produced with native HCV proteins or RNA in a way that is not possible in subunit expression systems, can be prepared.

In addition, since each component of HCV of the invention is functional (thus yielding the authentic HCV), any specific HCV component is an authentic component, i.e., lacking any errors that may, at least in part, affect the clones of the prior art. Indeed, a further advantage of the invention is the ability to generate HCV virus particles or virus particle proteins that are structurally identical to or closely related to natural HCV virions or proteins. Thus, in a further embodiment, the invention provides a method for propagating HCV in vitro comprising culturing a cell line contacted with an infectious amount of HCV RNA of the invention, e.g., HCV RNA translated from the plasmids described above, under conditions that permit replication of the HCV RNA.

Further the viability of the developed viruses may be determined in vivo, either in SCID-uPA mice engrafted with human liver tissue or in chimpanzees as shown in Lindenbach et al. 2006.

In one embodiment, the method further comprises isolating infectious HCV. In another embodiment, the method further comprises freezing aliquots of said infectious HCV. According to this aspect of the invention, and in one embodiment, the HCV is infectious following thawing of said aliquots, and in another embodiment, the HCV is infectious following repeated freeze-thaw cycles of said aliquots.

Screening for anti-viral drugs and the determination of drug resistance.

It can be assumed that resistance to therapy occurs due to the high mutation rate of the HCV genome. This resistance, which is very important for the clinical approval of a substance, can be detected with the cell culture system according to the invention. Cell lines, in which the HCV-RNA construct or the HCV genome or subgenome replicates and produces infectious viral particles, are incubated with increasing concentrations of the relevant substance and the replication of the viral RNA is either determined by means of an introduced reporter gene or through the qualitative or quantitative detection of the viral nucleic acids or proteins. The release of viral particles is determined by measuring HCV RNA and infectivity titers in the cell culture supernatant. Resistance is given if no or a reduced inhibition of the replication and release of viral particles can be observed with the normal concentration of the active substance. The nucleotide and amino acid replacements responsible for the therapy resistance can be determined by recloning the HCV-RNA (for example by the means of RT-PCR) and sequence analysis. By cloning the relevant replacement(s) into the original construct its causality for the resistance to therapy can be proven.

While the replicon systems facilitated testing of drugs interfering with replication such as NS3/4A protease and polymerase inhibitors, the variant genomes obtained in the present invention may prove useful for different research topics. Genomes with the original J8 Core could be applied to examine genotype 2b specific features of Core.

The systems developed in this invention are ideal candidates for genotype 2b specific testing of therapeutics in general and therapeutics targeting viral entry, assembly and release. Genomes with the J8 sequences are valuable for testing of neutralizing antibodies and other drugs acting on entry level, such as fusion inhibitors.

The present inventors conducted cross-genotype neutralization studies in HCV cell culture systems recapitulating the entire viral life cycle using JFH1-based viruses with envelope sequences of all 6 major genotypes and the important subtypes 1b and 2b, which has previously not been possible (Table 2). HCV E1/E2 assembled on HCV pseudo particles (HCVpp), used in previous neutralization studies could show an unphysiological confirmation, glycosylation pattern and/or lipoprotein association due to the nature of the HCVpp as well as the non-hepatic producer cell-lines used in such experiments.

In such studies the viral particles are incubated with the neutralizing substance, e.g. patient derived antibodies present in serum, prior to incubation with cells permissive and susceptible to viral infection. The neutralizing effect, i.e. the inhibitory effect on viral entry, is measured e.g. by relating the number of focus forming units (FFUs, defined as foci of adjacent infected cells) to the equivalent count in a control experiment done under same circumstances without the active inhibitor molecule.

The inventors of the present invention showed that JFH1-based viruses of the genotype 1a, 1b, 2b, 4a, 5a, 6a and 7a were efficiently neutralized by chronic phase H06 genotype 1a serum derived from reference Patient H (Table 2). The results in the cell culture systems compare well to neutralization experiments using Patient H serum from year 26 (H03) carried out in HCVpp systems with envelope proteins of the same prototype isolates of all 6 HCV genotypes as used in the present application, and heterogeneity between the genotypes is thus as previously reported by Meunier et al. 2005.

In addition the present inventors found that cross-genotype neutralization extended to a chronic phase genotype 4a serum (AA), which efficiently neutralized genotype 2b, 4a, 5a, 6a and 7a (Table 2). Also, the cross-genotype neutralization extended to a chronic phase genotype 5a serum (SA3), which efficiently neutralized genotype 2b, 4a, 5a, 6a and 7a (Table 2). It is of note that genotypes subtypes 2a and 2b, which belong to the same genotype and genotypes 2b and 7a, which have, for isolates of different major genotypes, a relatively high sequence homology, differ in their susceptibility to neutralization.

Accordingly, the JFH1-based cell culture systems which have been developed for HCV genotype 1a, 1b, 2a, 2b, 3a, 4a, 5a, 6a and 7a provide a valuable tool for efficiently screening for and identifying new candidate HCV genotype 1a, 1b, 2a, 2b, 3a, 4a, 5a, 6a and 7a inhibitors e.g. of entry e.g. in serum derived from infected patients. Accordingly this invention, allows identification and raise of cross-neutralizing antibodies, which is important for the development of active and passive immunization strategies. Furthermore the availability of cell culture grown HCV particles bearing envelope proteins of the six major genotypes enables the development of inactivated whole virus vaccines and comprehensive virus neutralization studies.

In one embodiment the present invention relates to a method for identifying neutralizing antibodies.

In another embodiment the present invention relates to a method for identifying cross-genotype neutralizing antibodies.

In one embodiment the present invention relates to a method of raising neutralizing antibodies.

In another embodiment the present invention relates to a method of raising cross-neutralizing antibodies.

In one embodiment the present invention related to a method for screening new HCV genotype 1a, 1b, 2a, 2b, 3a, 4a, 5a, 6a and/or 7a inhibitors or neutralizing antibodies, comprising
a) culturing at least one selected from the group consisting of a cell according to the present invention, a hepatitis C virus infected cell according to the present invention and a hepatitis C virus particle obtainable by the present invention together with a hepatitis C virus permissive cell, and
b) subjecting said virus or virus infected cell culture to a blood sample or derivatives thereof from a HCV genotype 1a, 1b, 2a, 2b, 3a, 4a, 5a, 6a and/or 7a infected patient
c) detecting the amount of replicating RNA and/or the virus particles.

The p7 peptide features two transmembrane domains (TM1 and TM2), and p7 monomers multimerize to form a putative ion channel. Additionally p7 has been shown to contain genotype specific sequences required for genotype specific interactions between p7 and other HCV proteins. Hence, new compounds targeting the putative p7 ion-channel and autoprotease inhibitors interfering with NS2, and drugs targeting cellular proteins involved in the described processes can be tested.

Figure 3A:
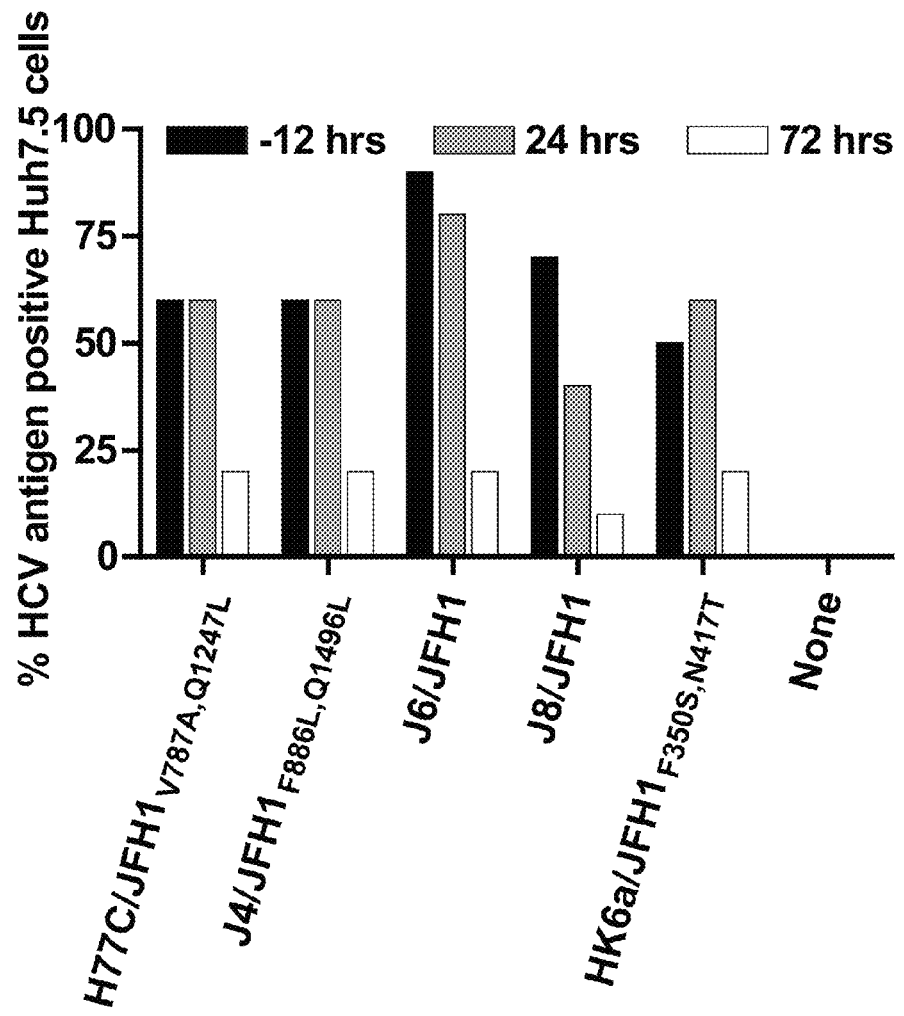
Figure 3B:
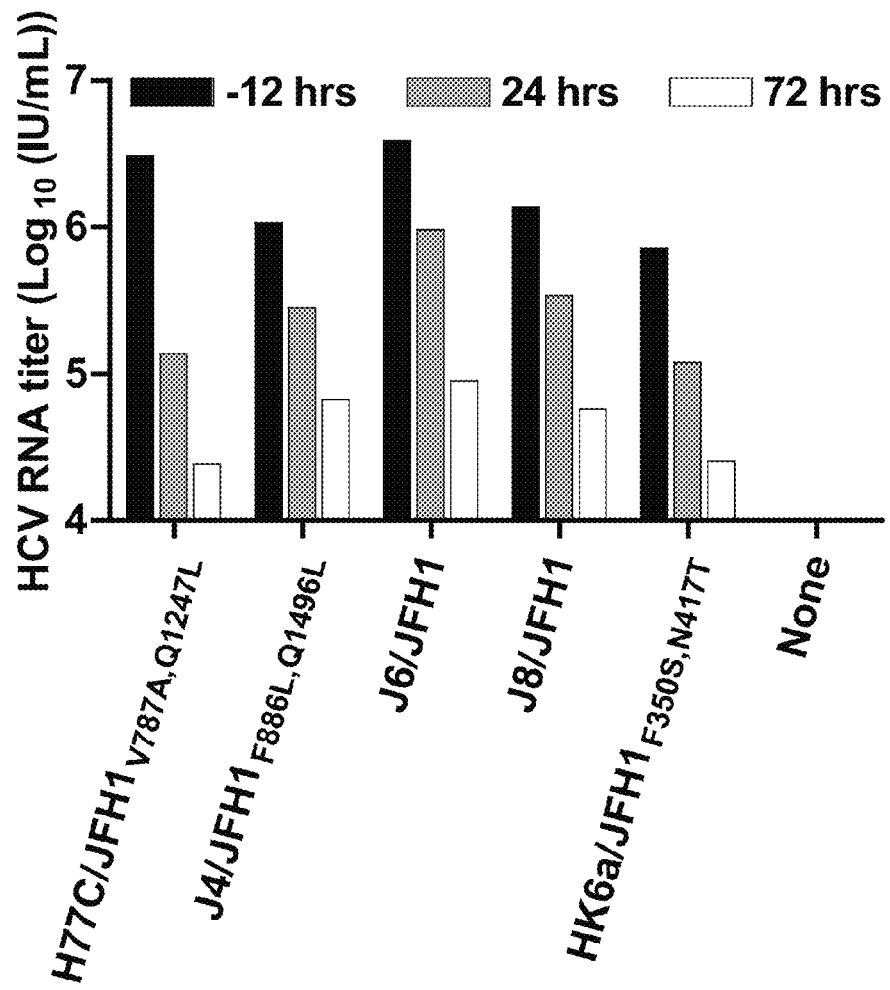
Figure 3C:
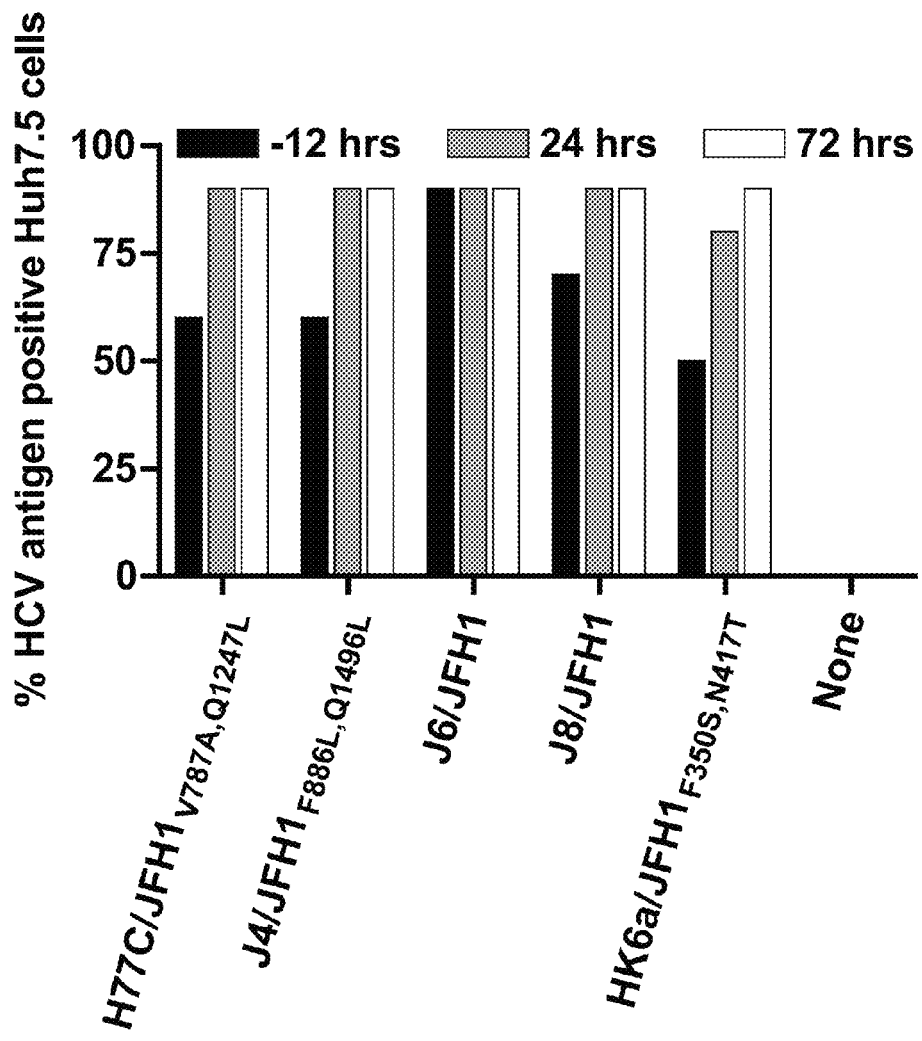
Figure 3D:
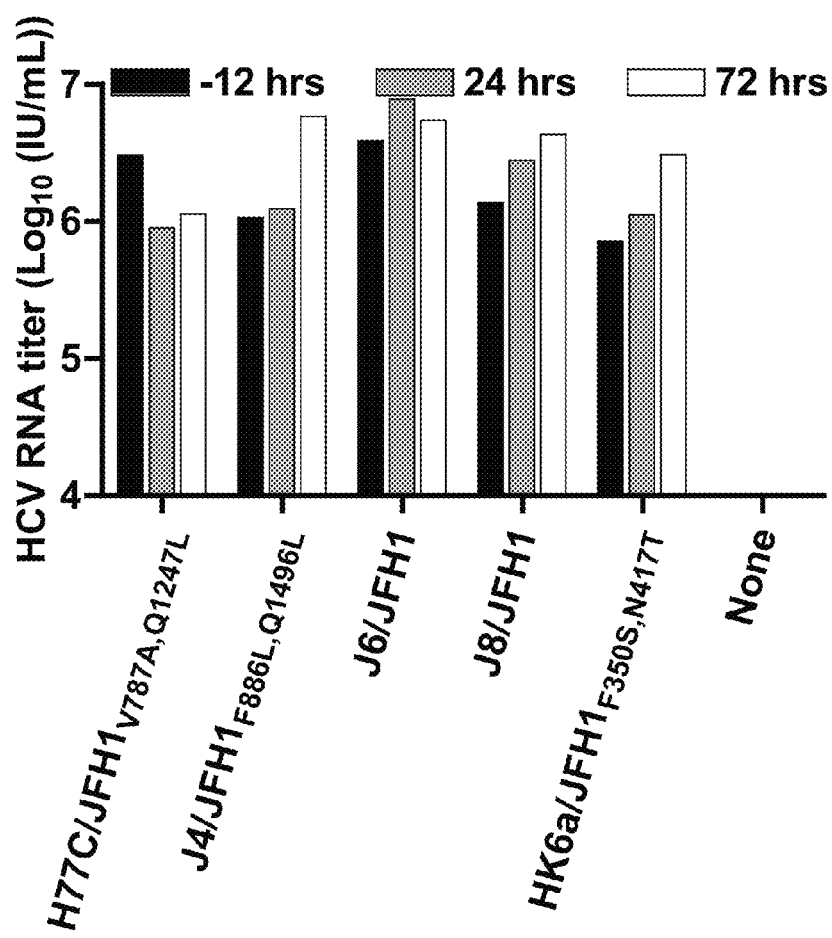
Figure 3E:
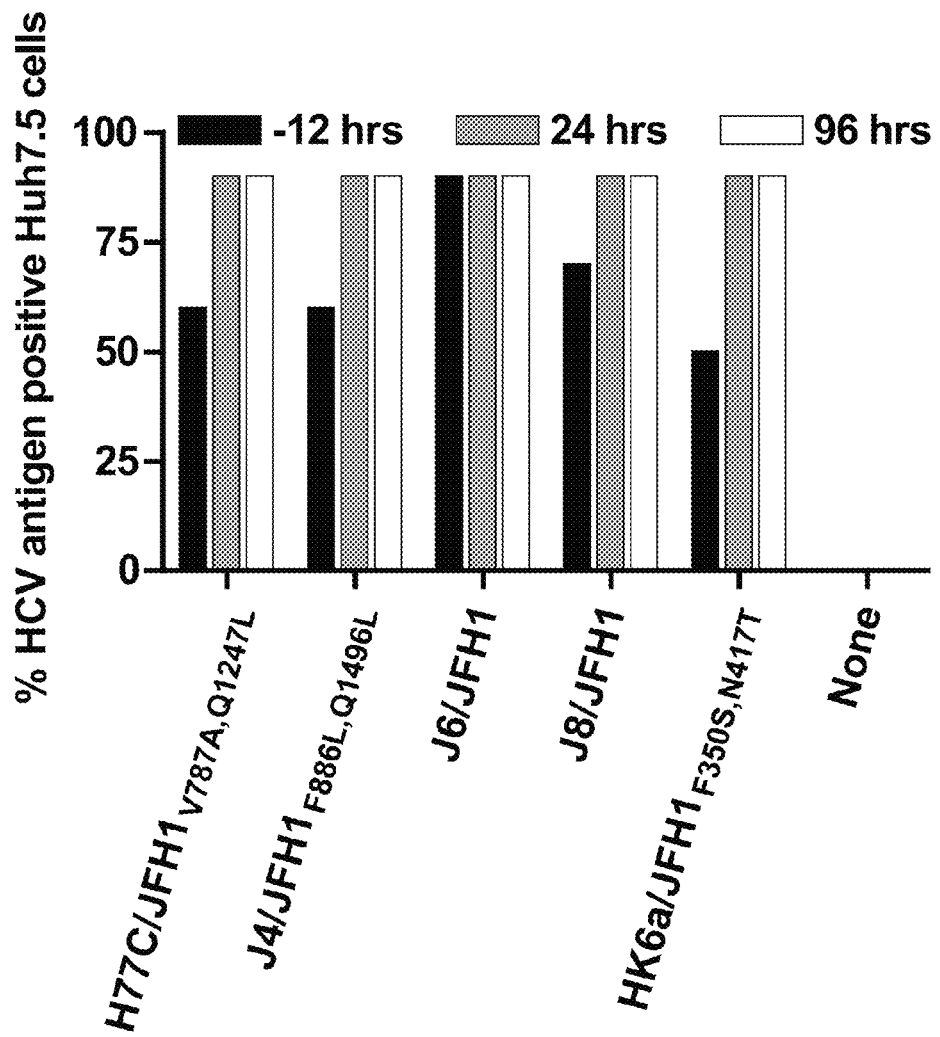
Figure 3F:
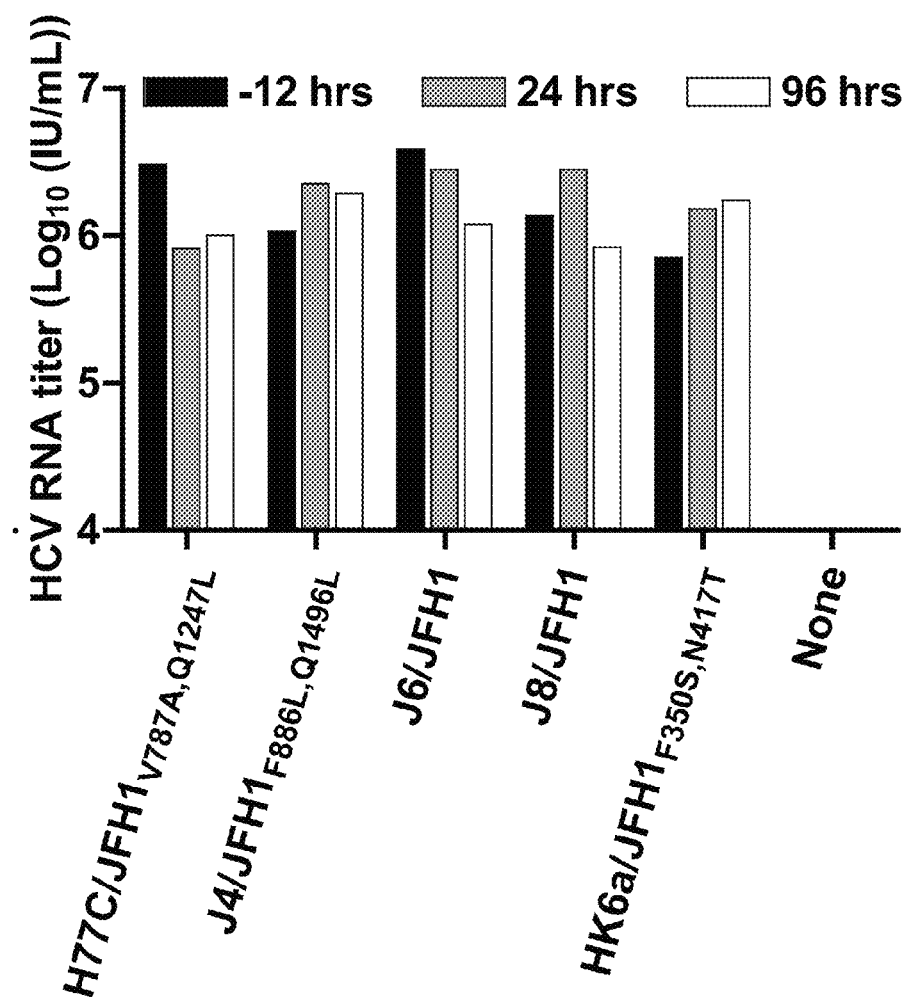

The inventors of the present invention showed that JFH1-based viruses can be used for testing putative anti-HCV antivirals. Huh7.5 cultures infected with JFH1-based recombinants of genotypes 1a, 1b, 2a, 2b, and 6a were treated with 500 IU/mL interferon-α2b (FIG. 3A, B), 20 μM ribavirin (FIG. 3C, D) or 50 μM amantadine (FIG. 3E, F), respectively. A combination of interferon-α2b and ribavirin is the only currently licensed treatment of HCV infected patients. While sustained viral response (SVR) can be achieved in 80-90% of genotype 2 and 3 infected patients treated with this combination therapy, SVR is only seen in 40-50% of genotype 1 and 4 infected patients. Sequence differences of several genome regions, especially E2 and NS5A, are suggested to be responsible for this differential response. The ion-channel blocker amantadine is used in treatment of influenza and has been suggested to block HCV p7. At the tested concentrations, no significant cytotoxic effect was observed. After 72 hrs of interferon-α2b treatment, an >60% decrease in the number of infected cells and a ~2 log decrease in supernatant HCV RNA titers was observed (FIG. 3A, B). Treatment with ribavirin and amantadine had no apparent effect (FIGS. 3C-F). This is in line with previous studies, in which interferon decreased replication of J6/JFH, whereas ribavirin and amantadine did not decrease production of infectious virus in JFH1 cultures or cultures with genotype 1a (H77), 1b (Con1) or 2a (J6) JFH1-based recombinants. Genotype specific susceptibility to interferon-α2 in patients was attributed different genome regions, especially in E2 and NS5A. With the relatively high doses used for treatment of genotype 1-6 infected cultures, we did not observe any genotype specific effect; in future studies, it will be of interest to test different interferon doses and different HCV isolates, preferably from patients showing different responses to interferon. Differential sensitivity to interferon could also be mediated by the UTRs or NS3 to NS5B proteins, which are genotype 2a specific in all the recombinants tested. In conclusion, the developed systems can be applied to test the antiviral potential of known and newly developed therapeutics and to test, which HCV genome regions mediated resistance to treatment.

Thus, one embodiment of the present invention relates to a method for screening an anti-hepatitis C virus substance, comprising
a) culturing at least one selected from the group consisting of a cell according to the present invention, a hepatitis C virus infected cell according to the present invention and a hepatitis C virus particle obtainable by the present invention together with a hepatitis C virus permissive cell,
b) subjecting said virus or virus infected cell culture to the anti-hepatitis C virus substance, and
c) detecting the replicating RNA and/or the virus particles in the resulting culture.

In another embodiment, the inhibition of HCV replication and/or infection and/or pathogenesis includes inhibition of downstream effects of HCV. In one embodiment, downstream effects include neoplastic disease, including, in one embodiment, the development of hepatocellular carcinoma.

In one embodiment, the invention provides a method of screening for anti-HCV therapeutics, the method comprising contacting a cell with an isolated nucleic acid molecule encoding an infectious recombinant HCV genome, comprising a chimeric HCV genome and contacting the cell with a candidate molecule, independently contacting the cell with a placebo and determining the effects of the candidate molecule on HCV infection, replication, or cell-to-cell spread, versus the effects of the placebo, wherein a decrease in the level of HCV infection, replication, or cell-to-cell spread indicates the candidate molecule is an anti-HCV therapeutic.

In one embodiment, the method may be conducted be in vitro or in vivo. In one embodiment, the cells as described may be in an animal model, or a human subject, entered in a clinical trial to evaluate the efficacy of a candidate molecule. In one embodiment, the molecule is labelled for easier detection, including radio-labelled, antibody labelled for fluorescently labelled molecules, which may be detected by any means well known to one skilled in the art.

In one embodiment, the candidate molecule is an antibody.

In one embodiment, the term "antibody" refers to intact molecules as well as functional fragments thereof, such as Fab, F(ab')2, and Fv. In one embodiment, the term "Fab" refers to a fragment, which contains a monovalent antigen-binding fragment of an antibody molecule, and in one embodiment, can be produced by digestion of whole antibody with the enzyme papain to yield an intact light chain and a portion of one heavy chain, or in another embodiment can be obtained by treating whole antibody with pepsin, followed by reduction, to yield an intact light chain and a portion of the heavy chain. In one embodiment, the term "F(ab')2", refers to the fragment of the antibody that can be obtained by treating whole antibody with the enzyme pepsin without subsequent reduction, F(ab')2 is a dimer of two Fab' fragments held together by two disulfide bonds. In another embodiment, the term "Fv" refers to a genetically engineered fragment containing the variable region of the light chain and the variable region of the heavy chain expressed as two chains, and in another embodiment, the term "single chain antibody" or "SCA" refers to a genetically engineered molecule containing the variable region of the light chain and the variable region of the heavy chain, linked by a suitable polypeptide linker as a genetically fused single chain molecule.

Methods of producing these fragments are known in the art.

In another embodiment, the candidate molecule is a small molecule. In one embodiment, the phrase "small molecule" refers to, inter-alia, synthetic organic structures typical of pharmaceuticals, peptides, nucleic acids, peptide nucleic acids, carbohydrates, lipids, and others, as will be appreciated by one skilled in the art. In another embodiment, small molecules, may refer to chemically synthesized peptidomimetics of the 6-mer to 9-mer peptides of the invention.

In another embodiment, the candidate molecule is a nucleic acid. Numerous nucleic acid molecules can be envisioned for use in such applications, including antisense, siRNA, ribozymes, etc., as will be appreciated by one skilled in the art.

It is to be understood that the candidate molecule identified and/or evaluated by the methods of this invention, may be any compound, including, inter-alia, a crystal, protein, peptide or nucleic acid, and may comprise an HCV viral product or derivative thereof, of a cellular product or derivative thereof. The candidate molecule in other embodiments, may be isolated, generated synthetically, obtained via translation of sequences subjected to any mutagenesis technique, or obtained via protein evolution techniques, well known to those skilled in the art, each of which represents an embodiment of this invention, and may be used in the methods of this invention, as well.

In one embodiment, the compound identified in the screening methods as described, may be identified by computer modeling techniques, and others, as described herein. Verification of the activity of these compounds may be accomplished by the methods described herein, where, in one embodiment, the test compound demonstrably affects HCV infection, replication and/or pathogenesis in an assay, as described. In one embodiment, the assay is a cell-based assay, which, in one embodiment, makes use of primary isolates, or in another embodiment, cell lines, etc. In one embodiment, the cell is within a homogenate, or in another embodiment, a tissue slice, or in another embodiment, an organ culture. In one embodiment, the cell or tissue is hepatic in origin, or is a derivative thereof. In another embodiment, the cell is a commonly used mammalian cell line, which has been engineered to express key molecules known to be, or in another embodiment, thought to be involved in HCV infection, replication and/or pathogenesis.

In another embodiment, protein, or in another embodiment, peptide or in another embodiment, other inhibitors of the present invention cause inhibition of infection, replication, or pathogenesis of HCV in vitro or, in another embodiment, in vivo when introduced into a host cell containing the virus, and may exhibit, in another embodiment, an IC50 in the range of from about 0.0001 nM to 100 μM in an in vitro assay for at least one step in infection, replication, or pathogenesis of HCV, more preferably from about 0.0001 nM to 75 μM, more preferably from about 0.0001 nM to 50 μM, more preferably from about 0.0001 nM to 25 μM, more preferably from about 0.0001 nM to 10 μM, and even more preferably from about 0.0001 nM to 1 μM.

In another embodiment, the inhibitors of HCV infection, or in another embodiment, replication, or in another embodiment, pathogenesis, may be used, in another embodiment, in ex vivo scenarios, such as, for example, in routine treatment of blood products wherein a possibility of HCV infection exists, when serology shows a lack of HCV infection.

In another embodiment, the anti-HCV therapeutic compounds identified via any of the methods of the present invention can be further characterized using secondary screens in cell cultures and/or susceptible animal models. In one embodiment, a small animal model may be used, such as, for example, a tree shrew Tupaia belangeri chinensis. In another embodiment, an animal model may make use of a chimpanzee. Test animals may be treated with the candidate compounds that produced the strongest inhibitory effects in any of the assays/methods of this invention. In another embodiment, the animal models provide a platform for pharmacokinetic and toxicology studies.

Vaccines

The construct according to the invention by itself can also be used for various purposes in all its embodiments. This includes the construction of hepatitis C viruses or HCV-like particles and their production in cell cultures as described.

These HCV or HCV-like particles can be used in particular as vaccine. Thus, one embodiment of the present invention relates to a hepatitis C vaccine comprising a hepatitis C virus particle according to the invention or a part thereof.

In another embodiment, the nucleic acids, vectors, viruses, or viral particles may be further engineered to express a heterologous protein, which, in another embodiment, is mammalian or a derivative thereof, which is useful in combating HCV infection or disease progression. Such proteins may comprise cytokines, growth factors, tumor suppressors, or in one embodiment, may following infection, be expressed predominantly or exclusively on an infected cell surface. According to this aspect of the invention, and in one embodiment, such molecules may include costimulatory molecules, which may serve to enhance immune response to infected cells, or preneoplastic cells, or neoplastic cells, which may have become preneoplastic or neoplastic as a result of HCV infection. In one embodiment, the heterologous sequence encoded in the nucleic acids, vectors, viruses, or viral particles of this invention may be involved in enhanced uptake of a nucleic acids, vectors, viruses, or viral particles, and may specifically target receptors thought to mediate HCV infection.

Further, the present invention relates to a method for producing a hepatitis C virus vaccine comprising using a hepatitis C virus particle according to the invention as an antigen, and naturally any antibody against such hepatitis C virus particle.

Uses

The genotype 2b cell culture system developed of the present invention will be a valuable tool to address different research topics. It will allow the genotype specific study of functions of the structural proteins (Core, E1, E2) as well as p7 and NS2 using reverse genetics. While the replicon systems facilitated testing of drugs interfering with replication such as NS3/4A protease and polymerase inhibitors, the system developed in this study is ideal for the genotype 2b specific testing of new drugs, such as drugs interfering with viral entry, such as fusion inhibitors, as well as assembly and release.

Accordingly the genotype 2b developed cell culture systems allows individual patient targeting. This means that when a new potential therapeutic candidate is discovered it is possible to test this particular candidate or combination of candidates on this genotype. Knowing which specific genotype the candidate is functioning towards, it allows an individual treatment of each patient dependent on which specific genotype the patient is infected with. Furthermore these cell culture systems allow the development of antibodies and vaccines targeting individual patients.

In addition new therapeutics targeting the putative p7 ion-channel and protease inhibitors targeting NS2 can be tested specifically for genotype 2b thus allowing individual patient targeting.

J8/JFH1 recombinant viruses will be well suited for screenings for broadly reactive neutralizing antibodies, thus aiding vaccine development.

The replication level of a virus can be determined, in other embodiments, using techniques known in the art, and in other embodiments, as exemplified herein. For example, the genome level can be determined using RT-PCR. To determine the level of a viral protein, one can use techniques including ELISA, immunoprecipitation, immunofluorescence, EIA, RIA, and Western blotting analysis. To determine the replication rate of a virus, one can use the method described in, e.g., Billaud et al., Virology 266 (2000) 180-188.

In one embodiment, the invention provides a method of identifying sequences in HCV associated with HCV pathogenicity, comprising contacting cells with an isolated nucleic acid molecule encoding an infectious recombinant HCV genome, comprising a chimeric HCV genome, contacting cells with an isolated nucleic acid molecule comprising at least one mutation of the chimeric HCV genome, independently culturing the cells and determining HCV infection, replication, or cell-to-cell spread, in cells contacted with the mutant, versus the chimeric HCV, whereby changes in HCV infection, replication, or cell-to-cell spread in cells contacted with the mutant virus shows the mutation is in an HCV sequence associated with HCV pathogenicity.

In one embodiment, the invention provides a method of identifying HCV variants with improved growth in cell culture, the method comprising contacting cells with an isolated nucleic acid molecule encoding an infectious recombinant HCV genome, comprising a chimeric HCV genome contacting cells with an isolated nucleic acid molecule comprising or not comprising mutations of the chimeric HCV genome, independently culturing the cells and determining HCV infection, replication, or cell-to-cell spread, in cells contacted with the chimeric HCV or the mutated virus, whereby enhanced HCV infection, replication, or cell-to-cell spread in cells contacted with the mutated virus shows that the HCV variant has improved growth in cell culture. In some embodiments, HCV variants are selected for enhanced replication, over a long course of time, in vitro culture systems. According to this aspect of the invention, and in some embodiments, cells contacted with the variants are characterized by reduced infection, as compared to cells contacted with the chimeric HCV.

The developed systems can be used to quantify HCV proteins as well as their influence on and interaction with host cell factors. In the present invention, the inventors used confocal microscopy based image analysis to quantify HCV Core and NS5A protein, the amount of intracellular lipids and interaction of Core and NS5A with intracellular lipids. The inventors evaluated spread of in vitro HCV infection by quantitative confocal microscopy based imaging. In a blinded study, increasing amounts of Core and NS5A relative to the number of total cells were detected during days 3-10 for genotype 1, 2 and 6 recombinants (FIG. 2C, D), suggesting that this methodology could be an effective tool to evaluate HCV infection in vitro. The method also readily detected a nonspecific background staining with the anti-Core antibody, whereas the anti-NS5A gave no such signal. Thus, for optimization this quantification method requires attention to the selection of antibodies for immunostaining.

The HCV lifecycle depends on the lipid metabolism and Core has been suspected to induce hepatocellular steatosis in genotype 3 patients. In the present invention, big variation in the lipid content of non-infected Huh7.5 cells was found; during 10 days, infection with genotype 1, 2 and 6 recombinants did not induce intracellular lipid accumulation (FIG. 5), and no genotype specific differences in lipid content were found at peak infection (Table 4). A short-term infection in cell culture might not induce the changes in lipid metabolism leading to steatosis in chronically infected patients. Even though the inventors analyzed an average of 660 cells per culture for each time-point, it is evident that there was variation in the lipid content in infected as well as non-infected cells, which might mask possible subtle differences in lipid content induced by HCV. Furthermore, the inventors based their analysis on quantification of fluorescent intensity to quantify the total amount of lipids in the cell cytoplasm. Thus, morphological differences of lipid droplets between infected and non-infected cells were not analysed, which has been carried out in HCV infected cells by electron microscopy and in HCV Core expressing cells by confocal microscopy.

The present inventors found HCV Core to co-localize with lipid droplets for genotype 1, 2 and 6 recombinants (FIG. 6) as described by others for genotype 2a; further, co-localization of NS5A with lipid droplets was detected for genotype 1, 2 and 6 recombinants (FIG. 6), indicating either a direct or Core-mediated association. Interestingly, the interaction of NS5A with Core was found to play an important role in regulating the early phase of HCV particle formation.

Kits

In a related aspect, the invention also provides a test kit for HCV comprising HCV virus components, and a diagnostic test kit for HCV comprising components derived from an HCV virus as described herein.

Furthermore the invention also provide test kits, for screening for new HCV genotype 2b inhibitors, neutralizing and cross neutralizing antibodies, comprising HCV virus components.

General

Reference to any prior art in this specification is not, and should not be taken as, an acknowledgment or any form of suggestion that this prior art forms part of the common general knowledge in any country.

All patent and non-patent references cited in the present application, are hereby incorporated by reference in their entirety.

As will be apparent, preferred features and characteristics of one aspect of the invention may be applicable to other aspects of the invention. The invention may be embodied in other specific forms without departing from the spirit or essential characteristics thereof. The foregoing embodiments are therefore to be considered in all respects illustrative rather than limiting on the invention described herein. Scope of the invention is thus showed be the appended claims rather than by the foregoing description, and all changes that come within the meaning and range of equivalency of the claims are intended to be embraced by reference therein.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In addition, singular reference does not exclude a plurality. Thus, references to "a", "an", "first", "second" etc. do not preclude a plurality.

The invention may be embodied in other specific forms without departing from the spirit or essential characteristics thereof. The foregoing embodiments are therefore to be considered in all respects illustrative rather than limiting on the invention described herein. Scope of the invention is thus showed be the appended claims rather than by the foregoing description, and all changes that come within the meaning and range of equivalency of the claims are intended to be embraced by reference therein.

The invention will hereinafter be described by way of the following non-limiting Figures and Examples.

| Sequences | | |
|---|---|---|
| SEQ ID NO | DNA/amino acid (AA) | Name |
| SEQ ID NO: 1 | DNA | J8/JFH1 |
| SEQ ID NO: 2 | AA | J8/JFH1 |
| SEQ ID NO: 3 | DNA | -84S_HCV-MOD |
| SEQ ID NO: 4 | DNA | J8 R1458 fus |
| SEQ ID NO: 5 | DNA | J8 F1286 fus |
| SEQ ID NO: 6 | DNA | J8R2309 |
| SEQ ID NO: 7 | DNA | J8F1989 |
| SEQ ID NO: 8 | DNA | J8 R3003 |
| SEQ ID NO: 9 | DNA | J8F2762 |
| SEQ ID NO: 10 | DNA | 3774R_J6 |
| SEQ ID NO: 11 | DNA | J8F3167 |
| SEQ ID NO: 12 | DNA | 4118R_JFH1 |
| SEQ ID NO: 13 | DNA | J8/JFH1(G4458A) |
| SEQ ID NO: 14 | AA | J8/JFH1(G4458A) |

EXAMPLES

Materials and Methods

Source of HCV Genotype 2b

A plasma pool of strain J8 was prepared from acute-phase plasmapheresis units collected from an experimentally infected chimpanzee. This plasma pool has an HCV RNA titer of approximately $10^{4.2}$ IU/ml and an infectivity titer of approximately $10^4$ chimpanzee infectious doses/ml (Engle et al. 2008).

Construction of J8/JFH1 Intergenotypic Recombinant; RNA Extraction, RT-PCR, PCR and Cloning RNA was extracted from plasma and cell culture supernatant using either the High Pure Viral Nucleic Acid Kit (Roche) or the TRIzol (Invitrogen) procedure according to manufacturers protocol. All reverse transcription-polymerase chain reactions (RT-PCR) were carried out using RNA extracted from 100 μL plasma or cell culture supernatant. Primers (TAG Copenhagen) were 1.25 μM and dNTPs (Invitrogen) were 0.5 mM in RT reactions. For denaturation, RNA was incubated for 2' at 65° C. together with primer and dNTPs and placed on ice. cDNA syntheses was done in a 20 μL volume with enzyme and incubation times as described. The final RT reaction was treated with 1-4 U RNase H (Invitrogen) and 1000 U RNase T1 (Ambion) for 20' at 37° C. to degrade RNA. All PCR reactions were done using 2.5 μL cDNA reaction as template in a 50 μL reaction volume. Final concentrations of primer and dNTPs in PCR were 0.2 μM and 0.25 mM respectively. PCR fragments were amplified from the J8 plasma pool with Advantage 2 PCR system (Clontech) and subcloned (Invitrogen, TA-TOPO cloning kits). The J8 Core-NS2 consensus sequence was determined from 4-7 clones. pJ8/JFH1 was constructed by insertion of the EcoRI-AvrII fragment of a fusion product containing JFH1 5'UTR (including EcoRI in pFL-J6/JFH upstream of the HCV sequence), the consensus Core-NS2 sequence of J8, and JFH1 NS3 into pFL-J6/JFH. JFH1 fragments were amplified from pFL-J6/JFH. J8 fragment was amplified from clones derived from the respective plasma pool. Amplification of PCR products for fusion PCR and fusion PCRs were carried out with Pfu Polymerase (Stratagene). Restriction enzymes were purchased from New England Biolabs and ligations were performed using Rapid DNA ligation kit (Roche) according to the protocol. TOP10 chemically competent bacteria (Invitrogen) were used for all bacterial cloning according to the protocol. DNA preparations were carried out using QIAGEN QIAprep spin miniprep kit or QIAfilter plasmid maxi kit (both Qiagen).

In Vitro Transcription

For in vitro transcription 5 μg plasmid was XbaI-linearized (New England Biolabs). Transcription was carried out for 2 hrs with T7 RNA polymerase (Promega) according to protocol. RNA production was evaluated by gel electrophoresis.

Huh7.5 Cell Culture and Generation of Virus Stocks

The human hepatoma cell line Huh7.5 is an INF-α cured clone of the Huh7 hepatoma cell line, with increased HCV replication abilities. Cells were cultured in D-MEM+4500 mg/L Glucose+GlutaMAX-I+Pyruvate (Invitrogen) containing 10% heat inactivated fetal bovine serum (FBS) (Sigma), penicillin at 100 units/ml and streptomycin at 100 mg/ml (Invitrogen) at 5% CO2 and 37° C. Every 2-3 days cells were split after washing with PBS and trypsinizing (Trypsin/EDTA, Invitrogen). Supernatants were sterile filtered to exclude cells and debris and stored at −80° C.

For transfection of HCV RNA transcripts, naïve Huh7.5 cells were plated at $4 \times 10^5$/well in 6-well plates the day before transfection. Prior to transfection 2.5 μg of unpurified RNA transcripts were incubated with Lipofectamine2000 (Invitrogen) in 500 μL Opti-MEM (Invitrogen) for 20' at room temperature. RNA-Lipofectamine2000 transfection complexes were left on cells for 12-24 hrs before washing.

To prove the production of infectious viruses, sterile filtered supernatant from infected cultures was used to infect naïve Huh7.5 cells. Unless other is described, 1 mL supernatant was used for infection of Huh7.5 cells plated in 6-well plates at $4 \times 10^5$/well the day before. Supernatants were left on cells for 3-8 hrs as described in figure and table legends.

Negative controls in transfections were RNA transcripts from replication deficient JFH1-based genomes (with the GND motif); in the kinetic experiment, non-infected cells were used (data not shown).

Viral spread was monitored by HCV Core or NS5A immunostainings with mouse anti-HCV core protein monoclonal antibody (B2) (Anogen, Yes Biotech Laboratories) or anti-NS5A, 9E10, respectively, as described in the following section.

Supernatant infectivity titers were determined as 50% tissue culture infectious dose ($TCID_{50}$)/mL or as focus forming units (FFU)/mL, as described in the following section.

Supernatant HCV RNA titers were measured by a 5' UTR based Real Time RT-PCR as described below.

For analysis of intracellular infectivity and HCV RNA titers, $1 \times 10^5$ cells were pelleted by centrifugation at 500 g for 5 min at 4° C. Pellets were resuspended in complete culture medium and subjected to four freeze/thaw cycles in liquid nitrogen/37° C.; medium was clarified by 2× centrifugation at 1500 g for 5 min and analysed as above.

For generation of virus stocks, Huh7.5 cells were infected at a multiplicity of infection (MOI) of ~0.003. After viral spread to >80% of the culture (Core or NS5A immunostaining), supernatants were filtered, aliquoted and stored at −80° C. Size of each viral stock was ~100 mL.

Immunostainings for HCV Antigens and Lipids; Titration of Infectivity

For staining, cells grown over night on 4- or 8-well chamberslides (Nunc) were washed 2× with PBS and fixed for 5 minutes with acetone. After washing 2× with PBS and 1× with PBS/Tween-20 (0.1%), slides were incubated with 1° antibody (MAB Murine Anti-Human HCV, Core Protein, Clone B2 (Anogen) or anti-NS5A, 9E10 (gift from C. Rice, Rockefeller University) used at 1:200 in PBS containing 5% bovine serum albumine (BSA) for 20' at room temperature. After washing as above, 2° antibody (Alexa Fluor 594 goat anti-mouse IgG (H+L)) and Hoechst33342 (both Invitrogen) for cell nuclei counterstaining, used at 1:500 and 1:10000 dilutions, respectively in PBS/Tween, was added for 5 min. Lipids were stained with oil red O (Fisher scientific) as described previously. Finally, slides were washed with PBS, mounted with Fluoromount-G (Southern Biotech) and cover slipped. Staining was visualized using a Leica TCS SP5 confocal microscope. Percentage of infected cells was evaluated by assigning values of 0% (no cells infected), 1% (or below), 5%, 10-90% in steps of 10, 95% and 100% (all cells infected).

Viral infectivity titers were determined by the tissue culture infectious dose 50 ($TCID_{50}$) or focus forming unit method. $6 \times 10^3$/well naive Huh7.5 cells were plated out in a poly-D-lysine coated 96-well plate (Nunc) the day before infection. Cells were then incubated with 10-fold dilutions of cell culture supernatants. For $TCID_{50}$ determinations, 6 replicates per dilution were incubated for 2-3 days. For FFU determinations, wells were incubated for 48 rs. After incubation, cells were permeabilized for 5' with cold methanol. After washing 1× with PBS and 1× with PBS/Tween-20, blocking was carried out for 20' with sterile filtered 1% BSA/0.2% skim milk in PBS followed by a 5' blocking of endogenous peroxidase activity using 3% H2O2. Cells were washed as above and incubated with a 1:200 dilution of 1° Ab α-NS5A (9E10) in PBS/0.1% tween-20 over night at 4° C. After washing, a 1:300 dilution of 2° Ab HRP-goat anti-mouse IgG (H+L) (Amersham Biosciences) in PBS/0.1% tween-20 was added and incubated for 30' at room temperature. Staining was developed using DAB substrate kit (DAKO) for 30' after washing. In $TCID_{50}$ determinations, wells were scored positive if one or more cells were infected, and the $TCID_{50}$ was calculated according to the Reed and Muench method. $TCID_{50}$ values are derived from single or multiple determinations as indicated. FFU determinations are based on counts of wells with 5-100 FFU and three independent virus dilutions with one replicate each. However, FFU calculations for virus stocks (Table 3) were based on two independent virus dilutions with 6 replicates each.

Real-Time PCR (TaqMan) Assay for Determination of HCV RNA Titers.

Supernatant HCV RNA titers were measured by a 5' UTR based Real Time RT-PCR. RNA was purified from 200 μL of heat inactivated (56° C. for 30') cell culture supernatant and eluted in a final volume of 50 μL using the Total Nucleic Acid Isolation Kit (Roche) in combination with the Total NA Variable Elution Volume protocol on a MagNA Pure LC Instrument (Roche). As an internal control, Phocine Distemper Virus (PDV) was added to the lysis buffer in a concentration titrated to yield a Ct of ~32 upon real-time PCR analysis. In parallel to RNA purified from cell culture supernatants a quantitative HCV standard panel covering RNA concentrations of 0 to $5 \times 10^6$ IU/mL in one-log increments (OptiQuant HCV Panel, AcroMetrix) was analysed. Real-time PCR analyses of HCV and PDV RNA were carried out in two separate reactions using the TaqMan EZ RT-PCR Kit (Applied Biosystems). For HCV, primers and a FAM-labelled MGB-probe were directed against the 5' UTR and were previously shown to perform equivalently against a panel of the six major HCV genotypes in a different TaqMan assay (Engle et al. 2008). For PDV, a ready-to-use primer/probe mix was used (Dr. H. G. M. Niesters, Department of Virology, Erasmus Medical Centre, Rotterdam, The Netherlands). The PCR analysis was performed on a 7500 Real-Time PCR System (Applied Biosystems) using 50° C. for 2', 60° C. for 30' and 95° C. for 5' followed by 45 cycles of 94° C. for 20" and 62° C. for 1'. HCV RNA titers (IU/ml) were calculated using a standard curve created from the known concentrations of the standard panel and their corresponding Ct values. The reproducible detection limit of the assay was 500 IU/ml. In order to confirm successful purification, amplification and the absence of PCR inhibitors, the Ct value of the PDV reaction was compared to the expected Ct value (based on a mean of all previous runs; n>9) using the MedLab QC freeware programme. The results of samples with an actual Ct value within ±2SD of the expected Ct value were accepted.

Confocal Imaging and Quantification

For evaluation of intracellular lipid and HCV antigen content, $5\times10^4$ cells were co-stained with oil red O and anti-HCV Core or NS5A. Image stacks, each comprised of four sections, were collected on a TCS-SP2 confocal microscope (Leica) through either a 40×PL APO (Na=1.25) or a 63×PL APO (Na=1.40) objective for quantification of fluorescence intensity or analysis of co-localization, respectively. Scanning was performed sequentially in 1024×1024 format with a step size of 0.48 µm, with identical settings and avoidance of pixel saturation. The intensity of the oil red O and HCV antigen signals of 6 and 3 image stacks (each containing 110 cells on average), respectively, were quantified per culture using Imaris 6.1.0 software (Bitplane). Fluorescent signals of oil red O and HCV antigen staining was rendered in 3D by constructing an isosurface and subsequently quantifying the total voxel intensity. Quantifications were expressed relative to the number of Hoechst stained nuclei per image stack. For analysis of the percentage of HCV antigen co-localized with lipid (oil red O), thresholds for each channel were set to exclude any background noise. A contour surface was first modulated on regions without cells allowing for masking of channels to be analyzed. At least 20 cells were analyzed per culture. Throughout, all scannings and subsequent image analyses were performed blinded (under code) (see also FIGS. 5-6).

Treatment, Receptor Blocking and Neutralization

For treatment, interferon-α2b (Schering-Plough), ribavirin (Sigma) or amantadine (Sigma) was used; cell viability was monitored with CellTiter 96 AQueous One Solution Cell Proliferation Assay (Promega).

For blocking of CD81 and SR-BI and neutralization assays, Huh7.5 cells were plated $6\times10^3$ per well of a poly-D-lysine-coated 96-well plate and incubated for 24 hrs. For blocking experiments, cells were incubated with anti-CD81 (JS-81; BD Biosciences Pharmingen, Franklin Lakes, N.J.) or isotypematched control antibody (anti-human immunodeficiency virus, p24, clone Kal-1; DAKO) and rabbit polyclonal anti-SR-BI (GeneTex) or rabbit polyclonal control antibody (anti-human Retinoblastoma (Rb) Ab-6, Thermo Scientific), respectively, for 1 hr. Subsequently, cells were infected with ~150 FFU of the respective virus for 3 hrs followed by washing with PBS. After 48 hrs of incubation with normal growth medium, cells were stained for HCV NS5A to determine the number of focus forming units (FFU) per well. Experiments were performed in triplicates unless stated otherwise. Percent inhibition by anti-CD81 and anti-SR-BI was calculated by comparison to the FFU mean of at least 3 replicate wells incubated with virus only.

For neutralization, heat inactivated sera were pre-incubated with ~30-150 FFU for 1 hr at 37° C., preceding 3 hrs incubation on $6\times10^3$ Huh7.5 cells. After 48 hrs incubation with normal growth medium, cultures were immunostained for NS5A, and the number of FFU was determined. Neutralization experiments were performed in triplicates and percent inhibition by patient sera was calculated by comparison to the FFU mean of at least 3 replicate wells incubated with virus only. Sera used for neutralization were derived for from persistently infected Patient H (2006, year 29 after infection, genotype 1a), an Egyptian Patient (AA, 1994, genotype 4a), and a South African hepatocellular carcinoma patient (SA3, genotype 5a).

Sequencing of Cell Culture Derived HCV

Direct sequencing of complete ORF was done to identify adaptive mutations. RNA extraction and reverse transcription was done as described above using 400 U SuperScriptIII (Invitrogen) and RT-primer. 1st round PCR was performed in a 50 µL volume on 2.5 µL of the cDNA reaction using the Advantage 2 PCR Enzyme System (Clontech). Cycle parameters were 5 cycles of 35" at 99° C., 30" at 67° C. and 10' at 68° C., 10 cycles of 35" at 99° C., 30" at 67° C. and 11' at 68° C., 10 cycles of 35" at 99° C., 30" at 67° C. and 12' at 68° C. and 10 cycles of 35" at 99° C., 30" at 67° C. and 13' at 68° C. 12~1 kb products were synthesized in a nested PCR covering the entire ORF Table 1). PCR was set up as above using 2.5 µL of the 1st round PCR for each reaction. Initial denaturation was 35 sec at 99° C. followed by 35 cycles with 35 sec at 99° C., 30 sec at 67° C. and 6 min at 68° C. Genotype 2b specific primers used in $2^{nd}$ round of the long RT-PCR procedure are given in Table 1. PCR products were agarose gel purified and directly sequenced in both directions.

Sequencing, Sequence Analysis and Databases

All sequence reactions was performed at Macrogen Inc., Seoul, South Korea. Sequence analysis was performed with Sequencher 4.7, Gene Codes Corporation and freeware BioEdit v. 7.0.5. HCV sequences used for alignments were retrieved from The European HCV database (euHCVdb; euhcvdb.ibcp.fr/euHCVdb/) and the American HCV database (LANL; hcv.lanl.gov/content/hcv-db/index).

Example 1

Cell Culture Adaptation of Intergenotypic 2b/2a Recombinant (J8/JFH1)

Figure 1C:
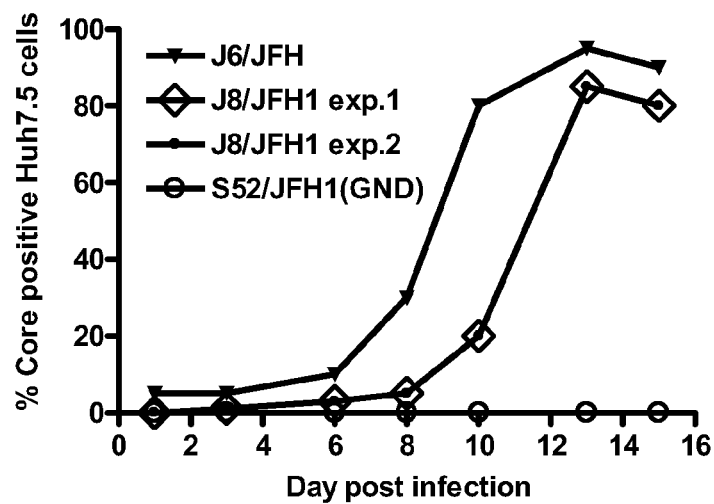
Figure 1D:
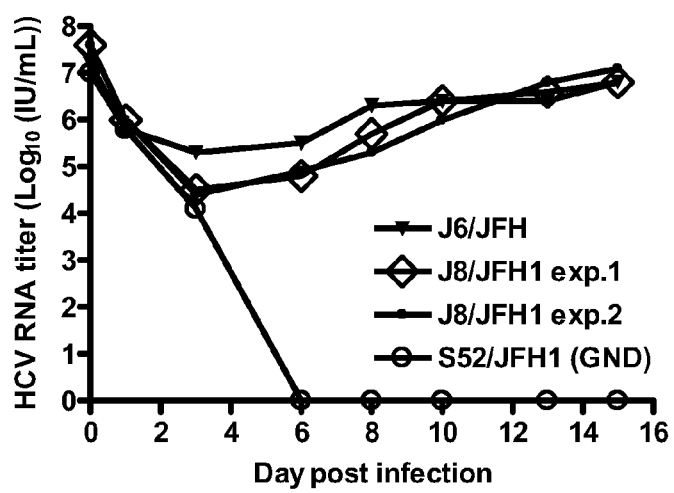

In two independent RNA transfections of Huh7.5 cells, J8/JFH1 spread comparably to J6/JFH with approximately 20% and 80% HCV antigen positive cells on days 1 and 4, respectively (FIG. 1A). The supernatant infectivity titers increased from $\sim10^{1.5}$ TCID$_{50}$/mL on day 1 to $\sim10^{3.5}$ TCID$_{50}$/mL on day 4 (FIG. 1B). During viral passage (FIG. 1C), HCV RNA and infectivity titers were $\sim10^7$ IU/mL (FIG. 1D) and $\sim10^{4.5}$ TCID$_{50}$/mL (data not shown), respectively. Analysis of recovered viruses (days 10 and 13 post-infection, respectively) showed that J8/JFH1 was genetically stable in two first passages performed from the first transfection (FIGS. 1C and D). In the passage of virus from the second transfection (FIGS. 1C and D), G4458A (R1373Q) was present as a 50/50 quasispecies with the original sequence (virus from day 13 post-infection).

Example 2

Titrated Stocks of Genotype 1, 2 and 6 Viruses

The supernatant virus stocks of the JFH1-based intergenotypic recombinants, as well as J6/JFH were characterized (Table 3). Infectivity titers ranged from $10^{3.7}$ to $10^{5.2}$ TCID$_{50}$/mL and HCV RNA titers ranged from $10^{7.0}$ to $10^{7.6}$ IU/mL with specific infectivities (defined as infectious titer relative to the HCV RNA titer) of 1/251-1/3901 TCID$_{50}$/IU.

There was a good correlation between the infectivity titers determined as TCID$_{50}$/mL and FFU/mL, respectively (Table 3).

Example 3

Comparative Kinetic Studies of Intergenotypic Viruses

Figure 2A:
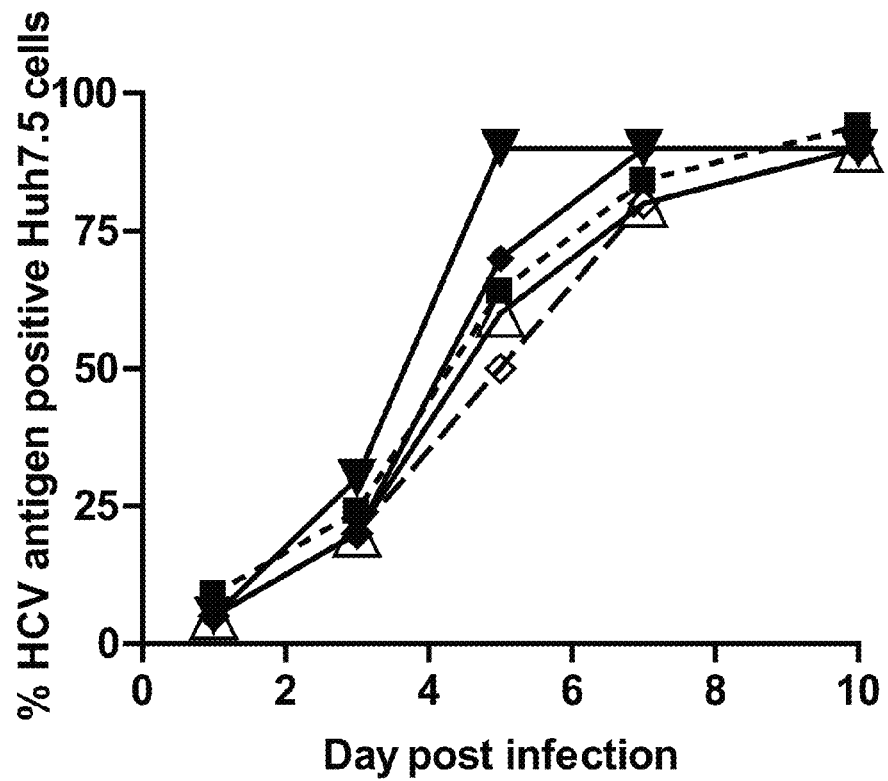
Figure 2B:
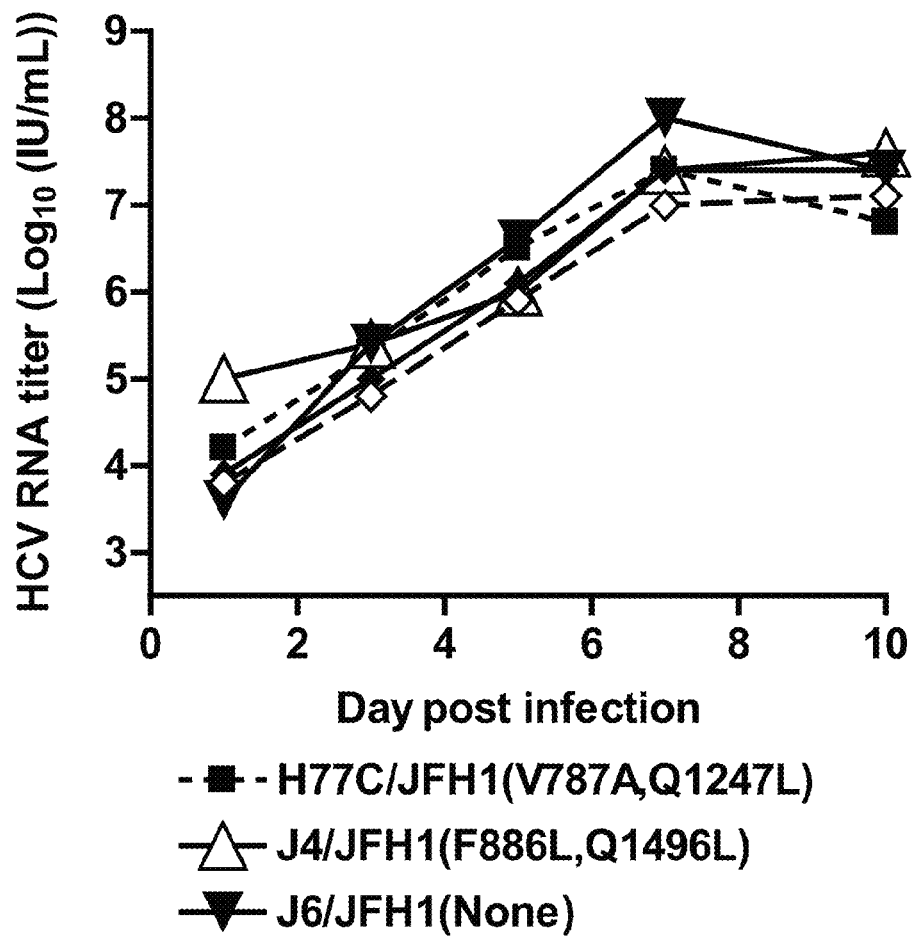
Figure 2C:
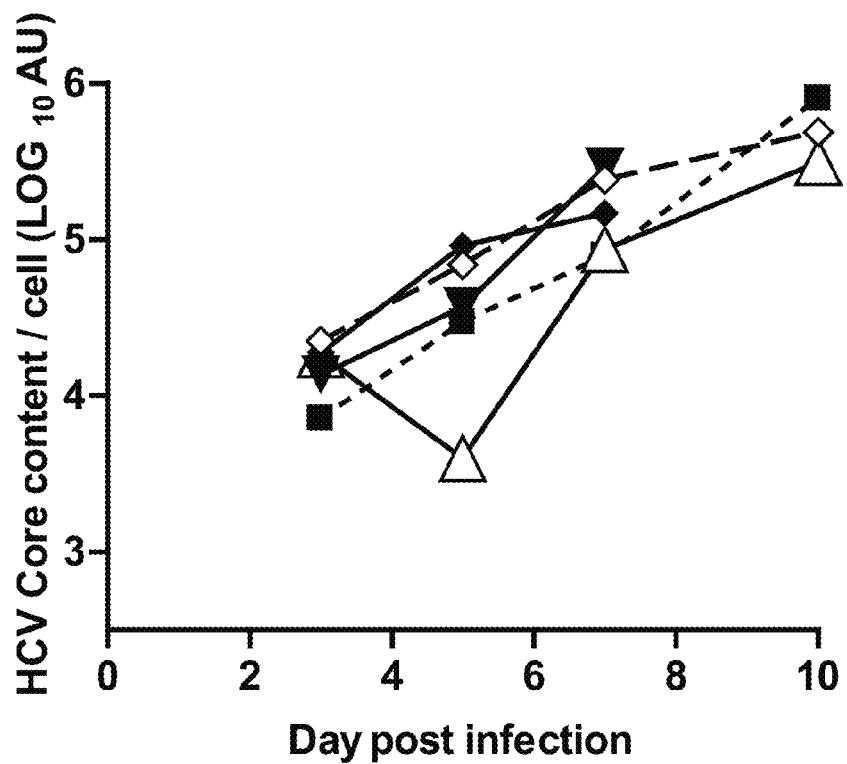
Figure 2D:
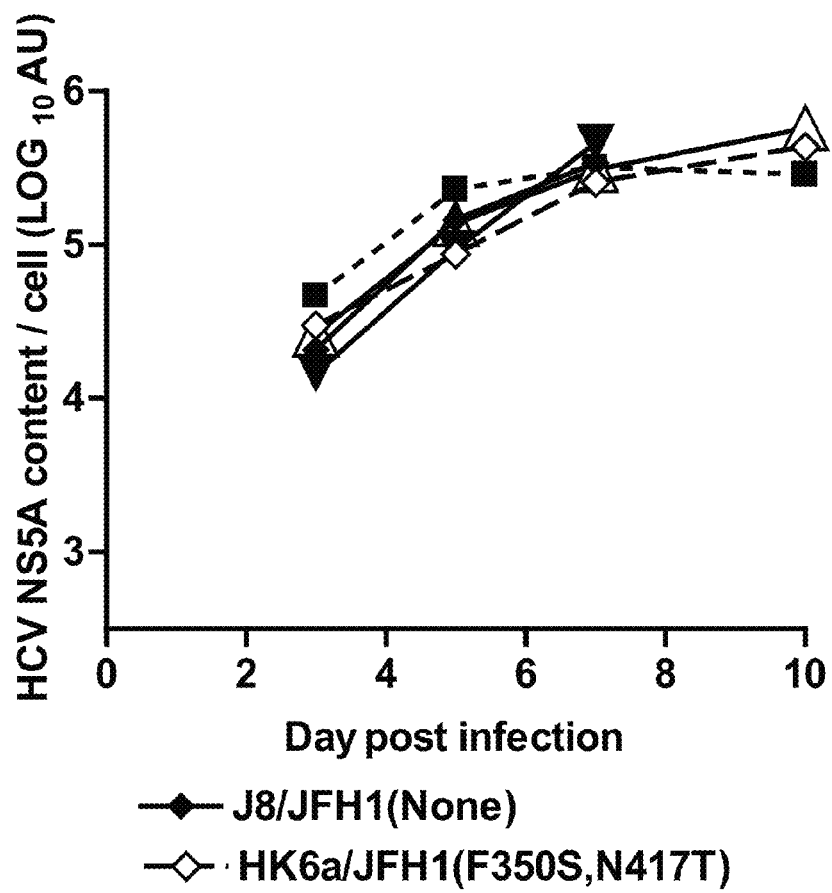
Figure 5:
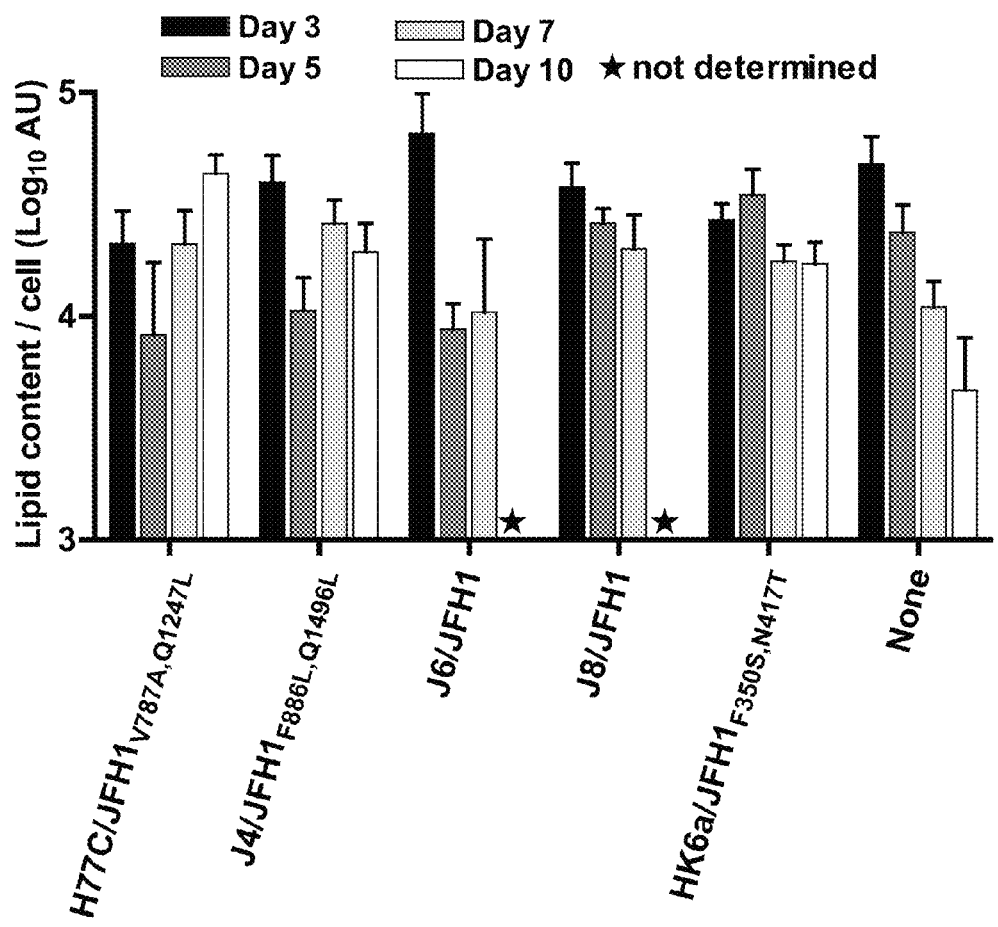

To further characterize the different genotype viruses, a kinetic experiment with genotype 1, 2 and 6 recombinants was performed. After inoculation of Huh7.5 cultures with the respective stock viruses at an MOI of 0.003, efficient spread in 5-10 days (FIG. 2A) was observed, paralleled by a 2-3 log increase in HCV RNA titers to peak titers of >10$^7$ IU/mL (FIG. 2B). In addition, an increase in intracellular Core and NS5A antigen by microscopy based image analyses was observed (FIG. 2C, D). In contrast, increasing infection with genotypes 1-6 did not lead to a change in the average lipid content per cell that was greater than the range of natural variation observed for non-infected cultures (FIG. 5). At peak infection (defined as the first time point with supernatant HCV RNA titers 10$^7$ IU/mL), intracellular HCV RNA and intra- and extracellular infectivity titers were measured (Table 4). Intracellular specific infectivity was at least one order of magnitude lower than extracellular specific infectivity for the respective viruses. It was found that genotype 1, 2 and 6 cultures did not show significant differences in the average intracellular lipid content at the peak of infection (Table 4).

Figure 6:
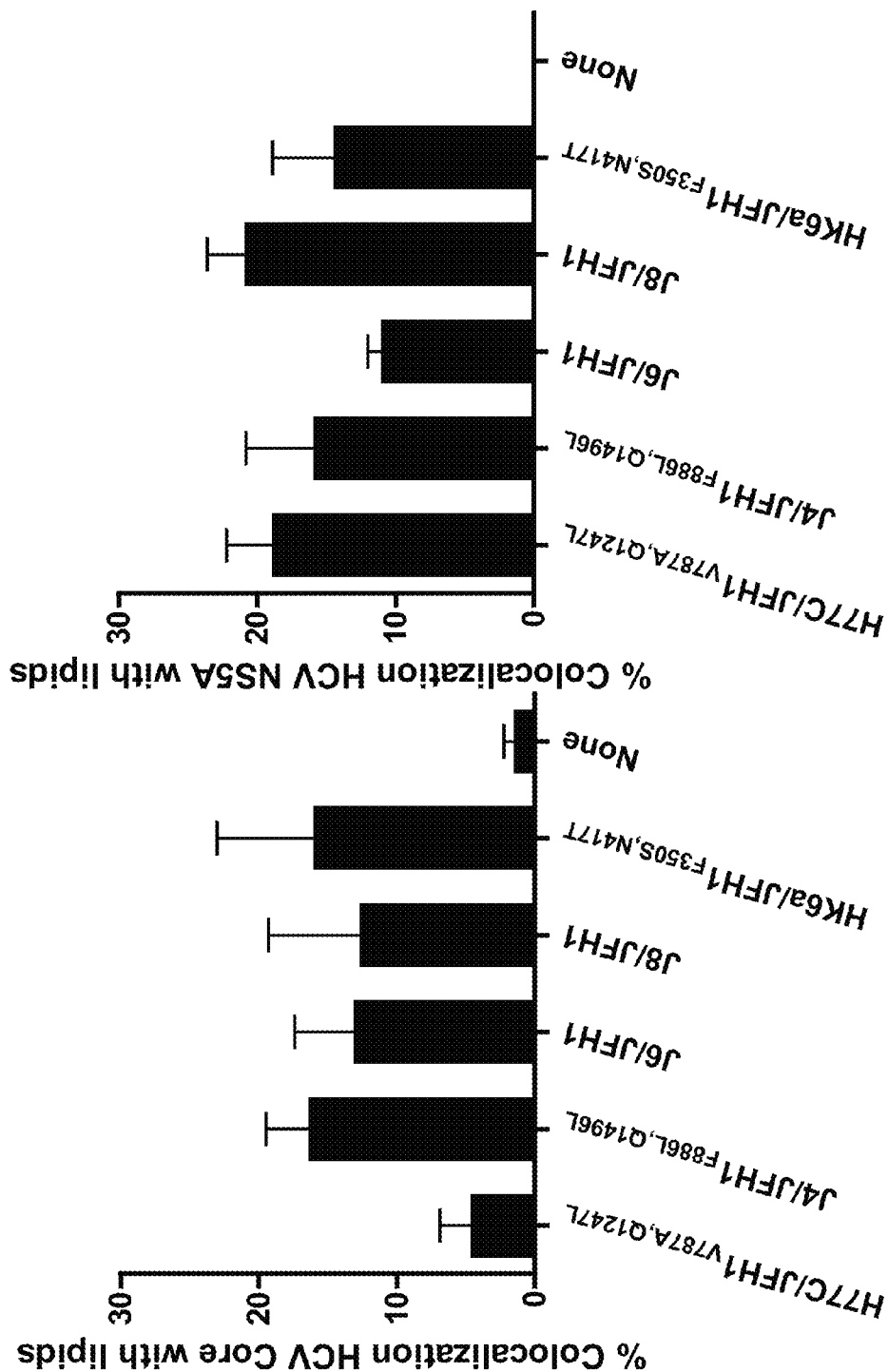

By standard confocal microscopy of genotype 1, 2 and 6 infected Huh7.5 cells co-localization of lipid droplets with Core and NS5A, respectively was observed (data not shown). Using confocal microscopy based image analyses the degree of this co-localization was determined. The analysis indicated that under the set conditions (see Materials and Methods) 5-15% of HCV Core co-localized with lipid droplets with no genotype specific differences. In addition, 10-20% of HCV NS5A co-localized with lipid droplets (FIG. 6).

Example 4

Treatment with Interferon, Ribavirin and Amantadine

The therapeutic potential of drugs currently used or tested for treatment of HCV on Huh7.5 cultures infected with genotype 1, 2 and 6 recombinants was studied. Cells obtained on day 5 of the kinetic experiment (FIG. 2A) were treated with 500 IU/mL interferon-α2b (FIG. 3A, B), 20 μM ribavirin (FIG. 3C, D) or 50 μM amantadine (FIG. 3E, F), respectively. No significant cytotoxic effect was observed (data not shown). After 72 hrs interferon-α2b treatment, an at least 60% decrease in the number of infected cells and a ~2 log decrease in supernatant HCV RNA titers was observed (FIG. 3A, B). Treatment with ribavirin and amantadine did not decrease the number of infected cells or supernatant HCV RNA titers (FIGS. 3C-F). Thus, only interferon-α2b had an antiviral effect with no major differences regarding the genotype of the JFH1-based recombinants treated.

Example 5

Importance of CD81 and SR-B1 for HCV Genotype 1, 2 and 6 Infection

Figure 4B:
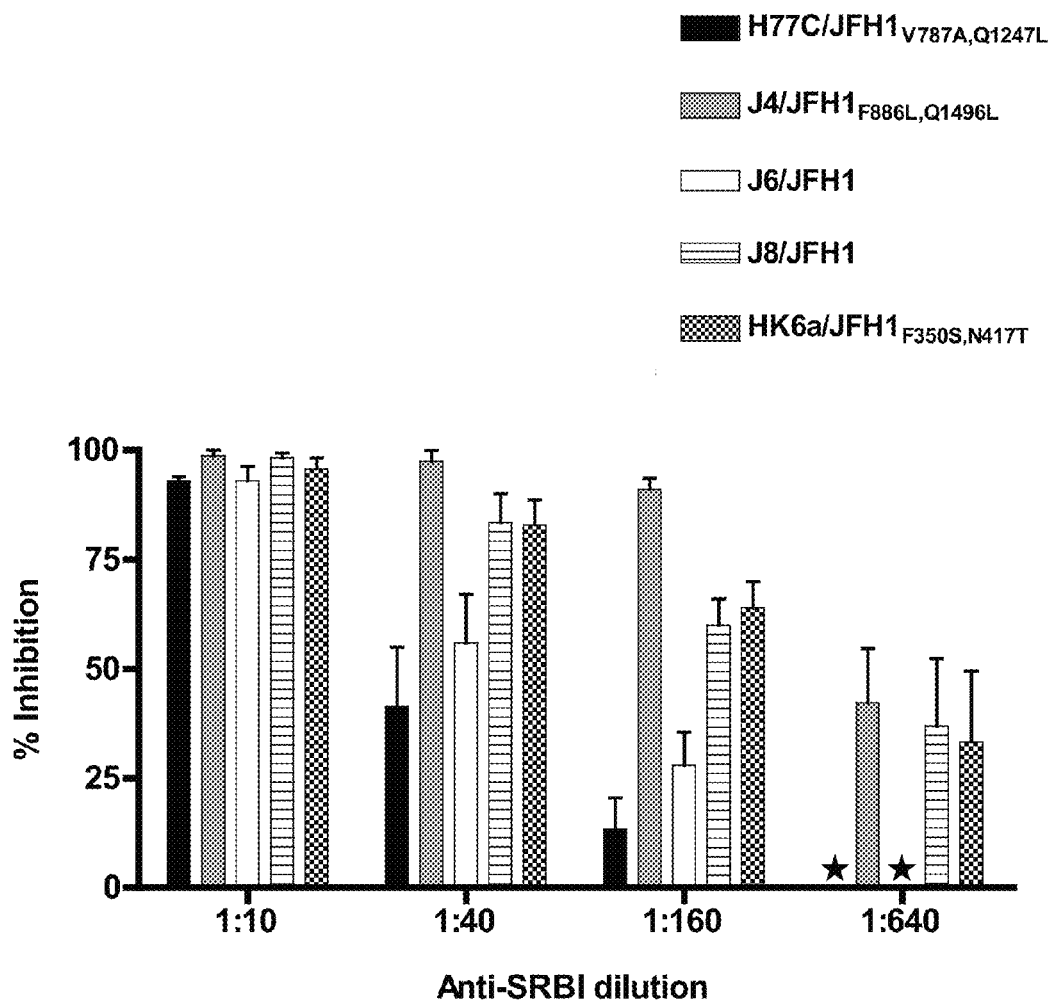

Infection with genotype 1, 2 and 6 recombinants was blocked by anti-CD81 in a dose dependent manner (FIG. 4A); >90% inhibition was observed at 2.5 μg/mL anti-CD81, whereas at 0.02 and/or 0.004 μg/mL anti-CD81<50% inhibition was found. In SR-BI blocking experiments, the present inventors showed for all genotype recombinants >90% infection inhibition with a 1:10 dilution of polyclonal anti-SR-BI (FIG. 4B). This inhibition was dose dependent, and at a 1:640 dilution <50% inhibition was found for all genotype recombinants.

Example 6

Cross-Genotype Neutralization with Chronic Phase HCV Patient Sera

Chronic phase sera from patients infected with genotypes 1a (H06), 4a (AA) and 5a (SA3) with relative high neutralization titers against the homologous genotype virus was identified. The cross-genotype neutralization potential of these sera against 1a, 2a, 3a, 4a, 5a and 6a viruses were tested previously (Table 2). These sera also showed high 50% neutralization titers against the 7a virus (Table 2). Relative high neutralization titers were found against 1b and 2b viruses with the H06 sera, whereas the AA and SA3 sera showed limited neutralization of these viruses (Table 2). It is of interest, that different subtypes as 2a and 2b show a differential susceptibility to neutralization.

FIGURE LEGENDS

FIG. 1

Viability of J8/JFH1 recombinant in Huh7.5 cells. (A and B) Transfection experiment. Huh7.5 cells were transfected in parallel with RNA transcripts from pJ8/JFH1 (two separate experiments; exp. 1 and exp. 2), pJ6/JFH (positive control), pJ6/JFH (GND) (negative control). (A) After immunostaining, the percentage of HCV Core positive cells was scored by fluorescence microscopy. (B) Infectivity titers of transfection supernatants were measured as TCID$_{50}$/mL in single determinations. (C and D) First viral passage. Naïve Huh7.5 cultures were inoculated for 4 hrs with supernatant derived on day 4 after transfection with J8/JFH1 (exp. 1 and exp. 2) and J6/JFH RNA transcripts (A, B) at an MOI of 0.006. As negative control, supernatant derived at day 4 after transfection with S52/JFH1(GND) was used. (C) After immunostaining, the percentage of HCV Core positive cells was scored by fluorescence microscopy. (D) Supernatant HCV RNA titers were measured by Real-Time RT-PCR.

FIG. 2

Comparative kinetics studies of intergenotypic viruses of genotypes 1, 2 and 6. Huh7.5 cells were inoculated with the respective stock virus (Table 3) for 6 hrs (MOI 0.003); J4/JFH1$_{F886L,Q21496L}$ was from a different virus stock. (A) After immunostaining, the percentage of HCV NS5A positive cells was scored by fluorescence microscopy. (B) Supernatant HCV RNA titers were measured by Real-Time RT-PCR. (C, D) Average content of intracellular HCV Core and NS5A was determined by confocal microscopy based quantitative image analysis after immunostaining for the respective antigen. For each culture and antigen, 3 image stacks were acquired, each comprising an average of 110 cells. Average content of HCV antigen per cell was determined for each image using Imaris 6.1.0 software. Means of the 3 datasets are shown. AU, arbitrary units. None-infected negative control cells are not shown; for Core stainings, a background signal of 2.5 Log$_{10}$ AU (mean of 12 determinations) was recorded, whereas NS5A did not show a background signal.

FIG. 3

Treatment of intergenotypic viruses of genotype 1, 2 and 6 with putative antivirals. $4 \times 10^5$ Huh7.5 cells, derived on day 5 of the kinetic experiment (FIG. 2), were plated in 6 well dishes (−12 hrs). After 12 hrs, cell were treated at 0, 6, 12, 24, 48 and 72 hrs with 500 IU/mL interferon-α2b (A, B), 20 µM ribavirin (C, D) or 50 µM amantadine (E, F), respectively. At the indicated time points, percentage of HCV NS5A positive cells was determined using immunostaining and fluorescence microscopy (A, C, E); supernatant HCV RNA titers were measured by Real-Time RT-PCR (B, D, F).

FIG. 4

Importance of CD81 and SR-BI for entry of intergenotypic viruses. $6 \times 10^3$ Huh7.5 cells per well of a 96 well plate were treated for 1 hr with either anti-CD81 (A) or anti-SR-BI (B) at the indicated concentrations. ~150 FFU of the respective virus were added for 3 hrs. Virus stocks shown in Table 3 were used. After 48 hrs, the number of FFU was evaluated following immunostaining for HCV NS5A. % inhibition was calculated by relating the number of FFU/well to the mean number of FFU/well of 3 untreated wells. Means of triplicates and standard errors of the mean are shown. Control antibody preparations specified in Materials and Methods did not show any inhibitory effect at the equivalent concentrations. Stars, value<0. Data shown in B were generated in three different experiments (1st experiment: 1:10, 1:40 and 1:160 dilutions (1:160 not shown); 2nd experiment: 1:160 and 1:640 dilutions; 3rd experiment: all dilutions for J4/JFH1$_{F886L,Q21496L}$ viruses). The efficient blocking of infection of the different genotype recombinants with anti-SR-BI was confirmed in an independent experiment (data not shown). The apparent genotype specific differences seen at 1:160 dilution were only reproducible in 2 of 3 independent experiments.

FIG. 5

Average content of intracellular lipids during infection with genotype 1, 2 and 6 viruses. At day 3, 5, 7, and 10 after infection (FIG. 2) with the indicated JFH1-based recombinants, $5 \times 10^4$ Huh7.5 cells of the respective cultures were plated on chamber slides. After 24 hrs, lipid droplets were stained with oil-red O, HCV antigen was stained with either anti-Core or anti-NS5A antibodies, and cell nuclei were stained with Hoechst reagent. For each culture, 6 image stacks were acquired, each of them comprised of on average 110 cells, using confocal microscopy imaging. Average content of lipids per cell was determined for each image using Imaris 6.1.0 software. Means and SEM of the 6 datasets are shown. AU, arbitrary units. Star, time points not analysed.

FIG. 6

Co-localization of HCV antigens with lipid droplets. At day 5 after infection (FIG. 2) with the indicated JFH1-based recombinants, $5 \times 10^4$ Huh7.5 cells of the respective cultures were plated on chamber slides. After 24 hrs, lipid droplets were stained with oil-red O, HCV antigen was stained with either anti-Core or anti-NS5A antibodies, and cell nuclei were stained with Hoechst reagent. For each culture and antigen, 4 image stacks were acquired, each comprising >20 cells, using confocal microscopy imaging. Average % of co-localization was determined for each image stack using Imaris 6.1.0. Means and SEM of the 4 datasets are shown. Low % of co-localization of Core with lipids for the none-infected culture is due to a background signal observed in Core stainings (see also FIG. 2).

Tables

TABLE 1

Primers used for J8/JFH1 long RT-PCR procedure to generate amplicons for direct sequencing of the ORF*

| Amplification step and amplicon 2nd round PCR | Primer name | SEQ ID NO | Primer sequence |
| --- | --- | --- | --- |
| Amplicon 1 | -84S_HCV-MOD | SEQ ID NO: 3 | 5'-GTAGCGTTGGGTTGCGAAAGGCCTTGTGGTACTGCCTGAT-3' |
| | J8 R1458 fus | SEQ ID NO: 4 | 5'-CAATGACTTTGGCCCACGCTCCTTG-3' |
| Amplicon 2 | J8 F1286 fus | SEQ ID NO: 5 | 5'-CCATCGCATGGCATGGGACATGATGC-3' |
| | J8R2309 | SEQ ID NO: 6 | 5'-GCAGCGATCTCCGCGCGTGAAGT-3' |
| Amplicon 3 | J8F1989 | SEQ ID NO: 7 | 5'-GCTTGGTTCGGCTGCACTTGGATGAAC-3' |
| | J8 R3003 | SEQ ID NO: 8 | 5'-GGCGTGGGTGTAGAATGACAGCCACCC-3' |
| Amplicon 4 | J8F2762 | SEQ ID NO: 9 | 5'-ACCACAGCAGGCTTATGCCTTGGACG-3' |
| | 3774R_J6 | SEQ ID NO: 10 | 5'-GGGATGACATCAGCGTTCCGCGTGACCAG-3' |
| Amplicon 5 | J8F3167 | SEQ ID NO: 11 | 5'-GATCACCATAGGCAGATGGACCGGCACTTA-3' |
| | 4118R_JFH1 | SEQ ID NO: 12 | 5'-CGCCCGAGGCCTACCTCTTCTATATC-3' |

*Primers used for cDNA synthesis, 1$^{st}$ round PCR and 2$^{nd}$ round PCR amplicon 6 to 12 bind to the JFH1 portion of the recombinant and are given in Supplementary Material and Methods of Gottwein et al. (2007).

TABLE 2

Cross-genotype neutralization potential of chronic phase genotype 1a, 4a and 5a serum against genotype 1-7 recombinant viruses.

| Core-NS2 | Reciprocal 50% serum neutralizing antibody titer | | |
| --- | --- | --- | --- |
| Genotype | 1a (H06) | 4a (AA) | 5a (SA3) |
| 1a | 1600 | <100* | <100 |
| 1b | 800 | <100* | <100* |
| 2a | <100* | <100** | <100 |
| 2b | 3200 | 400 | 200 |
| 3a | <100* | <100** | <100 |
| 4a | 12800 | 6400 | 200 |
| 5a | 25600 | 3200 | 6400 |
| 6a | 204800 | 25600 | 12800 |
| 7a | 25600 | 3200 | 1600 |

Neutralization of genotype 1a, 2a, 3a, 4a, 5a and 6a viruses with 1a (H06), 4a (AA) and 5a (SA3) chronic phase serum was described previously. Similarly, approximately 150 FFU of J4/JFH1$_{F886L,Q21496L}$, 80 or 150 FFU of J8/JFH1, and 30 FFU of QC69/JFH1 stock viruses were pre-incubated with 2-fold dilutions of sera in triplicates, before infection of $6 \times 10^3$ Huh7.5 cells for 3 hrs. After 48 hrs incubation, the number of FFUs was determined for each culture by anti- NS5A immunostaining. 50% neutralization titers indicate the serum dilution, which led to an at least 50% reduction of FFU compared to the mean of 6 non-serum treated cultures. * 50% neutralization observed at 1:50 serum dilution; ** less than 50% neutralization observed at 1:50 serum dilution.

TABLE 3

Titrated Stocks of JFH1-based Intergenotypic Recombinants of HCV Genotype 1, 2 and 6.

| Core-NS2 Genotype | Virus † | Viral Passage | HCV Infectivity titer* | | HCV RNA titer # | Specific infectivity** |
|---|---|---|---|---|---|---|
| | | | $LOG_{10}$ $TCID_{50}$/mL | $LOG_{10}$ FFU/mL | $LOG_{10}$ IU/mL | $TCID_{50}$/IU |
| 1a | H77C/JFH1$_{V787A,Q1247L}$ | 2nd | 4.3 ± 0.0 | 4.3 ± 0.2 | 7.5 ± 0.1 | 1/1585 |
| 1b | J4/JFH1$_{F886L,Q1496L}$ | 1st | 3.7 ± 0.3 | 3.2 ± 0.0 | 7.3 ± 0.1 | 1/3981 |
| 2a | J6/JFH1 | 2nd | 5.2 ± 0.1 | 5.0 ± 0.2 | 7.6 ± 0.0 | 1/251 |
| 2b | J8/JFH1 | 1st | 4.4 ± 0.1 | 4.1 ± 0.1 | 7.4 ± 0.0 | 1/1000 |
| 6a | HK6a/JFH1$_{F350S,N417T}$ | 1st | 4.4 ± 0.2 | 4.0 ± 0.0 | 7.0 ± 0.0 | 1/398 |

† HCV recombinant with engineered adaptive mutations given as subscript. HCV ORF sequences, including the presence of specific mutations, were verified by direct sequencing of stock genomes; additionally, a 50/50 quasispecies coding mutation was revealed for H77C/JFH1 (Y361Y/H).
*Measured as $TCID_{50}$/mL (mean of four determinations, each based on serial dilution with 6 replicates per dilution; ±SEM, standard error of the mean) and FFU/mL (mean of two determinations, each based on serial dilution with 6 replicates per dilution; ±SEM),
Measured as IU/mL (mean of two determinations, ±SEM) in a Real-Time RT-PCR assay.
**Determined as HCV RNA titer (IU/mL) related to HCV infectivity titer ($TCID_{50}$/mL).

TABLE 4

Characterization of genotype 1, 2 and 6 kinetic cultures at peak of infection.

| Core-NS2 Genotype | Virus † | Day* | Infection# % | HCV RNA titer** | | HCV Infectivity titer& | | Specific infectivity | | HCV Antigen $ | | Lipid $ |
|---|---|---|---|---|---|---|---|---|---|---|---|---|
| | | | | EC ‡ $LOG_{10}$ IU/mL | IC ## $LOG_{10}$ IU/$10^5$ cells | EC ‡ $LOG_{10}$ FFU/mL | IC ## $LOG_{10}$ FFU/$10^5$ cells | EC ‡ FFU/IU | IC ## FFU/IU | Core/cell $LOG_{10}$ AU | NS5A/cell $LOG_{10}$ | Lipid/cell $LOG_{10}$ |
| 1a | H77C/JFH1$_{V787A,Q1247L}$ | 7 | 80 | 7.4 | 7.2 | 4.0 | 2.7 | 1/2512 | 1/31623 | 4.9 | 5.5 | 4.3 |
| 1b | J4/JFH1$_{F886L,Q1496L}$ | 7 | 80 | 7.4 | 6.6 | 4.0 | 1.9 | 1/2512 | 1/50119 | 4.9 | 5.5 | 4.4 |
| 2a | J6/JFH1 | 7 | 90 | 8.0 | 7.2 | 5.1 | 2.5 | 1/794 | 1/50119 | 5.5 | 5.7 | 4.0 |
| 2b | J8/JFH1 | 7 | 90 | 7.4 | 7.3 | 4.6 | 2.7 | 1/631 | 1/39811 | 5.2 | 5.5 | 4.3 |
| 6a | HK6a/JFH1$_{F350S,N417T}$ | 7 | 80 | 7.0 | 7.0 | 4.1 | 1.9 | 1/794 | 1/125893 | 5.4 | 5.4 | 4.2 |
| None | None | 7 | 0 | nd | nd | nd | nd | na | na | 3.0 | nd | 4.0 |

† HCV recombinant with engineered adaptive mutations used in comparative kinetic study (FIG. 4).
*The first time point (day), at which HCV RNA titers in culture supernatant were ≥$10^7$ IU/mL (FIG. 4B).
% infected cells scored using fluorescence microscopy (FIG. 4A).
**IU/mL or IU/$10^5$ cells.
‡ EC, extracellular analysis was carried out on culture supernatants.
IC, for intracellular analysis pellets of $10^5$ cells were resuspended in growth medium and subjected to 4 freeze/thaw cycles. After centrifugation, supernatants were analysed.
&FFU/mL or FFU/$10^5$ cells (mean of three determinations, each based on serial dilution with 1 replicate per dilution).

REFERENCES

Billaud, J. N. et al. (2000). Replication rate of feline immunodeficiency virus in astrocytes is envelope dependent: implications for glutamate uptake. Virology 266, 180-188.

Engle, R. E. et al. (2008) TaqMan assay for the six major genotypes of hepatitis C virus: comparison with commercial assays. J Med Virol. 80, 72-79.

Gottwein, J. M. et al. (2007) Robust Hepatitis C Genotype 3a Cell Culture Releasing Adapted Intergenotypic 3a/2a (S52/JFH1) Viruses Gastroenterology 133, 1614-1626.

Jensen, T. B. et al. (2008). Highly efficient JFH1-based cell culture system of hepatitis C virus genotype 5a: failure to control infection with homologous neutralizing antibody treatment. J Inf Dis. in press.

Kato, T. et al. (2001). Sequence analysis of hepatitis C virus isolated from a fulminant hepatitis patient. J Med Virol. 64, 334-339

Kato, T. et al. (2003). Efficient replication of the genotype 2a hepatitis C virus subgenomic replicon. Gastroenterology. 125, 1808-1817.

Lindenbach, B. D. et al. (2005) Complete replication of hepatitis C virus in cell culture. Science. 309, 623-626.

Lindenbach, B. D. et al. (2006) Cell culture-grown hepatitis C virus is infectious in vivo and can be recultured in vitro. Proc Natl Acad Sci USA. 103(10), 3805-9. Epub 2006 Feb. 16

Meunier, J. C. et al. (2005) Evidence for Cross-Genotype Neutralization of Hepatitis C Virus Pseudo-Particles and Enhancement of Infectivity by Apolipoprotein C1 Proc Natl Acad Sci USA 102, 4560-4565.

Scheel, T. K., et al. (2008) Development of JFH1-based cell culture systems for hepatitis C virus genotype 4a and evidence for cross-genotype neutralization. Proc Natl Acad Sci USA 105, 997-1002.

Wakita, T. et al (2005). Production of infectious hepatitis C virus in tissue culture from a cloned viral genome. Nat. Med. 11, 791-796.

Zhong, J. et al. (2005). Robust hepatitis C virus infection in vitro. Proc. Natl. Acad. Sci. U.S.A. 102, 9294-9299.

The invention claimed is:

1. A nucleic acid molecule encoding an amino acid sequence with at least 98% identity to SEQ ID NO:2, wherein said molecule is a genetically engineered human Hepatitis C virus intergenotypic recombinant that comprises the structural Core, E1, and E2 genes, the p7 gene and the non-structural NS2 gene of genotype 2b, and the non-structural genes NS3, NS4A, NS4B, NS5A and NS5B, of genotype 2a, strain JFH1.

2. The nucleic acid molecule according to claim 1, wherein said molecule comprises the nucleic acid sequence with at least 98% to SEQ ID NO: 1 and is selected from the group consisting of double stranded DNA complementary DNA (cDNA), positive-sense cDNA, negative-sense cDNA, positive-sense RNA, negative-sense RNA, and double stranded RNA.

3. The nucleic acid molecule according to claim 1, wherein said molecule comprises one adaptive mutation, and said adaptive mutation is a replacement of G at position 4458 of SEQ ID NO: 1 with A.

4. The nucleic acid molecule according to claim 1, wherein said molecule comprises one adaptive mutation, and said adaptive mutation is a replacement of R at position 1373 of SEQ ID NO: 2 with Q.

5. The nucleic acid molecule according to claim 1, wherein said molecule is capable of generating a HCV infectivity titer of $10^2$ $TCID_{50}$/ml (50% tissue culture infectious doses)/ml or above following transfection and/or subsequent viral passage.

6. The nucleic acid molecule according to claim 1, wherein said molecule encodes the amino acid sequence with at least 99% identity to SEQ ID NO: 2.

7. An isolated cell comprising a nucleic acid molecule of claim 1.

8. The cell according to claim 7, wherein the cell is Huh7.5.

9. The cell according to claim 7, wherein said molecule comprises one adaptive mutation and wherein said adaptive mutation is a replacement of R at position 1373 of SEQ ID NO: 2 with Q.

10. A method for producing a hepatitis C virus particle, comprising culturing the cell according to claim 7 to allow the cell to produce the genetically engineered human Hepatitis C virus intergenotypic recombinant.

11. An isolated hepatitis C virus particle comprising the nucleic acid molecule according to claim 1.

12. The nucleic acid molecule according to claim 1, wherein said molecule encodes the amino acid sequence of SEQ ID NO: 2.

13. The nucleic acid molecule according to claim 6, wherein said molecule comprises one adaptive mutation and wherein said adaptive mutation is a replacement of R at position 1373 of SEQ ID NO: 2 with Q.

14. The nucleic acid molecule according to claim 1, wherein said molecule comprises the nucleic acid sequence with at least 99% identity to SEQ ID NO: 1.

15. The nucleic acid molecule according to claim 1, wherein said molecule comprises the nucleic acid sequence with of SEQ ID NO: 1.

16. The nucleic acid molecule according to claim 14, wherein said molecule comprises one adaptive mutation, and said adaptive mutation is a replacement of G at position 4458 of SEQ ID NO: 1 with A.

17. The nucleic acid molecule according to claim 1, wherein said genetically engineered human Hepatitis C virus intergenotypic recombinant comprises the structural Core, E1, and E2 genes, the p7 gene, and the non-structural NS2 gene of genotype 2b, strain J8, and the non-structural genes NS3, NS4A, NS4B, NS5A, and NS5B of genotype 2a, strain JFH1.

* * * * *